(12) United States Patent
Yan

(10) Patent No.: US 11,446,376 B2
(45) Date of Patent: Sep. 20, 2022

(54) METHODS FOR TREATING HEART FAILURE USING GLUCAGON RECEPTOR ANTAGONISTIC ANTIBODIES

(71) Applicant: REMD Biotherapeutics, Inc., Camarillo, CA (US)

(72) Inventor: Hai Yan, Thousand Oaks, CA (US)

(73) Assignee: REMD Biotherapeutics, Inc., Camarillo, CA (US)

(*) Notice: Subject to any disclaimer, the term of this patent is extended or adjusted under 35 U.S.C. 154(b) by 57 days.

(21) Appl. No.: 16/941,290

(22) Filed: Jul. 28, 2020

(65) Prior Publication Data

US 2020/0353079 A1 Nov. 12, 2020

Related U.S. Application Data

(63) Continuation of application No. 15/757,352, filed as application No. PCT/US2016/050183 on Sep. 2, 2016, now Pat. No. 10,765,737.

(60) Provisional application No. 62/259,061, filed on Nov. 24, 2015, provisional application No. 62/214,449, filed on Sep. 4, 2015.

(51) Int. Cl.

| C07K 16/28 | (2006.01) |
|---|---|
| A61K 39/395 | (2006.01) |
| A61K 38/26 | (2006.01) |
| A61K 45/06 | (2006.01) |
| A61P 9/10 | (2006.01) |
| A61K 9/00 | (2006.01) |
| A61K 39/00 | (2006.01) |
| A61K 36/68 | (2006.01) |

(52) U.S. Cl.
CPC ...... *A61K 39/39533* (2013.01); *A61K 9/0019* (2013.01); *A61K 38/26* (2013.01); *A61K 45/06* (2013.01); *A61P 9/10* (2018.01); *C07K 16/2869* (2013.01); *A61K 36/68* (2013.01); *A61K 2039/505* (2013.01); *A61K 2039/57* (2013.01); *C07K 2317/21* (2013.01); *C07K 2317/76* (2013.01)

(58) Field of Classification Search
CPC . A61K 39/3953; A61K 2317/76; A61K 38/26
See application file for complete search history.

(56) References Cited

U.S. PATENT DOCUMENTS

| 2009/0239844 A1 | 9/2009 | Pressler |
| 2011/0223160 A1 | 9/2011 | Yan et al. |
| 2012/0121530 A1 | 5/2012 | Klein et al. |
| 2013/0251728 A1 | 9/2013 | Harp et al. |

FOREIGN PATENT DOCUMENTS

| WO | 2006005469 | 1/2006 |
| WO | 2008036341 | 3/2008 |

OTHER PUBLICATIONS

Ali et al., Mol. Metab. 4: 132-143, (2015).*
Fuentes-Antrás et al., "Targeting metabolic disturbance in the diabetic heart", Cardiovascular Diabetology, 14:17, 2015.
Isfort et al, "Metabolic Dysfunction in Diabetic Cardiomyopathy", Heart Fail Rev., 19(1), Jan. 2014.
PCT Written Opinion of the International Search Authority, dated Jan. 13, 2017.
Robert J Chilton, "Potential Cardiovascular Effects of the Glucagon-like Peptide-1 Receptor Agonist", J Diabetes Metab, 6:1, Jan. 1, 2015.
Gu et al, "Pharmacological Targeting of Glucagon and Glucagon-like Peptide 1 Receptors has Different Effects on Enrgy State and Glucose Hemeostasis in Diet-Induced Obese Mice", The Journal of Pharmacology and Experimental Therapeutics, 338(1), pp. 70-81, Jul. 1, 2011.
European Patent Office Search Report, dated Feb. 25, 2019.

\* cited by examiner

*Primary Examiner* — Gyan Chandra
(74) *Attorney, Agent, or Firm* — Craig A Crandall, APC; Craig A Crandall

(57) ABSTRACT

The present disclosure relates to methods for treating or preventing heart failure using a glucagon receptor blocking agent. In various embodiments, the present disclosure relates to methods for treating or preventing heart failure (e.g., post-myocardial infarction heart failure), diabetic cardiomyopathy heart failure), and lateral ventricular (LV) remodeling, using antigen binding and antagonizing proteins, e.g., fully human antibodies, that specifically bind to and antagonize the function of the human glucagon receptor.

11 Claims, 32 Drawing Sheets
(32 of 32 Drawing Sheet(s) Filed in Color)
Specification includes a Sequence Listing.

mAb

CON

GLC

METHODS FOR TREATING HEART FAILURE USING GLUCAGON RECEPTOR ANTAGONISTIC ANTIBODIES

CROSS-REFERENCE TO RELATED APPLICATIONS

This application is a Continuation Application of U.S. application Ser. No. 15/757,352, filed Mar. 3, 2018, which is a U.S. National Stage Application pursuant to 35 U.S.C. § 371 of PCT/US2016/050183, filed Sep. 2, 2016, which claims priority to provisional application U.S. Ser. No. 62/214,449, filed Sep. 4, 2015, and U.S. Ser. No. 62/259,061, filed Nov. 24, 2015, each hereby incorporated by reference in their entirety.

BACKGROUND

Heart failure (HF) is a global problem with an estimated prevalence of 38 million patients worldwide, including 6 million in the United States and more than 550,000 new patients diagnosed with the condition in the US each year. HF is the most common diagnosis in patients aged 65 years or older admitted to hospital and it is one of the most significant causes of morbidity and mortality in developed countries.

Heart failure is a clinical syndrome characterized by the failure of the heart to pump sufficient blood to meet the body's systemic demands. The heart contracts and relaxes with each heartbeat—these phases are referred to as systole (the contraction phase) and diastole (the relaxation phase). Systolic heart failure (SHF) is characterized by low ejection fraction. In patients with diastolic heart failure (DHF), contraction may be normal but relaxation of the heart may be impaired. This impairment is generally caused by a stiffening of the ventricles. Such impairment is referred to as diastolic dysfunction and if severe enough to cause pulmonary congestion (increased pressure and fluid in the blood vessels of the lungs), diastolic heart failure. DHF patients differ from those patients with SHF, in that DHF patients may have a "normal" ejection fraction. However, because the ventricle doesn't relax normally, the pressure within the ventricle increases and the blood filling the ventricle exceeds what is "normal". People with certain types of cardiomyopathy may also have diastolic dysfunction.

Left ventricular hypertrophy (LVH) refers to a thickening of the left ventricle as a result of increased left ventricular load. LVH can be a significant marker for cardiovascular disorders and most common complications include arrhythmias, heart failure, ischemic heart disease, and sudden death. Although LVH increases naturally with age, it is more common in people who have high blood pressure or have other heart problems. Because LVH usually develops in response to hypertension, current treatment and prevention mainly includes managing hypertension. Typical diagnosis involves the use of echocardiograms (ECHO) and electrocardiograms (ECG).

Myocardial infarction (MI) is a leading cause for heart failure. The mechanism of an MI often involves the rupture of an atherosclerotic plaque leading to complete blockage of a coronary artery which resulted in the death or damage of heart muscle cells because the heart muscle cells do not receive enough oxygen. Diabetes mellitus (type 1 or 2), high blood pressure, dyslipidemia/high levels of blood cholesterol, particularly high low-density lipoprotein, low high-density lipoprotein, high triglycerides, and obesity have all been linked to myocardial infarction (Jay N. Cohn, et al., Journal of the American College of Cardiology, 35(3), 569-82, 2000). Long-term outcome after MI can be largely be defined in terms of its impact on the size and shape of the left ventricle (i.e., LV remodeling). Three major mechanisms contribute to LV remodeling: i) early infarct expansion, ii) subsequent infarct extension into adjacent non infarcted myocardium, and iii) late hypertrophy in the remote LV (Id). As the heart remodels, it not only gets bigger, but the cardiac walls get thinner and the pumping capacity of the heart declines. Cardiac remodeling is generally accepted as a determinant of survival after recovery from MI. Although the importance of remodeling as a pathogenic mechanism is incompletely understood, cardiac remodeling is thought to be an important aspect of disease progression in HF, regardless of cause (Id). Left ventricular remodeling is the process by which ventricular size, shape, and function are regulated by mechanical, neuro-hormonal, and genetic factors. Remodeling may be physiological and adaptive during normal growth or pathological due to MI, cardiomyopathy, hypertension, or valvular heart disease (French and Kramer, Drug Discov. Today Dis Mech., 4(3): 185-196, 2007).

It was recently reported that glucagon receptor signaling in cardiomyocytes modulates outcomes in non-diabetic mice with experimental myocardial infarction (Ali, et al., Molecular Metabolism, 4:132-143, 2015). Specifically, exogenous glucagon administration directly impaired recovery of ventricular pressure in ischemic mouse hearts ex vivo, and increased mortality from myocardial infarction after LAD coronary artery ligation in mice in a p38 MAPK-dependent manner. In contrast, cardiomyocyte specific reduction of glucagon action in adult $GCGR^{CM-/-}$ mice (mice having GCGR inactivated) significantly improved survival, and reduced hypertrophy and infarct size following myocardial infarction (Id.) The authors conclude that the cardiovascular consequences of manipulating glucagon action remain poorly understood and emphasize the need to acquire a further understanding of such consequences (Id.)

Current drug treatments available for management of heart failure, and other cardiovascular disorders, include vasodilators to reduce the blood pressure and ease the workload of the heart, diuretics to reduce fluid overload, inhibitors and blocking agents of the body's neuro-hormonal responses (e.g., angiotensin-converting enzyme (ACE) inhibitors and beta-adrenergic blocking agents), and other medicaments. Such medications, while effective for a short time, often cannot be used for extended periods because of side effects. Various surgical procedures such as heart transplantation have also been proposed for patients who suffer from severe, refractory heart failure. Alternatively, an implantable medical device such as ventricular assist devices (VADs) may be implanted in the chest to increase the pumping action of the heart, or an intra-aortic balloon pump (IABP) may be used for maintaining heart function for short periods of time, but typically no longer than one month. While each of these approaches have proven to be at least partly beneficial to patients, they each have shortcomings which limit their overall effectiveness. For example, drug therapies often involve unwanted side effects and complex therapy regimens which contribute to poor patient compliance. And both drug therapy and surgical approaches are very costly, adding to the health care costs associated with heart failure. Despite the ongoing research and development of treatments for heart failure, there is still a tremendous need for improved and alternative treatments.

SUMMARY OF THE INVENTION

The present disclosure is based in part on the inventors' unique insight that isolated antigen binding and antagonizing proteins that specifically bind to the human glucagon receptor may provide for improved, effective therapies for treatment and prevention of heart failure after myocardial infarction, and prevention of heart failure associated with diabetes and hyperglycemia. The present inventor proposes that the beneficial therapeutic effects provided by blocking the glucagon receptor in myocardial infarction-induced heart failure subjects (or all other heart failure subjects) relate to the prevention or attenuation of left ventricular (LV) remodeling which may include: increasing fractional shortening (FS), decreasing LV dilation (LVESD); preserving LV wall thickness; increasing LV developed pressure and ventricular contractility; decreasing the ratio of heart weight to body weight (infarct size); reducing the fibrosis process; reducing levels of incompletely oxidized fatty acid metabolites in the heart under ischemic conditions; and reducing MI-induced mortality rate.

Thus, in one aspect, the present disclosure comprises a method for treating or preventing heart failure and associated conditions in a subject, comprising administering to a subject diagnosed with heart failure, or a subject at risk of contracting heart failure, a therapeutically effective amount of an isolated antagonistic antigen binding protein that specifically binds to the human glucagon receptor. In various embodiments, the present disclosure comprises a method for treating or preventing heart failure after myocardial infarction. In various embodiments, the present disclosure comprises a method for treating or preventing heart failure associated with diabetes mellitus. In various embodiments, the present disclosure comprises a method for treating or preventing heart failure associated with diabetic cardiomyopathy.

In various embodiments, the isolated antagonistic antigen binding protein comprises an antibody selected from a fully human antibody, a humanized antibody, a chimeric antibody, a monoclonal antibody, a polyclonal antibody, a recombinant antibody, an antigen-binding antibody fragment, a Fab, a Fab', a Fab$_2$, a Fab'$_2$, a IgG, a IgM, a IgA, a IgE, a scFv, a dsFv, a dAb, a nanobody, a unibody, or a diabody. In various embodiments, the antibody is a fully human monoclonal antibody. In various embodiments, the isolated antibody or antigen-binding antibody fragment specifically binds to a human glucagon receptor with a dissociation constant ($K_D$) of at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M.

In various embodiments, the isolated antagonistic antigen binding protein comprises an antibody which comprises the amino acid sequence encoding the heavy chain variable region of SEQ ID NO: 2 and the amino acid sequence encoding the light chain variable region of SEQ ID NO: 3. In various embodiments, the isolated antagonistic antigen binding protein comprises an antibody which comprises the amino acid sequence encoding the heavy chain variable region of SEQ ID NO: 4 and the amino acid sequence encoding the light chain variable region of SEQ ID NO: 5. In various embodiments, the isolated antagonistic antigen binding protein comprises an antibody which comprises the amino acid sequence encoding the heavy chain variable region of SEQ ID NO: 6 and the amino acid sequence encoding the light chain variable region of SEQ ID NO: 7. In various embodiments, the isolated antagonistic antigen binding protein comprises an antibody which comprises the amino acid sequence encoding the heavy chain of SEQ ID NO: 8 and the amino acid sequence encoding the light chain of SEQ ID NO: 9. In various embodiments, the isolated antagonistic antigen binding protein comprises an antibody which comprises the amino acid sequence encoding the heavy chain variable region selected from the group consisting of SEQ ID NOs: 10-28, and the amino acid sequence encoding the light chain variable region selected from the group consisting of SEQ ID NOs: 29-47. In various embodiments, the isolated antagonistic antigen binding protein comprises an antibody which comprises the amino acid sequence encoding the heavy chain of SEQ ID NO: 51 and the amino acid sequence encoding the light chain of SEQ ID NO: 52.

In various embodiments, the present disclosure comprises a method for treating or preventing heart failure and associated conditions in a subject, comprising administering to a subject diagnosed with heart failure, or a subject at risk of developing heart failure, a therapeutically effective amount of an isolated antagonistic antigen binding protein that specifically binds to the human glucagon receptor; and (b) a second agent composition. In various embodiments, the second agent composition is selected from a group consisting of: angiotensin-converting enzyme (ACE) inhibitors, β-adrenergic blocking agents, angiotension II receptor blockers (ARBs), diuretics, and digitalis. In various embodiments, the isolated antagonistic antigen binding protein comprises an antibody which comprises the amino acid sequence encoding the heavy chain of SEQ ID NO: 51 and the amino acid sequence encoding the light chain of SEQ ID NO: 52.

In various embodiments, the present disclosure comprises a method for treating or preventing diabetes induced cardiomyopathy in a subject, comprising administering to a subject diagnosed with diabetes, or a subject at risk of developing diabetes, a therapeutically effective amount of an isolated antagonistic antigen binding protein that specifically binds to the human glucagon receptor; and (b) a second agent composition. In various embodiments, the second agent composition is selected from a group consisting of: angiotensin-converting enzyme (ACE) inhibitors, β-adrenergic blocking agents, angiotension II receptor blockers (ARBs), diuretics, and digitalis. In various embodiments, the isolated antagonistic antigen binding protein comprises an antibody which comprises the amino acid sequence encoding the heavy chain of SEQ ID NO: 51 and the amino acid sequence encoding the light chain of SEQ ID NO: 52.

In various embodiments, the isolated antagonistic antigen binding protein that specifically binds the human glucagon receptor will be admixed with a pharmaceutically acceptable carrier to form a pharmaceutical composition that can be systemically administered to the subject via intravenous injection, intramuscular injection, subcutaneous injection, intraperitoneal injection, transdermal injection, intra-arterial injection, intrasternal injection, intrathecal injection, intraventricular injection, intraurethral injection, intracranial injection, intrasynovial injection or via infusions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE(S) FOR CARRYING OUT THE INVENTION

Figure 1:
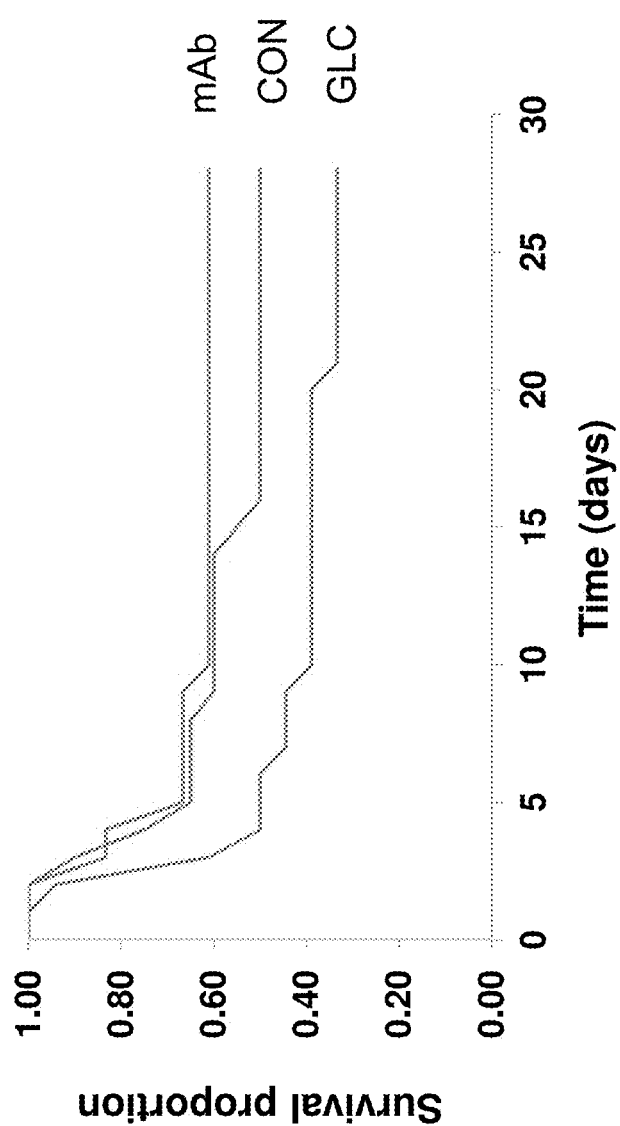
FIG. 1 is a line plot depicting the in vivo effects on mortality for the control (CON) group (n=18), REMD2.59 (mAb) treated group (n=18), and glucagon (GLC) treated group (n=28) throughout a 28 day study wherein myocardial infarction (MI) was induced in 54 C57BL6 male mice. Survival proportion is plotted vs. time (days).

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present disclosure are generally performed according to conventional methods well known in the art and as described in various general and more specific references that are cited and discussed throughout the present specification unless otherwise indicated. See, e.g., Green and Sambrook et al. Molecular Cloning: A Laboratory Manual, 4th ed., Cold Spring Harbor Laboratory Press, Cold Spring Harbor, N.Y. (2012) incorporated herein by reference, and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Definitions

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. In certain embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "therapeutic protein" refers to proteins, polypeptides, antibodies, peptides or fragments or variants thereof, having one or more therapeutic and/or biological activities. Therapeutic proteins encompassed by the invention include but are not limited to, proteins, polypeptides, peptides, antibodies, and biologics. (The terms peptides, proteins, and polypeptides are used interchangeably herein.) It is specifically contemplated that the term "Therapeutic protein" encompasses antibodies and fragments and variants thereof.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described by explaining how it differs from a reference sequence.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W)

A "non-conservative amino acid substitution" refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. Exemplary amino acid substitutions are set forth in Table 1.

TABLE 1

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |

TABLE 1-continued

| Original Residues | Exemplary Substitutions | Preferred Substitutions |
|---|---|---|
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In certain embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. (Id).

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. A substantially pure polypeptide or protein will typically comprise about 50%, 60%, 70%, 80% or 90% W/W of a protein sample, more usually about 95%, and e.g., will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

An "antigen binding and antagonizing protein" is a protein comprising a portion that binds to an antigen and, optionally, a scaffold or framework portion that allows the antigen binding portion to adopt a conformation that promotes binding of the isolated antagonistic antigen binding protein to the antigen. Examples of antigen binding and antagonizing proteins include antibodies, antibody fragments (e.g., an antigen binding portion of an antibody), antibody derivatives, and antibody analogs. The isolated antagonistic antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the isolated antagonistic antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129 (2003); Roque et al., Biotechnol. Prog. 20:639-654 (2004). In addition, peptide antibody mimetics ("PAMs") can be used, as well as scaffolds based on antibody mimetics utilizing fibronection components as a scaffold.

An isolated antagonistic antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

An "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

A Fab fragment is a monovalent fragment having the $V_L$, $V_H$, $C_L$ and $C_{H1}$ domains; a $F(ab')_2$ fragment is a bivalent fragment having two Fab fragments linked by a disulfide bridge at the hinge region; a Fd fragment has the $V_H$ and C.sub.H1 domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An isolated antagonistic antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

An isolated antagonistic antigen binding protein of the present disclosure, including an antibody, "specifically binds" to an antigen, such as the human glucagon receptor if it binds to the antigen with a high binding affinity as determined by a dissociation constant (Kd, or corresponding Kb, as defined below) value of $10^{-7}$ M or less. An isolated antagonistic antigen binding protein that specifically binds to the human glucagon receptor may be able to bind to glucagon receptors from other species as well with the same or different affinities.

An "epitope" is the portion of a molecule that is bound by an isolated antagonistic antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding and antagonizing protein).

The term "blood glucose level", or "level of blood glucose" shall mean blood glucose concentration. In certain embodiments, a blood glucose level is a plasma glucose level. Plasma glucose may be determined in accordance with, e.g., Etgen et al., Metabolism, 49(5): 684-688, 2000) or calculated from a conversion of whole blood glucose concentration in accordance with D'Orazio et al., Clin. Chem. Lab. Med., 44(12):1486-1490, 2006.

The term "normal glucose levels" refers to mean plasma glucose values in humans of less than about 100 mg/dL for fasting levels, and less than about 145 mg/dL for 2-hour post-prandial levels or 125 mg/dL for a random glucose. The term "elevated blood glucose level" or "elevated levels of blood glucose" shall mean an elevated blood glucose level such as that found in a subject demonstrating clinically inappropriate basal and postprandial hyperglycemia or such as that found in a subject in oral glucose tolerance test (oGTT), with "elevated levels of blood glucose" being greater than about 100 mg/dL when tested under fasting conditions, and greater than about 200 mg/dL when tested at 1 hour.

The terms "glucagon inhibitor", "glucagon suppressor" and "glucagon antagonist" are used interchangeably. Each is a molecule that detectably inhibits glucagon signaling. The inhibition caused by an inhibitor need not be complete so long as the inhibition is detectable using an assay that is recognized and understood in the art as being determinative of glucagon signaling inhibition.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

A "pharmaceutical composition" refers to a composition suitable for pharmaceutical use in an animal or human. A pharmaceutical composition comprises a pharmacologically and/or therapeutically effective amount of an active agent and a pharmaceutically acceptable carrier. "Pharmaceutically acceptable carrier" refers to compositions that do not produce adverse, allergic, or other untoward reactions when administered to an animal or a human. As used herein "pharmaceutically acceptable carrier" refers to any of the standard pharmaceutical carriers, vehicles, buffers, and carriers, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The term "immunoconjugate" or "fusion protein" as used herein refers to a molecule comprising an antibody or antigen-binding fragment thereof conjugated (or linked) directly or indirectly to an effector molecule. The effector molecule can be a detectable label, an immunotoxin, cytokine, chemokine, therapeutic agent, or chemotherapeutic agent. The antibody or antigen-binding fragment thereof may be conjugated to an effector molecule via a peptide linker. An immunoconjugate and/or fusion protein retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate may also be referred to as an antibody drug conjugate (ADC). Because immunoconjugates and/or fusion proteins are originally prepared from two molecules with separate functionalities, such as an antibody and an effector molecule, they are also sometimes referred to as "chimeric molecules."

As used herein, a "therapeutically effective amount" of an isolated antagonistic antigen binding protein that specifically binds the human glucagon receptor refers to an amount of such protein that, when provided to a subject in accordance with the disclosed and claimed methods effects one of the following biological activities: treats heart failure; or reduces, suppresses, attenuates, or inhibits one or more symptoms of heart failure.

The terms "treat", "treating" and "treatment" refer refers to an approach for obtaining beneficial or desired clinical results. Further, references herein to "treatment" include references to curative, palliative and prophylactic treatment. For purposes of this disclosure, beneficial or desired clinical results include, but are not limited to, one or more of the following: improvement in blood glucose to within about 80-180 mg/dL, or to within about 80-170 mg/dL, or to within about 80-160 mg/dL, or to within about 80-150 mg/dL, or to within about 80-140 mg/dL, or an improvement in any one or more conditions, diseases, or symptoms associated with, or resulting from, elevated levels of blood glucose including, but not limited to, hyperglycemia, hyperglucanemia, and hyperinsulinemia.

It is understood that aspects and embodiments of the invention described herein include "consisting" and/or "consisting essentially of" aspects and embodiments.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

Reference to "about" a value or parameter herein includes (and describes) variations that are directed to that value or parameter per se. For example, description referring to "about X" includes description of "X".

Glucagon Receptor and Antigen Binding and Antagonizing Proteins

Glucagon is a 29 amino acid hormone processed from its pre-pro-form in the pancreatic alpha cells by cell specific expression of prohormone convertase 2 (PC2), a neuroendocrine-specific protease involved in the intracellular maturation of prohormones and proneuropeptides (Furuta et al., J. Biol. Chem. 276: 27197-27202 (2001)). In vivo, glucagon is a major counter-regulatory hormone for insulin actions. During fasting, glucagon secretion increases in response to falling glucose levels. Increased glucagon secretion stimulates glucose production by promoting hepatic glycogenolysis and gluconeogenesis (Dunning and Gerich, Endocrine Reviews, 28:253-283 (2007)). Thus glucagon counterbalances the effects of insulin in maintaining normal levels of glucose in animals.

The biological effects of glucagon are mediated through the binding and subsequent activation of a specific cell surface receptor, the glucagon receptor. The glucagon receptor (GCGR) is a member of the secretin subfamily (family B) of G-protein-coupled receptors. The human GCGR is a 477 amino acid sequence GPCR and the amino acid sequence of GCGR is highly conserved across species (Mayo et al, Pharmacological Rev., 55:167-194, (2003)). The glucagon receptor is predominantly expressed in the liver, where it regulates hepatic glucose output, on the kidney, and on islet β-cells, reflecting its role in gluconeogenesis. The activation of the glucagon receptors in the liver stimulates the activity of adenyl cyclase and phosphoinositol turnover which subsequently results in increased expression of gluconeogenic enzymes including phosphoenolpyruvate carboxykinase (PEPCK), fructose-1,6-bisphosphatase (FBPase-1), and glucose-6-phosphatase (G-6-Pase). In addition, glucagon signaling activates glycogen phosphorylase and inhibits glycogen synthase. Studies have shown that higher basal glucagon levels and lack of suppression of postprandial glucagon secretion contribute to diabetic conditions in humans (Muller et al., N Eng J Med 283: 109-115 (1970)). As such, methods of controlling and lowering blood glucose by targeting glucagon production or function using a GCGR antagonist have been explored.

In various embodiments, the antigen binding and antagonizing proteins of the present disclosure may be selected to bind to membrane-bound glucagon receptors as expressed on cells, and inhibit or block glucagon signaling through the glucagon receptor. In various embodiments, the antigen binding and antagonizing proteins of the present disclosure specifically bind to the human glucagon receptor. In various embodiments, the antigen binding and antagonizing proteins binding to the human glucagon receptor may also bind to the glucagon receptors of other species. The polynucleotide and polypeptide sequences for several species of glucagon receptor are known (see, e.g., U.S. Pat. No. 7,947,809, herein incorporated by reference in its entirety for its specific teaching of polynucleotide and polypeptide sequences of a human, rat, mouse and cynomolgus glucagon receptor). In various embodiments of the present disclosure, the antigen binding and antagonizing proteins specifically bind the human glucagon receptor having the amino acid sequence set forth in SEQ ID NO: 1:

```
Glucagon Receptor Human (Homo sapiens)
amino acid sequence (Accession Number AAI04855)
                                        (SEQ ID NO: 1)
MPPCQPQRPLLLLLLLLACQPQVPSAQVMDFLFEKWKLYGDQCHHNLSLL

PPPTELVCNRTFDKYSCWPDTPANTTANISCPWYLPWHHKVQHRFVFKRC

GPDGQWVRGPRGQPWRDASQCQMDGEEIEVQKEVAKMYSSFQVMYTVGYS

LSLGALLLALAILGGLSKLHCTRNAIHANLFASFVLKASSVLVIDGLLRT

RYSQKIGDDLSVSTWLSDGAVAGCRVAAVFMQYGIVANYCWLLVEGLYLH

NLLGLATLPERSFFSLYLGIGWGAPMLFVVPWAVVKCLFENVQCWTSNDN

MGFWWILRFPVFLAILINFFIFVRIVQLLVAKLRARQMHHTDYKFRLAKS

TLTLIPLLGVHEVVFAFVTDEHAQGTLRSAKLFFDLFLSSFQGLLVAVLY

CFLNKEVQSELRRRWHRWRLGKVLWEERNTSNHRASSSPGHGPPSKELQF

GRGGGSQDSSAETPLAGGLPRLAESPF
```

In various embodiments, the antigen binding and antagonizing proteins of the present disclosure specifically bind glucagon receptors which have at least 70%, at least 75%, at least 80%, at least 85%, at least 90%, at least 95%, at least 96%, at least 97%, at least 98%, or at least 99% identity (as calculated using methods known in the art and described herein) to the glucagon receptors described in the cited references are also included in the present disclosure.

The antigen binding and antagonizing proteins of the present disclosure function to block the interaction between glucagon and its receptor, thereby inhibiting the glucose elevating effects of glucagon. As such, the use of the antigen binding and antagonizing proteins of the present disclosure are an effective means of achieving normal levels of glucose, thereby ameliorating, or preventing one or more symptoms of, or long term complications caused by diabetes including, but not limited to, hyperglycemia, hyperglucanemia, and hyperinsulinemia. The use of the antigen binding and antagonizing proteins of the present disclosure are also an effective means of achieving normal levels of glucose in non-diabetic patients, thereby lowering the risk of hyperglycemia, hyperglucanemia, and hyperinsulinemia in subjects having disorders including, but not limited to, T1 D, T2D, obesity, NAFLD, NASH, and for treating such non-diabetic disorders. The present disclosure is based in part on the inventors' unique insight that isolated antigen binding and antagonizing proteins that specifically bind to the human glucagon receptor may provide for improved, effective therapies for treatment and prevention of heart failure after myocardial infarction. The present inventor proposes that the beneficial therapeutic effects provided by blocking the glucagon receptor in myocardial infarction-induced heart failure subjects (or all other heart failure subjects) relate to the prevention or attenuation of left ventricular (LV) remodeling which may include: increasing fractional shortening (FS), decreasing LV dilation (LVESD); preserving LV wall thickness; increasing LV developed pressure and ventricular contractility; decreasing the ratio of heart weight to body weight (infarct size); reducing the fibrosis process; reducing levels of incompletely oxidized fatty acid metabolites in the heart under ischemic conditions; and reducing MI-induced mortality rate.

Methods of generating antibodies that bind to antigens such as the human glucagon receptor are known to those skilled in the art. For example, a method for generating a monoclonal antibody that binds specifically to a targeted antigen polypeptide may comprise administering to a mouse an amount of an immunogenic composition comprising the targeted antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the targeted antigen polypeptide. Once obtained, a hybridoma can be propagated in a cell culture, optionally in culture conditions where the hybridoma-derived cells produce the monoclonal antibody that binds specifically to targeted antigen polypeptide. The monoclonal antibody may be purified from the cell culture. A variety of different techniques are then available for testing an antigen/antibody interaction to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl.

Acad. Sci. (U.S.A.), 90: 2551-2555, 1993; Jakobovits et al., Nature, 362: 255-258, 1993; Lonberg et al., U.S. Pat. No. 5,545,806; and Surani et al., U.S. Pat. No. 5,545,807.

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al., Science, 240:1041-1043, 1988; Liu et al., Proc. Natl. Acad. Sci. (U.S.A.), 84:3439-3443, 1987; Liu et al., J. Immunol., 139:3521-3526, 1987; Sun et al., Proc. Natl. Acad. Sci. (U.S.A.), 84:214-218, 1987; Nishimura et al., Canc. Res., 47:999-1005, 1987; Wood et al., Nature, 314:446-449, 1985; and Shaw et al., J. Natl Cancer Inst., 80:1553-1559, 1988).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. (U.S.A.), 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-GCGR antibody or antigen binding antibody fragment thereof comprises the steps of synthesizing a library of human antibodies on phage, screening the library with GCGR or an antibody binding portion thereof, isolating phage that bind GCGR, and obtaining the antibody from the phage. By way of another example, one method for preparing the library of antibodies for use in phage display techniques comprises the steps of immunizing a non-human animal comprising human immunoglobulin loci with GCGR or an antigenic portion thereof to create an immune response, extracting antibody-producing cells from the immunized animal; isolating RNA encoding heavy and light chains of antibodies of the disclosure from the extracted cells, reverse transcribing the RNA to produce cDNA, amplifying the cDNA using primers, and inserting the cDNA into a phage display vector such that antibodies are expressed on the phage. Recombinant anti-GCGR antibodies of the disclosure may be obtained in this way.

Again, by way of example, recombinant human anti-GCGR antibodies of the disclosure can also be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology, 9:1370-1372 (1991); Hay et al., Hum. Antibod. Hybridomas, 3:81-85, 1992; Huse et al., Science, 246:1275-1281, 1989; McCafferty et al., Nature, 348:552-554, 1990; Griffiths et al., EMBO J., 12:725-734, 1993; Hawkins et al., J. Mol. Biol., 226:889-896, 1992; Clackson et al., Nature, 352:624-628, 1991; Gram et al., Proc. Natl. Acad. Sci. (U.S.A.), 89:3576-3580, 1992; Garrad et al., Bio/Technology, 9:1373-1377, 1991; Hoogenboom et al., Nuc. Acid Res., 19:4133-4137, 1991; and Barbas et al., Proc. Natl. Acad. Sci. (U.S.A.), 88:7978-7982, 1991), all incorporated herein by reference.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics, 7:13-21, 1994 and U.S. Pat. Nos. 5,916,771, 5,939,598, 5,985,615, 5,998,209, 6,075,181, 6,091,001, 6,114,598, 6,130,364, 6,162,963 and 6,150,584. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse™ mice further contain approximately all of the human lambda light chain locus. See Mendez et al., Nature Genetics, 15:146-156, 1997; Green and Jakobovits, J. Exp. Med., 188:483-495, 1998; and WO 98/24893.

In various embodiments, the isolated antagonistic antigen binding protein of the present disclosure utilize an antibody or antigen binding antibody fragment thereof is a polyclonal antibody, a monoclonal antibody or antigen-binding fragment thereof, a recombinant antibody, a diabody, a chimerized or chimeric antibody or antigen-binding fragment thereof, a humanized antibody or antigen-binding fragment thereof, a fully human antibody or antigen-binding fragment thereof, a CDR-grafted antibody or antigen-binding fragment thereof, a single chain antibody, an Fv, an Fd, an Fab, an Fab', or an F(ab')$_2$, and synthetic or semi-synthetic antibodies.

In various embodiments, the isolated antagonistic antigen binding protein of the present disclosure utilize an antibody or antigen-binding fragment that binds to an immune-checkpoint protein antigen with a dissociation constant ($K_D$) of, e.g., at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M. In various embodiments, the isolated antagonistic antigen binding protein of the present disclosure utilize an antibody or antigen-binding fragment that binds to an immune-checkpoint protein antigen with a dissociation constant ($K_D$) in the range of, e.g., at least about $1\times10^{-7}$ M to at least about $1\times10^{-8}$ M, at least about $1\times10^{-8}$ M to at least about $1\times10^{-9}$ M, at least about $1\times10^{-9}$ M to at least about $1\times10^{-10}$ M, at least about $1\times10^{-10}$ M to at least about $1\times10^{-11}$ M, or at least about $1\times10^{-11}$ M to at least about $1\times10^{-12}$ M.

In various embodiments of the present invention, the isolated antagonistic antigen binding protein is an anti-GCGR ("antagonistic") antibody or antigen-binding fragment which comprises the polynucleotide and polypeptide sequences set forth in, e.g., U.S. Pat. Nos. 8,158,759, 5,770,445, 7,947,809, 7,968,686, 8,545,847, and 8,771,696; U.S. patent publications 2009/0041784; 2009/0252727; 2013/0344538 and 2014/0335091; and PCT publication WO2008/036341, each herein incorporated by reference in its entirety for its specific teaching of polynucleotide and polypeptide sequences of various anti-GCGR antibodies or antigen-binding fragments. In various embodiments of the present invention, the isolated antagonistic antigen binding protein is any biosimilar, biogeneric, follow-on biologic, or follow-on protein version of any anti-GCGR antibody described in the art.

In various embodiments of the present disclosure the antibody may be an anti-GCGR antibody that has the same or higher antigen-binding affinity as that of the antibody comprising the heavy chain variable region sequence as set forth in SEQ ID NO: 2. In various embodiments, the antibody may be an anti-GCGR antibody which binds to the same epitope as the antibody comprising the heavy chain variable region sequence as set forth in SEQ ID NO: 2. In various embodiments, the antibody is an anti-GCGR antibody which competes with the antibody comprising the heavy chain variable region sequence as set forth in SEQ ID NO: 2. In various embodiments, the antibody may be an anti-GCGR antibody which comprises at least one (such as two or three) CDRs of the heavy chain variable region sequence as set forth in SEQ ID NO: 2. In various embodiments, the antibody may be an anti-GCGR antibody having a sequence identical, substantially identical or substantially similar to SEQ ID NO: 2. In various embodiments, the antibody may be an anti-GCGR antibody which comprises the heavy chain variable region sequence as set forth in SEQ ID NO: 2:

(SEQ ID NO: 2)
QVQLVESGGGVVQPGRSLRLSCAASGFTFSSYGMHWVRQAPGKGLEWVAV

MWYDGSNKDYVDSVKGRFTISRDNSKNTLYLQMNRLRAEDTAVYYCAREK

DHYDILTGYN YYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 3. In various embodiments, the antibody may be an anti-GCGR antibody which binds to the same epitope as the antibody comprising the light chain variable region sequence as set forth in SEQ ID NO: 3. In various embodiments, the antibody is an anti-GCGR antibody which competes with the antibody comprising the light chain variable region sequence as set forth in SEQ ID NO: 3. In various embodiments, the antibody may be an anti-GCGR antibody which comprises at least one (such as two or three) CDRs of the light chain variable region sequence as set forth in SEQ ID NO: 3. In various embodiments, the antibody may be an anti-GCGR antibody having a sequence identical, substantially identical or substantially similar to SEQ ID NO: 3. In various embodiments, the antibody may be an anti-GCGR antibody which comprises the light chain variable region sequence as set forth in SEQ ID NO: 3:

(SEQ ID NO: 3)
DIQMTQSPSSLSASVGDRVTITCRASQGIRNDLGWYQQKPGKAPKRLIYA

ASSLQSGVPSRFSGSGSGTEFTLTISSVQPEDFVTYYCLQHNSNPLTFGG

GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 2 or 3.

In various embodiments of the present disclosure the antibody may be an anti-GCGR antibody that has the same or higher antigen-binding affinity as that of the antibody comprising the heavy chain variable region sequence as set forth in SEQ ID NO: 4. In various embodiments, the antibody may be an anti-GCGR antibody which binds to the same epitope as the antibody comprising the heavy chain variable region sequence as set forth in SEQ ID NO: 4. In various embodiments, the antibody is an anti-GCGR antibody which competes with the antibody comprising the heavy chain variable region sequence as set forth in SEQ ID NO: 4. In various embodiments, the antibody may be an anti-GCGR antibody which comprises at least one (such as two or three) CDRs of the heavy chain variable region sequence as set forth in SEQ ID NO: 4. In various embodiments, the antibody may be an anti-GCGR antibody having a sequence identical, substantially identical or substantially similar to SEQ ID NO: 4. In various embodiments, the antibody may be an anti-GCGR antibody which comprises the heavy chain variable region sequence as set forth in SEQ ID NO: 4:

(SEQ ID NO: 4)
QVQLVESGGGVVQPGRSLRLSCAASGFTFSSYGMHWVRQAPGKGLEWVAV

MWYDGSNKDYVDSVKGRFTISRDNSKNTLYLQMNSLRAEDTAVYYCAREK

DHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 5. In various embodiments, the antibody may be an anti-GCGR antibody which binds to the same epitope as the antibody comprising the light chain variable region sequence as set forth in SEQ ID NO: 5. In various embodiments, the antibody is an anti-GCGR antibody which competes with the antibody comprising the light chain variable region sequence as set forth in SEQ ID NO: 5. In various embodiments, the antibody may be an anti-GCGR antibody which comprises at least one (such as two or three) CDRs of the light chain variable region sequence as set forth in SEQ ID NO: 5. In various embodiments, the antibody may be an anti-GCGR antibody having a sequence identical, substantially identical or substantially similar to SEQ ID NO: 5. In various embodiments, the antibody may be an anti-GCGR antibody which comprises the light chain variable region sequence as set forth in SEQ ID NO: 5:

(SEQ ID NO: 5)
DIQMTQSPSSLSASVGDRVTITCRASQGIRNDLGWYQQKPGKAPKRLIYA

ASSLQSGVPSRFSGSGSGTEFTLTISSLQPEDFVTYYCLQHNSNPLTFGG

GTKVEIK

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 4 or 5.

In various embodiments of the present disclosure the antibody may be an anti-GCGR antibody that has the same or higher antigen-binding affinity as that of the antibody comprising the heavy chain variable region sequence as set forth in SEQ ID NO: 6. In various embodiments, the antibody may be an anti-GCGR antibody which binds to the same epitope as the antibody comprising the heavy chain variable region sequence as set forth in SEQ ID NO: 6. In various embodiments, the antibody is an anti-GCGR antibody which competes with the antibody comprising the heavy chain variable region sequence as set forth in SEQ ID NO: 6. In various embodiments, the antibody may be an anti-GCGR antibody which comprises at least one (such as two or three) CDRs of the heavy chain variable region sequence as set forth in SEQ ID NO: 6. In various embodiments, the antibody may be an anti-GCGR antibody having a sequence identical, substantially identical or substantially similar to SEQ ID NO: 6. In various embodiments, the antibody may be an anti-GCGR antibody which comprises the heavy chain variable region sequence as set forth in SEQ ID NO: 6:

(SEQ ID NO: 6)
QVQLVESGGGVVQPGRSLRLSCAASGFTFSSYGMHWVRQAPGKGLEWVA

VMWYDGSNKDYVDSVKGRFTISRDNSKNTLYLQMNRLRAEDTAVYYCAR

EKDHYDILTGYNYYYGLDVWGQGTTVTVSS

In various embodiments of the present disclosure the antibody may be an anti-GCGR antibody that has the same or higher antigen-binding affinity as that of the antibody comprising the light chain variable region sequence as set forth in SEQ ID NO: 7. In various embodiments, the antibody may be an anti-GCGR antibody which binds to the same epitope as the antibody comprising the light chain variable region sequence as set forth in SEQ ID NO: 7. In various embodiments, the antibody is an anti-GCGR antibody which competes with the antibody comprising the light chain variable region sequence as set forth in SEQ ID NO: 7. In various embodiments, the antibody may be an anti-GCGR antibody which comprises at least one (such as two or three) CDRs of the light chain variable region sequence as set forth in SEQ ID NO: 7. In various embodiments, the antibody may be an anti-GCGR antibody having a sequence identical, substantially identical or substantially similar to SEQ ID NO: 7. In various embodiments, the antibody may be an anti-GCGR antibody which comprises the light chain variable region sequence as set forth in SEQ ID NO: 7:

```
                                            (SEQ ID NO: 7)
DIQMTQSPSSLSASVGDRVTITCRASQGIRNDLGWYQQKPGKAPKRLIYA

ASSLESGVPSRFSGSGSGTEFTLTISSVQPEDFVTYYCLQHNSNPLTFGG

GTKVEIK
```

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 6 or 7.

In various embodiments of the present disclosure the antibody may be an anti-GCGR antibody that has the same or higher antigen-binding affinity as that of the chimeric antibody comprising the heavy chain sequence as set forth in SEQ ID NO: 8. In various embodiments, the antibody may be an anti-GCGR antibody which binds to the same epitope as the antibody comprising the heavy chain sequence as set forth in SEQ ID NO: 8. In various embodiments, the antibody is an anti-GCGR antibody which competes with the antibody comprising the heavy chain sequence as set forth in SEQ ID NO: 8. In various embodiments, the antibody may be an anti-GCGR antibody which comprises at least one (such as two or three) CDRs of the heavy chain sequence as set forth in SEQ ID NO: 8. In various embodiments, the antibody may be an anti-GCGR antibody having a sequence identical, substantially identical or substantially similar to SEQ ID NO: 8. In various embodiments, the antibody may be an anti-GCGR antibody which comprises the heavy chain sequence as set forth in SEQ ID NO: 8:

```
                                            (SEQ ID NO: 8)
MEFGLSWVFLVALLRGVQCQVQLVESGGGVVQPGRSLRLSCAASGFTFSS

YGMHWVRQAPGKGLEWVAVMWYDGSNKDYVDSVKGRFTISRDNSKNTLYL

QMNRLRAEDTAVYYCAREKDHYDILTGYNYYYGLDVWGQGTTVTVSSAKT

TPPSVYPLAPGSAAQTNSMVTLGCLVKGYFPEPVTVTWNSGSLSSGVHTF

PAVLQSDLYTLSSSVTVPSSTWPSETVTCNVAHPASSTKVDKKIVPRDCG

CKPCICTVPEVSSVFIFPPKPKDVLTITLTPKVTCVVVDISKDDPEVQFS

WFVDDVEVHTAQTQPREEQFNSTFRSVSELPIMHQDWLNGKEFKCRVNSA

-continued
AFPAPIEKTISKTKGRPKAPQVYTIPPPKEQMAKDKVSLTCMITDFFPED

ITVEWQWNGQPAENYKNTQPIMDTDGSYFVYSKLNVQKSNWEAGNTFTCS

VLHEGLHNHHTEKSLSHSPGK
```

In various embodiments of the present disclosure the antibody may be an anti-GCGR antibody that has the same or higher antigen-binding affinity as that of the chimeric antibody comprising the light chain sequence as set forth in SEQ ID NO: 9. In various embodiments, the antibody may be an anti-GCGR antibody which binds to the same epitope as the antibody comprising the light chain sequence as set forth in SEQ ID NO: 9. In various embodiments, the antibody is an anti-GCGR antibody which competes with the antibody comprising the light chain sequence as set forth in SEQ ID NO: 9. In various embodiments, the antibody may be an anti-GCGR antibody which comprises at least one (such as two or three) CDRs of the light chain sequence as set forth in SEQ ID NO: 9. In various embodiments, the antibody may be an anti-GCGR antibody having a sequence identical, substantially identical or substantially similar to SEQ ID NO: 9. In various embodiments, the antibody may be an anti-GCGR antibody which comprises the light chain sequence as set forth in SEQ ID NO: 9:

```
                                            (SEQ ID NO: 9)
MDMRVPAQLLGLLLLWFPGARCDIQMTQSPSSLSASVGDRVTITCRASQG

IRNDLGWYQQKPGKAPKRLIYAASSLESGVPSRFSGSGSGTEFTLTISSV

QPEDFVTYYCLQHNSNPLTFGGGTKVEIKRADAAPTVSIFPPSSEQLTSG

GASVVCFLNNFYPKDINVKWKIDGSERQNGVLNSWTDQDSKDSTYSMSST

LTLTKDEYERHNSYTCEATHKTSTSPIVKSFNRNEC
```

In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 8 or 9.

In various embodiments of the present disclosure the antibody may be an anti-GCGR antibody which comprises a heavy chain variable region sequence identical, substantially identical or substantially similar to a sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28 and a light chain variable region sequence identical, substantially identical or substantially similar to a sequence selected from SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47. In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with the sequences of SEQ ID NOS: 10-28 or SEQ ID NOS: 29-47.

Examples of Anti-GCGR Antibodies

| HCVR | LCVR |
| --- | --- |
| SEQ ID NO: 2 | SEQ ID NO: 3 |
| SEQ ID NO: 4 | SEQ ID NO: 5 |
| SEQ ID NO: 6 | SEQ ID NO: 7 |
| SEQ ID NO: 10 | SEQ ID NO: 29 |
| SEQ ID NO: 11 | SEQ ID NO: 30 |
| SEQ ID NO: 12 | SEQ ID NO: 31 |
| SEQ ID NO: 13 | SEQ ID NO: 32 |
| SEQ ID NO: 14 | SEQ ID NO: 33 |
| SEQ ID NO: 15 | SEQ ID NO: 34 |
| SEQ ID NO: 16 | SEQ ID NO: 35 |
| SEQ ID NO: 17 | SEQ ID NO: 36 |
| SEQ ID NO: 18 | SEQ ID NO: 37 |
| SEQ ID NO: 19 | SEQ ID NO: 38 |
| SEQ ID NO: 20 | SEQ ID NO: 39 |
| SEQ ID NO: 21 | SEQ ID NO: 40 |
| SEQ ID NO: 22 | SEQ ID NO: 41 |
| SEQ ID NO: 23 | SEQ ID NO: 42 |
| SEQ ID NO: 24 | SEQ ID NO: 43 |
| SEQ ID NO: 25 | SEQ ID NO: 44 |
| SEQ ID NO: 26 | SEQ ID NO: 45 |
| SEQ ID NO: 27 | SEQ ID NO: 46 |
| SEQ ID NO: 28 | SEQ ID NO: 47 |

An isolated anti-GCGR antibody, antibody fragment, or antibody derivative of the present disclosure can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In various embodiments, an isolated antigen binding protein of the present disclosure comprises the constant light chain kappa region as set forth in SEQ ID NO: 48, or a fragment thereof. In various embodiments, an isolated antigen binding protein of the present disclosure comprises the constant light chain lambda region as set forth in SEQ ID NO: 49, or a fragment thereof. In various embodiments, an isolated antigen binding protein of the present disclosure comprises a IgG2 heavy chain constant region set forth in SEQ ID NO: 50, or a fragment thereof.

In various embodiments, an isolated antagonistic antigen binding protein of the present disclosure is a fully human anti-GCGR antibody that comprises a heavy chain sequence identical, substantially identical or substantially similar to SEQ ID NO: 51 and a light chain sequence identical, substantially identical or substantially similar to SEQ ID NO: 52. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

In various embodiments of the present disclosure, the isolated antagonistic antigen binding protein is a hemibody. A "hemibody" is an immunologically-functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In various embodiments, the hemibody is a monovalent antigen binding protein comprising (i) an intact light chain, and (ii) a heavy chain fused to an Fc region (e.g., an IgG2 Fc region). Methods for preparing hemibodies are described in, e.g., U.S. patent application 2012/0195879, herein incorporated by reference in its entirety herein for purposes of teaching the preparation of such hemibodies.

Pharmaceutical Compositions

In another aspect, the present disclosure provides a pharmaceutical composition comprising an isolated antagonistic antigen binding protein as described herein, with one or more pharmaceutically acceptable carrier(s). The pharmaceutical compositions and methods of uses described herein also encompass embodiments of combinations (co-administration) with other active agents, as detailed below.

Generally, the antagonistic antigen binding proteins of the present disclosure are suitable to be administered as a formulation in association with one or more pharmaceutically acceptable carrier(s). The term 'carrier' is used herein to describe any ingredient other than the compound(s) of the disclosure. The choice of carrier(s) will to a large extent depend on factors such as the particular mode of administration, the effect of the carrier on solubility and stability, and the nature of the dosage form. As used herein, "pharmaceutically acceptable carrier" includes any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, the composition will include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present disclosure and methods for their preparation will be readily apparent to those skilled in the art. Such compositions and methods for their preparation may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration.

The pharmaceutical compositions of the present disclosure are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have been described in the literature and are commercially available.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain carriers such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the isolated antagonistic antigen binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The isolated antagonistic antigen binding protein of the present disclosure can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops.

The pressurized container, pump, spray, atomizer, or nebulizer generally contains a solution or suspension of an isolated antagonistic antigen binding protein of the disclosure comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the isolated antagonistic antigen binding protein of the disclosure, a suitable powder base and a performance modifier.

Suitable flavours, such as menthol and levomenthol, or sweeteners, such as saccharin or saccharin sodium, may be added to those formulations of the disclosure intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the disclosure are typically arranged to administer a metered dose or "puff" of an antibody of the disclosure. The overall daily dose will typically be administered in a single dose or, more usually, as divided doses throughout the day.

The isolated antagonistic antigen binding protein of the present disclosure may also be formulated for an oral administration. Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the isolated antagonistic antigen binding protein is mixed with at least one pharmaceutical carrier, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical carrier, and the solid formulation is placed in a capsular container suitable for delivery to the gastrointestinal tract. Compositions comprising isolated antagonistic antigen binding protein may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing isolated antagonistic antigen binding protein in admixture with non-toxic pharmaceutically acceptable carriers which are suitable for manufacture of tablets. These carriers may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the isolated antagonistic antigen binding protein is mixed with an inert solid diluent, for example, calcium carbonate, calcium phosphate, or kaolin or as soft gelatin capsules wherein the isolated antagonistic antigen binding protein is mixed with an aqueous or an oil medium, for example, *arachis* oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Any method for administering peptides, proteins or antibodies accepted in the art may suitably be employed for administering the isolated antagonistic antigen binding protein of the disclosure.

Methods of Treatment

Due to their interaction with the glucagon receptor, the present antigen binding and antagonizing proteins are useful for lowering blood glucose levels by regulating gluconeogenesis and glycogenlysis and also for the treatment of a wide range of conditions and disorders in which blocking the interaction of glucagon with its receptor is beneficial, while also reducing and or eliminating one or more of the unwanted side effects associated with the current treatments.

An antagonistic antigen binding protein, in particular a human antibody according to the present disclosure, need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the disclosure is directed to a method comprising administering to a subject an isolated antagonistic antigen binding protein such as a human antibody in an amount and for a time sufficient to induce a sustained improvement over baseline of an indicator that reflects the severity of the particular disorder.

Cardiovascular Diseases/Diabetic Cardiomyopathy/Heart Failure

Cardiovascular disease is a general name for a wide variety of diseases, disorders and conditions that affect the heart and/or blood vessels. Types of cardiovascular disease includes angina, heart attack (myocardial infarction), atherosclerosis, heart failure, cardiovascular disease, rheumatic heart disease, cardiac arrhythmias (abnormal heart rhythms), cerebrovascular disease, congenital heart defects, cardiomyopathy, left ventricular hypertrophy, right ventricular hypertrophy, post-infarction heart rupture, infections of the heart, coronary artery disease, peripheral arterial disease, renal artery stenosis, aortic aneurysm, myocardial diseases, heart valve disorders, myocarditis, and pericarditis.

Heart failure is a clinical syndrome characterized by the failure of the heart to pump sufficient blood to meet the body's systemic demands. The heart contracts and relaxes with each heartbeat—these phases are referred to as systole (the contraction phase) and diastole (the relaxation phase). Systolic heart failure (SHF) is characterized by low ejection fraction. In patients with diastolic heart failure (DHF), contraction may be normal but relaxation of the heart may be impaired. This impairment is generally caused by a stiffening of the ventricles. Such impairment is referred to as diastolic dysfunction and if severe enough to cause pulmonary congestion (increased pressure and fluid in the blood vessels of the lungs), diastolic heart failure. DHF patients differ from those patients with SHF, in that DHF patients may have a "normal" ejection fraction. However, because the ventricle doesn't relax normally, the pressure within the ventricle increases and the blood filling the ventricle exceeds what is "normal". People with certain types of cardiomyopathy may also have diastolic dysfunction. Left ventricular hypertrophy refers to a thickening of the left ventricle as a result of increased left ventricular load. Left ventricular hypertrophy can be a significant marker for cardiovascular disorders and most common complications include arrhythmias, heart failure, ischemic heart disease, and sudden death. Although left ventricular hypertrophy (LVH) increases naturally with age, it is more common in people who have high blood pressure or have other heart problems. Because LVH usually develops in response to hypertension, current treatment and prevention mainly includes managing hypertension. Typical diagnosis involves the use of echocardiograms (ECHO) and electrocardiograms (ECG).

In one aspect, the present disclosure comprises a method for treating or preventing heart failure in a subject, comprising administering to the subject a therapeutically effective amount of an isolated antagonistic antigen binding protein that specifically binds to the human glucagon receptor. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

In one aspect, the present disclosure comprises a method for treating post-myocardial infarction heart failure in a subject in need thereof comprising administering to the subject a therapeutically effective amount of an isolated antagonistic antigen binding protein that specifically binds to the human glucagon receptor. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

In one aspect, the present discloses comprises a method of treating lateral ventricular (LV) remodeling in a subject, comprising administering to a subject diagnosed with heart failure, or a subject at risk of contracting heart failure, a therapeutically effective amount of an isolated antagonistic antigen binding protein that specifically binds to the human glucagon receptor. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

Diabetic cardiomyopathy describes diabetes-associated changes in the structure and function of the myocardium that is not directly attributable to other confounding factors such as coronary artery disease (CAD) or hypertension. It has been reported that in many patients with type 2 diabetes, diabetes associated changes are amplified by the existence of these comorbidities, which likely will augment the development of left ventricular hypertrophy, increase the susceptibility of the heart to ischemic injury and increase the overall likelihood of developing heart failure (Boudina and Abel, Rev Endocr Metab Disord., 11(1): 31-39, 2010 March). Several mechanisms have been implicated in the pathogenesis of diabetic cardiomyopathy, and the mechanisms responsible for diabetic cardiomyopathy continue to be elucidated. Changes in myocardial structure, calcium signaling and metabolism are early defects that have been described mainly in animal models and may precede clinically manifest cardiac dysfunction (Id). Diabetic cardiomyopathy in humans is characterized by diastolic dysfunction (DD), which may precede the development of systolic dysfunction (SD).

Diabetic nephropathies are nerve damaging disorders that are a common serious complication of diabetes mellitus. There are four main types of diabetic neuropathy: peripheral, autonomic, radiculoplexus, and mononeuropathy. Individuals may have just one type or symptoms of several types. Most symptoms develop gradually, and problems may not be noticed until considerable damage has occurred. Prolonged exposure to high blood sugar can damage delicate nerve fibers, causing diabetic neuropathy. Accordingly, it may to possible to prevent diabetic neuropathy or slow its progress with tight blood sugar control.

In various embodiments, the present disclosure comprises a method for treating or preventing heart failure and associated conditions in a subject, comprising administering to a subject diagnosed with diabetes mellitus or a subject at risk of developing diabetes mellitus, a therapeutically effective amount of an isolated antagonistic antigen binding protein that specifically binds to the human glucagon receptor. In various embodiments, the isolated antagonistic antigen binding protein comprises an antibody which comprises the amino acid sequence encoding the heavy chain of SEQ ID NO: 51 and the amino acid sequence encoding the light chain of SEQ ID NO: 52.

In one aspect, the present disclosure comprises a method for treating diabetic cardiomyopathy in a subject in need thereof comprising administering to the subject a therapeutically effective amount of an isolated antagonistic antigen binding protein that specifically binds to the human glucagon receptor. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52.

An isolated antagonistic antigen binding protein that specifically binds the human glucagon receptor, in particular, the fully human antibodies of the disclosure, may be administered, e.g., once or more than once, at regular intervals over a period of time. In various embodiments, a fully human antibody is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the fully human antibody is administered until the subject manifests a medically relevant degree of improvement over baseline for the chosen indicator or indicators.

One example of therapeutic regimens provided herein comprise subcutaneous injection of an isolated antagonistic antigen binding protein once a week, or once every two weeks, at an appropriate dosage, to treat a condition in which blood glucose levels play a role. Weekly or monthly administration of isolated antagonistic antigen binding protein would be continued until a desired result is achieved, e.g., the subject's symptoms subside. Treatment may resume as needed, or, alternatively, maintenance doses may be administered.

A subject's levels of blood glucose may be monitored before, during and/or after treatment with an isolated antagonistic antigen binding protein such as a human antibody, to detect changes, if any, in their levels. For some disorders, the incidence of elevated blood glucose may vary according to such factors as the stage of the disease. Known techniques may be employed for measuring glucose levels. Glucagon levels may also be measured in the subject's blood using known techniques, for example, ELISA.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured by, e.g., HPLC or immunoassays using the anti-idiotypic antibodies specific to the therapeutic drug. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the isolated antagonistic antigen binding protein of the disclosure can be in the range of 0.5-1200 mg per subject, 0.5-1100 mg per subject, 0.5-1000 mg per subject, 0.5-900 mg per subject, 0.5-800 mg per subject, 0.5-700 mg per subject, 0.5-600 mg per subject, 0.5-500 mg per subject, 0.5-400 mg per subject, 0.5-300 mg per subject, 0.5-200 mg per subject, 0.5-100 mg per subject, 0.5-50 mg per subject, 1-1200 mg per subject, 1-1100 mg per subject, 1-1000 mg per subject, 1-900 mg per subject, 1-800 mg per subject, 1-700 mg per subject, 1-600 mg per subject, 1-500 mg per subject, 1-400 mg per subject, 1-300 mg per subject, 1-200 mg per subject, 1-100 mg per subject, or 1-50 mg per subject depending, of course, on the mode of administration. For example, an intravenous monthly dose can require about 1-1000 mg/subject. In certain embodiments, the isolated antagonistic antigen binding protein of the disclosure can be administered at about 1-200 mg per subject, 1-150 mg per subject or 1-100 mg per subject. The total monthly dose can be administered in single or divided doses and can, at the physician's discretion, fall outside of the typical ranges given herein.

An exemplary, non-limiting monthly dosing range for a therapeutically or prophylactically effective amount of an isolated antagonistic antigen binding protein of the disclosure can be 0.001 to 10 mg/kg, 0.001 to 9 mg/kg, 0.001 to 8 mg/kg, 0.001 to 7 mg/kg, 0.001 to 6 mg/kg, 0.001 to 5 mg/kg, 0.001 to 4 mg/kg, 0.001 to 3 mg/kg, 0.001 to 2 mg/kg, 0.001 to 1 mg/kg, 0.010 to 10 mg/kg, 0.010 to 9 mg/kg, 0.010 to 8 mg/kg, 0.010 to 7 mg/kg, 0.010 to 6 mg/kg, 0.010 to 5 mg/kg, 0.010 to 4 mg/kg, 0.010 to 3 mg/kg, 0.010 to 2 mg/kg, 0.010 to 1 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, 0.1 to 1 mg/kg, 1 to 10 mg/kg, 1 to 9 mg/kg, 1 to 8 mg/kg, 1 to 7 mg/kg, 1 to 6 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the condition to be ameliorated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 μg/ml, about 1 to 750 μg/ml, about 1 to 500 μg/ml, about 1 to 250 μg/ml, about 10 to 1000 μg/ml, about 10 to 750 μg/ml, about 10 to 500 μg/ml, about 10 to 250 μg/ml, about 20 to 1000 μg/ml, about 20 to 750 μg/ml, about 20 to 500 μg/ml, about 20 to 250 μg/ml, about 30 to 1000 μg/ml, about 30 to 750 μg/ml, about 30 to 500 μg/ml, about 30 to 250 μg/ml.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

In various embodiments, single or multiple administrations of the pharmaceutical compositions are administered depending on the dosage and frequency as required and tolerated by the subject. In any event, the composition should provide a sufficient quantity of at least one of the isolated antagonistic antigen binding protein disclosed herein to effectively treat the subject. The dosage can be administered once but may be applied periodically until either a therapeutic result is achieved or until side effects warrant discontinuation of therapy.

The dosing frequency of the administration of the isolated antagonistic antigen binding protein pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the isolated antagonistic antigen binding protein of the present disclosure and one or more other therapeutic agent(s), is intended to mean, and does refer to and include the following: simultaneous administration of such combination of isolated antagonistic antigen binding protein of the disclosure and therapeutic agent(s) to a subject in need of treatment, when such components are formulated together into a single dosage form which releases said components at substantially the same time to said subject; substantially simultaneous administration of such combination of isolated antagonistic antigen binding protein of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of isolated antagonistic antigen binding protein of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of isolated antagonistic antigen binding protein of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

Suitable pharmaceutical agents that may be used in combination with the compounds of the present invention include antihypertensive agents and agents for treating chronic heart failure, atherosclerosis or related diseases. Such agents contemplated for use include, but are not limited to, bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetamide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretamide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), antiplatelets agents (such as aspirin, clopidogrel, ticlopidine, dipyridamole, cilostazol, ethyl icosapentate, sarpogrelate, dilazep, trapidil, beraprost and the like), and neuregulins (NRG-1, NRG-2, NRG-3 and NRG-4) and isoforms thereof.

In various embodiments, the present disclosure comprises a method for treating or preventing heart failure and associated conditions in a subject, comprising administering to a subject diagnosed with heart failure, or a subject at risk of contracting heart failure, a therapeutically effective amount of an isolated antagonistic antigen binding protein that specifically binds to the human glucagon receptor; and (b) a second agent composition. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is selected from a group consisting of: angiotensin-converting enzyme (ACE) inhibitors, β-adrenergic blocking agents, angiotension II receptor blockers (ARBs), diuretics, and digitalis. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is selected from a group consisting of: angiotensin-converting enzyme (ACE) inhibitors, β-adrenergic blocking agents, angiotension II receptor blockers (ARBs), diuretics, and digitalis. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is an angiotensin-converting enzyme (ACE) inhibitor. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is an β-adrenergic blocking agent. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is a diuretic. In various embodiments, an isolated antagonistic antigen binding protein of the present disclosure is a fully human anti-GCGR antibody that comprises a heavy chain sequence as set forth in SEQ ID NO: 51 and a light chain as set forth in SEQ ID NO: 52, and the second agent composition is digitalis.

In various embodiments, the combination therapy comprises administering the isolated antagonistic antigen binding protein composition and the second agent composition simultaneously, either in the same pharmaceutical composition or in separate pharmaceutical compositions. In various embodiments, isolated antagonistic antigen binding protein composition and the second agent composition are administered sequentially, i.e., the isolated antagonistic antigen binding protein composition is administered either prior to or after the administration of the second agent composition.

In various embodiments, the administrations of the isolated antagonistic antigen binding protein composition and the second agent composition are concurrent, i.e., the administration period of the isolated antagonistic antigen binding protein composition and the second agent composition overlap with each other.

In various embodiments, the administrations of the isolated antagonistic antigen binding protein composition and the second agent composition are non-concurrent. For example, in various embodiments, the administration of the isolated antagonistic antigen binding protein composition is terminated before the second agent composition is administered. In various embodiments, the administration second agent composition is terminated before the isolated antagonistic antigen binding protein composition is administered.

The invention having been described, the following examples are offered by way of illustration, and not limitation.

Example 1

In this example, the present inventors evaluated the therapeutic potential of a monoclonal antibody against the glucagon receptor on LV remodeling in post-myocardial infarction heart failure. In this example, the in vivo activity of an anti-GCGR antibody which comprises the heavy chain sequence set forth in SEQ ID NO: 8 and the light chain sequence set forth in SEQ ID NO: 9 ("REMD2.59C") is evaluated using myocardial infarction induced C57BL/6 mice.

Myocardial infarction (MI) was induced in 54 C57BL6 male mice at the age of 8-10 weeks old by occluding the left coronary artery. After MI, mice were randomly divided into three groups. Group 1 was treated with the vehicle PBS as a control (CON, n=18); Group 2 was treated with 7.5 mg/kg REMD2.59C mAb, s.c. at 2 hours and at 14 days post-MI (mAb, n=18); and Group 3 was treated with glucagon (30 ng/kg body weight in 10% gelatin) three times per day for the first six days post MI (GLC, n=18). Sham animals were used as a negative control.

Infarcted mice were checked for survival every day for 28 days. Survival curves were delineated over time. Fasting blood glucose measurements are taken at 2 weeks post-MI. Cardiac function was monitored during the post-MI recovery. At the end of the 28 day study, the mice were euthanized and the hearts were harvested for histological studies and ventricular contraction (echo FS/EF), ventricular pressure and contractility (catheter); ventricular remodeling, septum and LV wall thickness (echo), cardiac index (HW/BW), myocyte hypertrophy, fibrosis; infarct size, and apoptosis were determined.

Cardiac function was measured by echocardiography three times, the first day after MI, then at 14 and 28 days post-MI. The first echo was used to screen infarcted mice for no infarction. The mice with left ventricular fractional shortening greater than 40% were eliminated from the study. At the end of the experiment, ventricular function was measured by Micro-tip pressure transducer (catheter). For the histological studies, the heart was perfused with 10% formalin for fixation. Cardiac sections from the apex, middle, and base of the heart were used for Masson's trichrome staining (MTS) and TUNEL staining. Infarct size was measured in MTS sections, and apoptosis was assessed in the sections after TUNEL staining. The protective effect of REMD2.59C mAb was assessed based on infarct size and apoptosis. Fibrosis and myocyte size were measured in MTS sections for assessment of cardiac remodeling.

Figure 2:
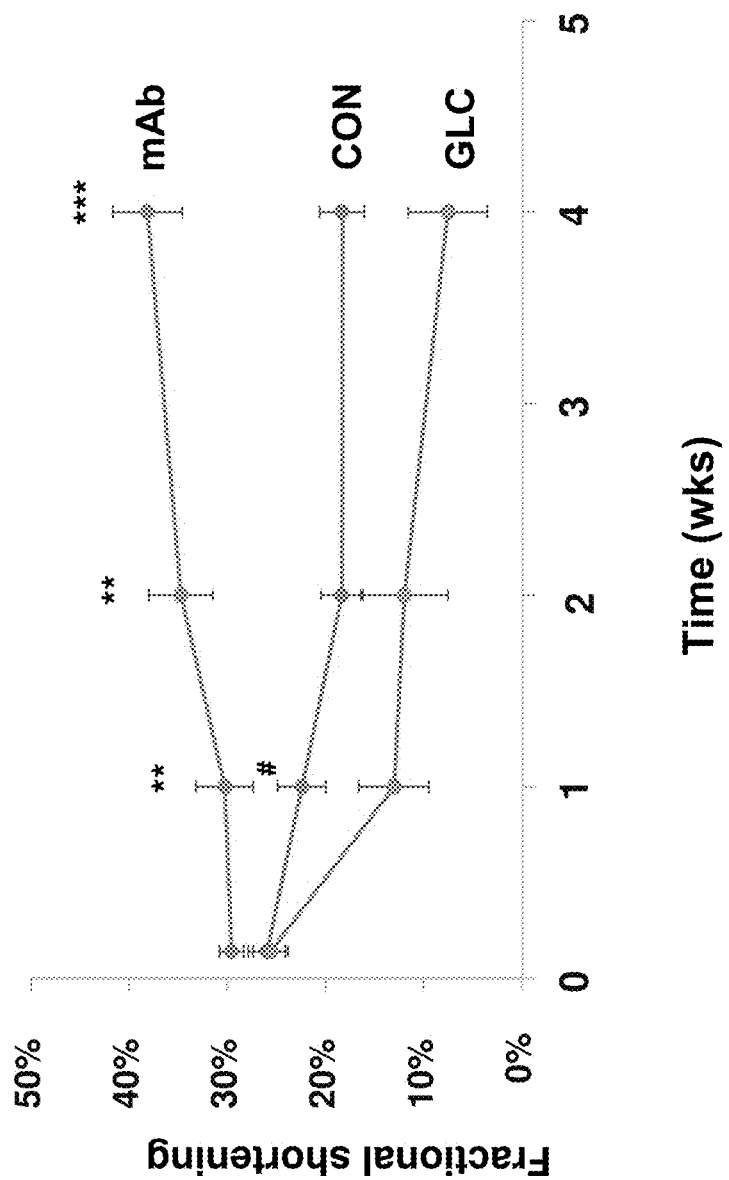
FIG. 2 is a line plot depicting the in vivo effects on left ventricular fractional shortening (FS) for the control (CON) group (n=10), REMD2.59 (mAb) treated group (n=11), and glucagon (GLC) treated group (n=6) throughout a 28 day study wherein myocardial infarction (MI) was induced in 54 C57BL6 male mice. % FS is plotted vs. time (weeks). #: P<0.05 Con vs GLC, : P<0.01 mAb vs GLC, *: P<0.001 mAb vs CON or GLC.
Figure 3:
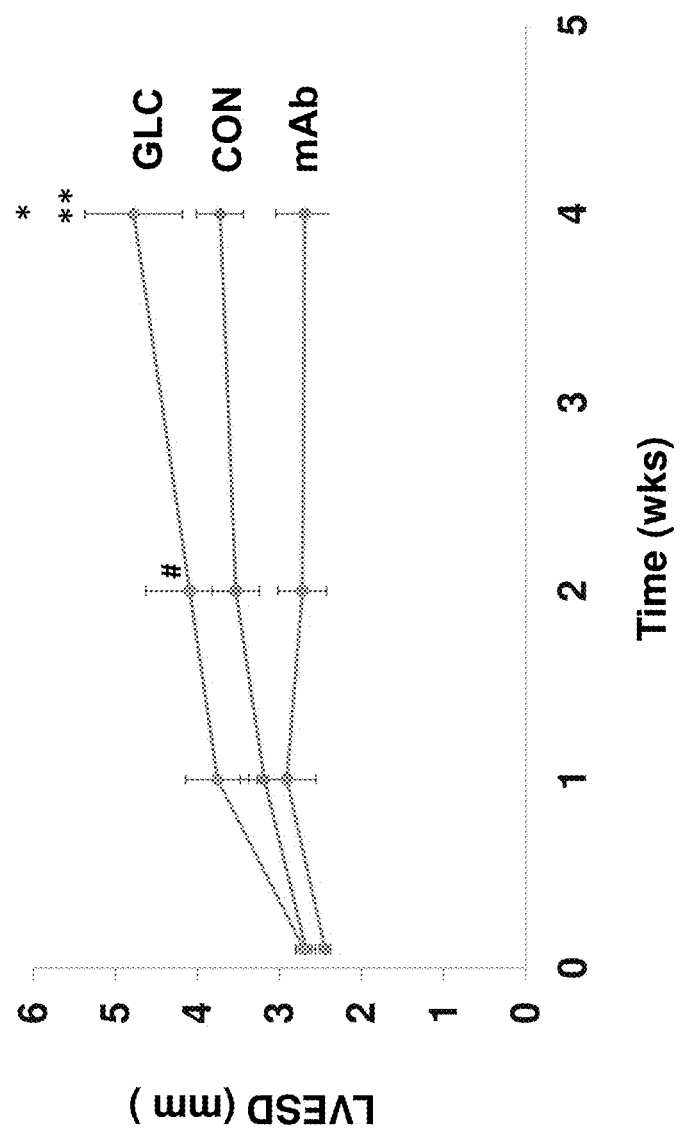
FIG. 3 is a line plot depicting the in vivo effects on left ventricular end systolic diameter (LVESD) for the control (CON) group (n=10), REMD2.59 (mAb) treated group (n=11), and glucagon (GLC) treated group (n=6) throughout a 28 day study wherein myocardial infarction (MI) was induced in 54 C57BL6 male mice. LVESD (mm) is plotted vs. time (weeks). #: p<0.05 vs GLC, *: p<0.05 vs CON, **: p<0.01 vs GLC.
Figure 4:
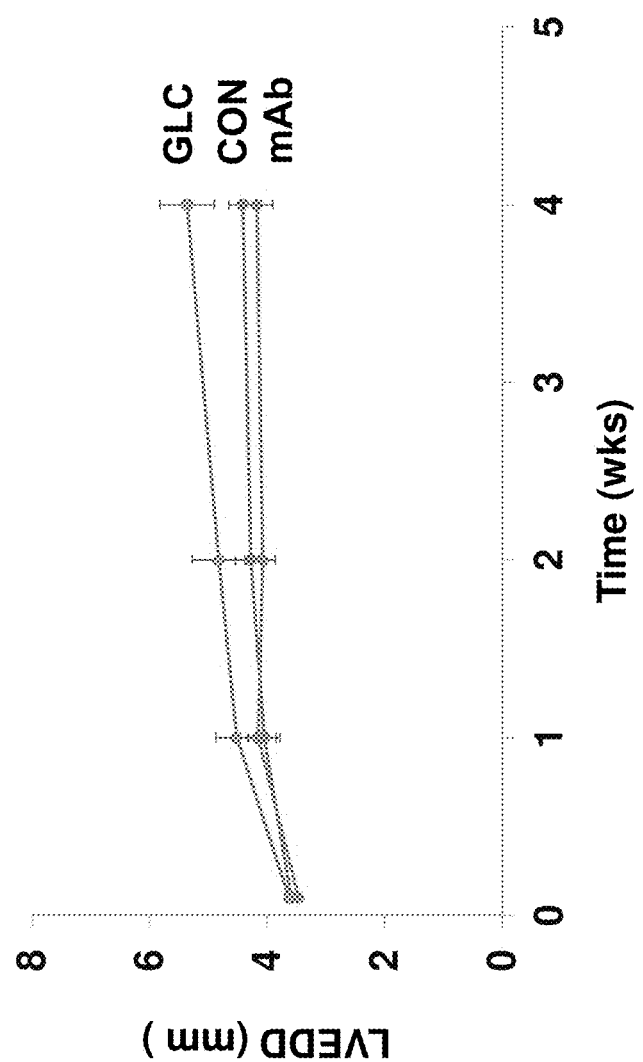
FIG. 4 is a line plot depicting the in vivo effects on left ventricular end diastolic dimension (LVEDD) for the control (CON) group (n=10), REMD2.59 (mAb) treated group (n=11), and glucagon (GLC) treated group (n=6) throughout a 28 day study wherein myocardial infarction (MI) was induced in 54 C57BL6 male mice. LVEDD (mm) is plotted vs. time (weeks).
Figure 5:
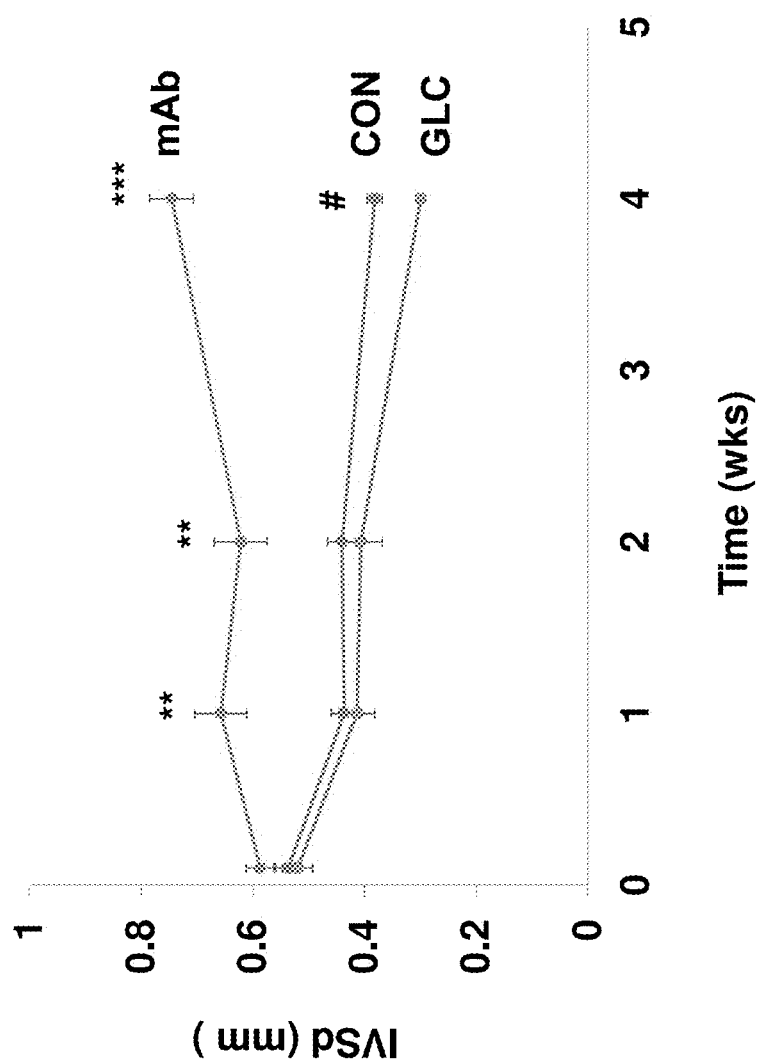
FIG. 5 is a line plot depicting the in vivo effects on ischemic left ventricular wall thickness (IVSd) for the control (CON) group (n=10), REMD2.59 (mAb) treated group (n=11), and glucagon (GLC) treated group (n=6) throughout a 28 day study wherein myocardial infarction (MI) was induced in 54 C57BL6 male mice. IVEDD (mm) is plotted vs. time (weeks). : P<0.01 vs CON or GLC, *: P<0.001 vs CON or GLC, #: P<0.05 Con vs GLC.
Figure 6:
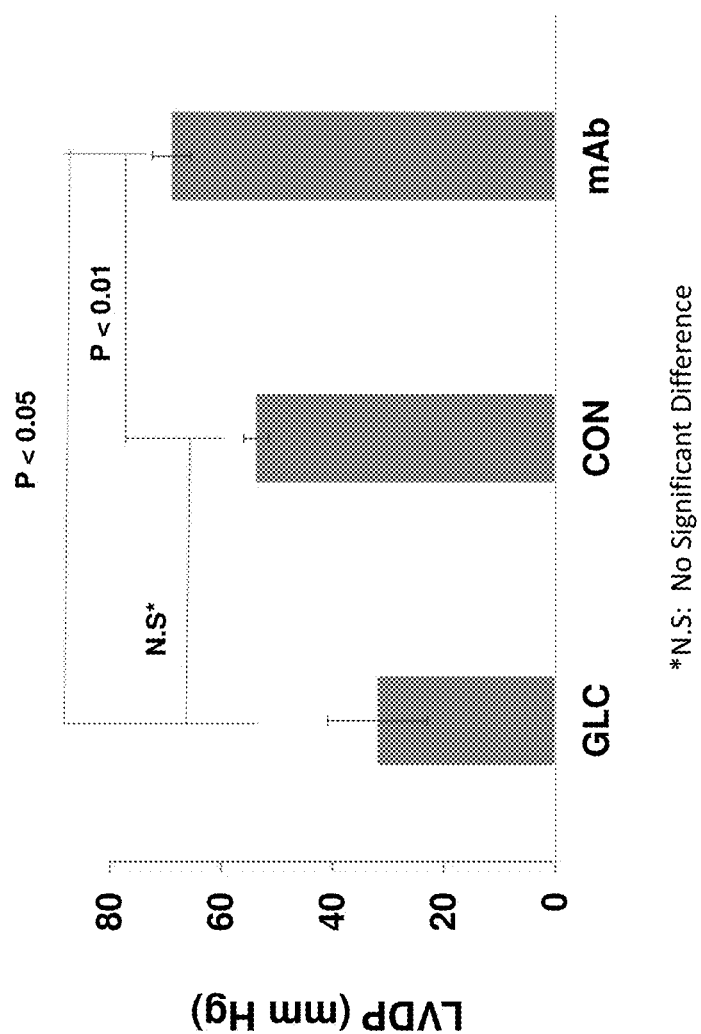
FIG. 6 is a bar graph depicting the in vivo effects on left ventricular diastole pressure (LVDP) for the control (CON) group, REMD2.59 (mAb) treated group, and glucagon (GLC) treated group in a study wherein myocardial infarction (MI) was induced in 54 C57BL6 male mice. LVDP (mm Hg) at 28 days is depicted.
Figure 7:
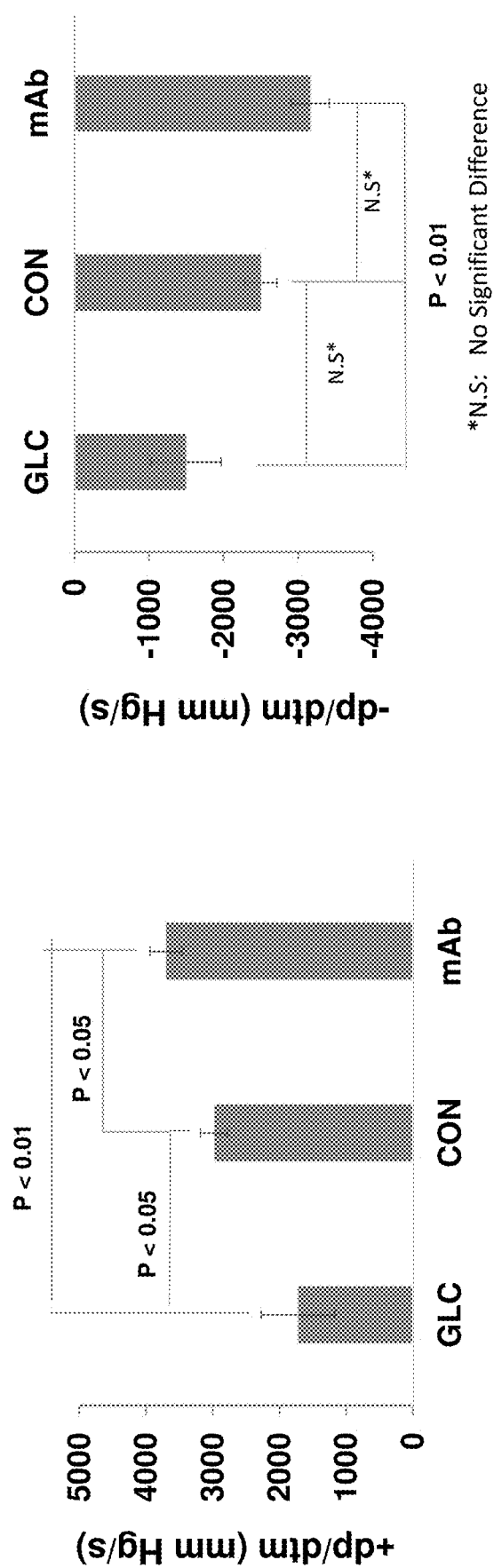
FIG. 7 contains bar graphs depicting the in vivo effects on cardiac contractility (+dp/dtm-mm Hg/s)(left panel) and relaxation (−dp/dtm-mm Hg/s)(right panel) for the control (CON) group, REMD2.59 (mAb) treated group, and glucagon (GLC) treated group in a study wherein myocardial infarction (MI) was induced in 54 C57BL6 male mice. Cardiac contractility (+dp/dtm-mm Hg/s)(left panel) and relaxation (−dp/dtm-mm Hg/s)(right panel) at 28 days is depicted.
Figure 8:
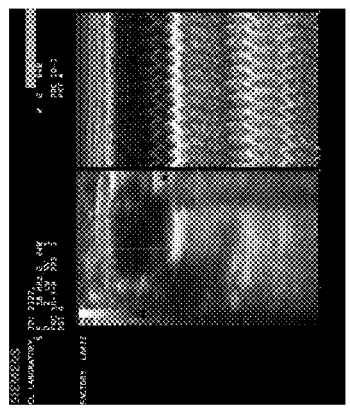
FIG. 8 are echo readouts and corresponding pictures depicting the in vivo effects on cardiac remodeling for the control (CON) group, REMD2.59 (mAb) treated group, and glucagon (GLC) treated group at day 28 of a study wherein myocardial infarction (MI) was induced in 54 C57BL6 male mice.
Figure 8:
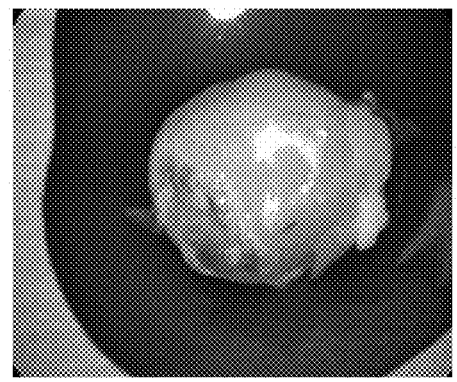
Figure 8:
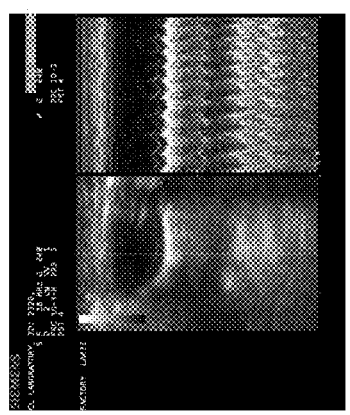
Figure 8:
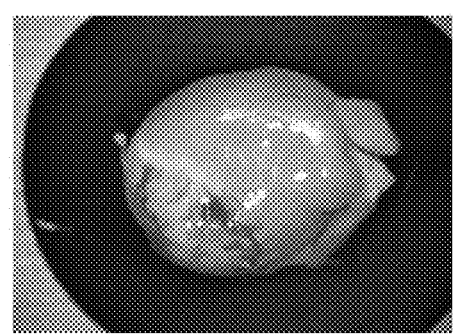
Figure 8:
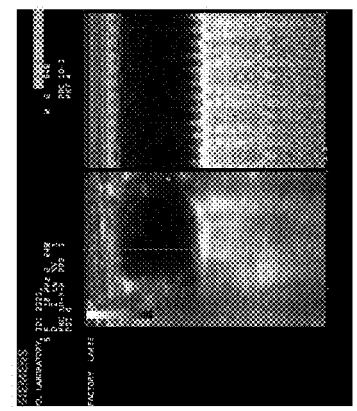
Figure 8:
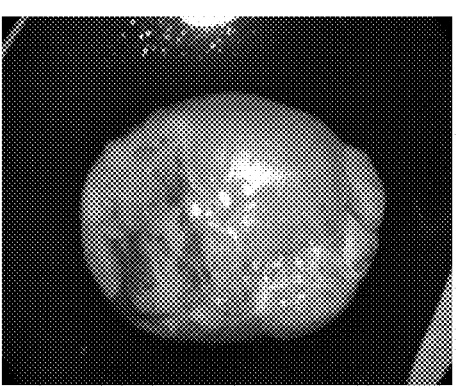
Figure 9:
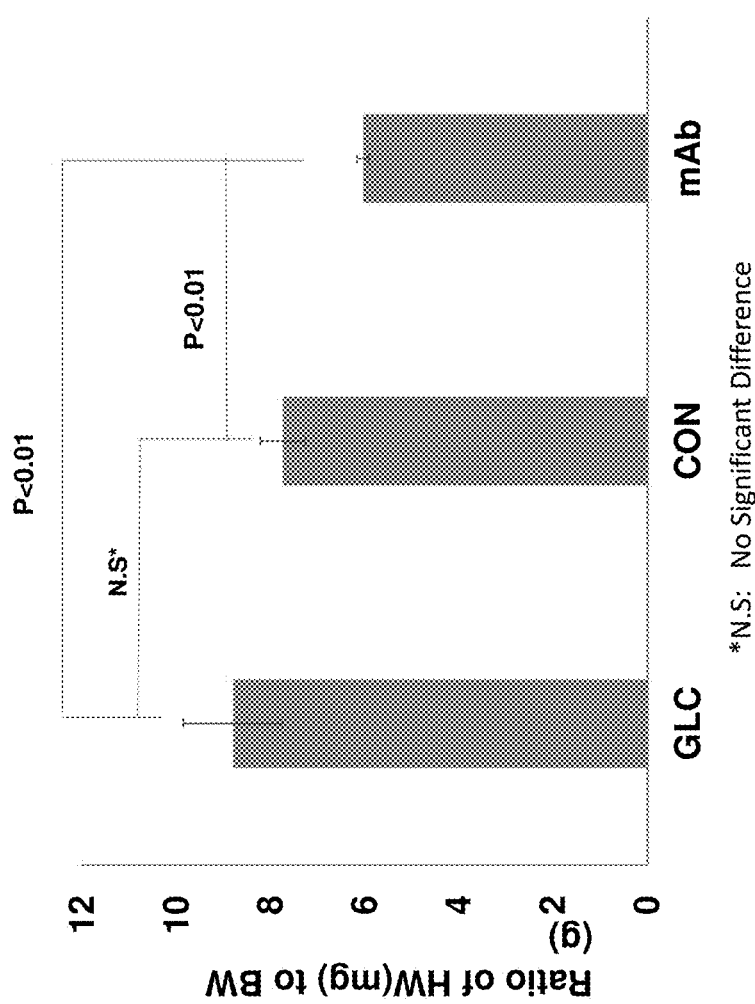
FIG. 9 is a bar graph depicting the in vivo effects on cardiac remodeling for the control (CON) group, REMD2.59 (mAb) treated group, and glucagon (GLC) treated group at day 28 of a study wherein myocardial infarction (MI) was induced in 54 C57BL6 male mice. The ratio of Heart weight (HW)(mg) vs. Body weight (BW)(g) at 28 days is depicted.
Figure 10:
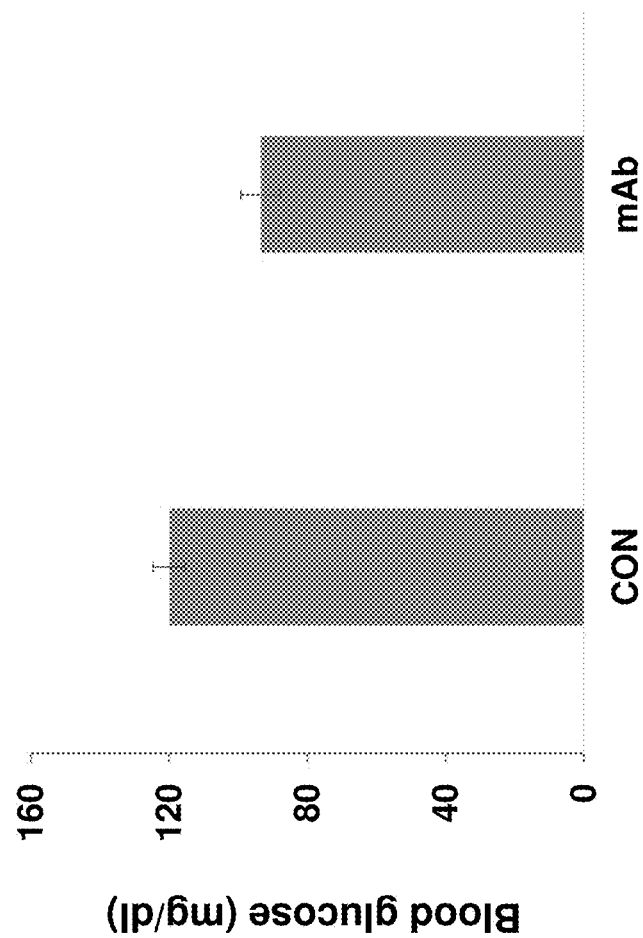
FIG. 10 is a bar graph depicting the in vivo effects on blood glucose levels for the control (CON) group and REMD2.59 (mAb) treated group at day 14 of a study wherein myocardial infarction (MI) was induced in 54 C57BL6 male mice. Blood glucose levels (mg/dl) (fasted for 4 hours) at 14 days is depicted. *: P<0.01.
Figure 11:
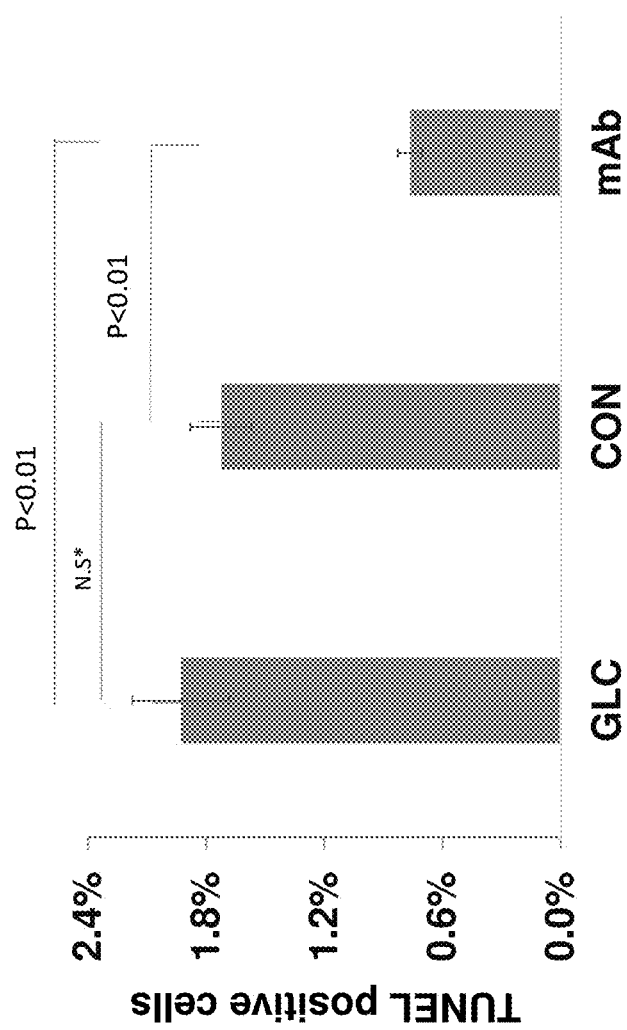
FIG. 11 is a bar graph depicting in vivo effects on apoptosis in the infarct area for the control (CON) group, REMD2.59 (mAb) treated group, and glucagon (GLC) treated group at day 28 of a study wherein myocardial infarction (MI) was induced in 54 C57BL6 male mice. 8 fields in each mouse were counted. % TUNEL positive cells at 28 days is depicted.
Figure 12:
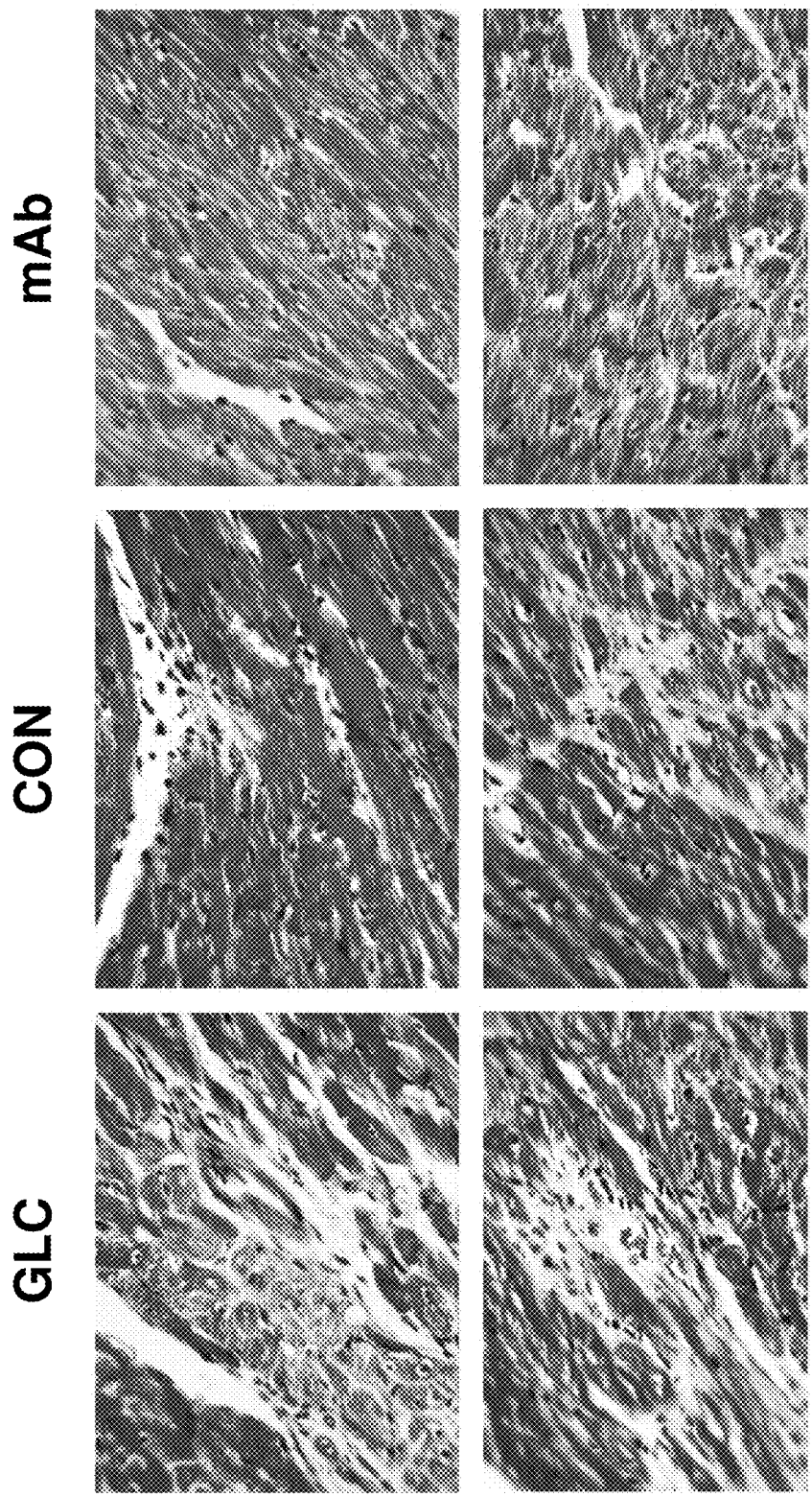
FIG. 12 depicts histological H&E staining of various sections depicting in vivo effects on fibrosis in the non-infarct area for the control (CON) group, REMD2.59 (mAb) treated group, and glucagon (GLC) treated group at day 28 of a study wherein myocardial infarction (MI) was induced in 54 C57BL6 male mice.
Figure 13:
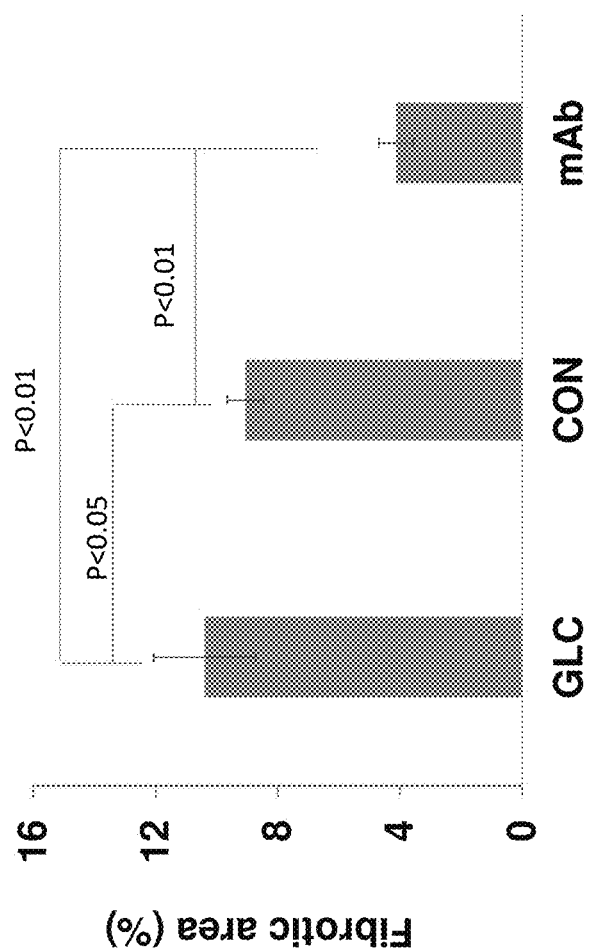
FIG. 13 is a bar graph depicting in vivo effects on fibrosis in the non-infarct area for the control (CON) group, REMD2.59 (mAb) treated group, and glucagon (GLC) treated group at day 28 of a study wherein myocardial infarction (MI) was induced in 54 C57BL6 male mice. 8 fields in each mouse were counted. % fibrotic area at 28 days is depicted.
Figure 14:
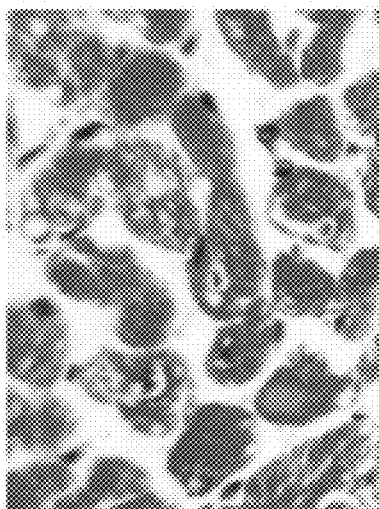
FIG. 14 depicts histological H&E staining of various sections depicting in vivo effects on myocyte hypertrophy in the non-infarct area for the control (CON) group, REMD2.59 (mAb) treated group, and glucagon (GLC) treated group at day 28 of a study wherein myocardial infarction (MI) was induced in 54 C57BL6 male mice. Magnification 40×10.
Figure 14:
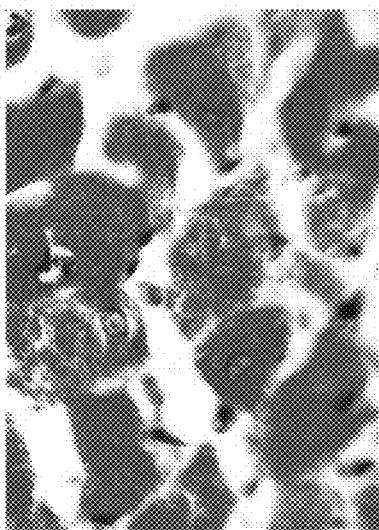
Figure 14:
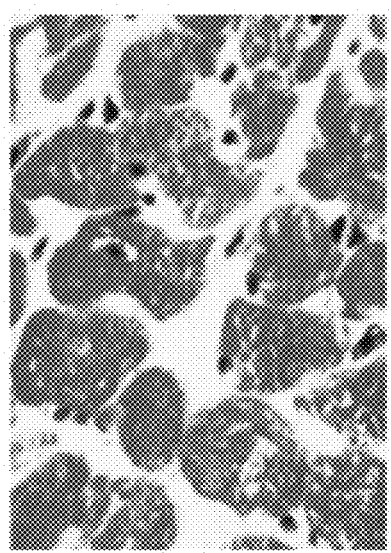
Figure 15:
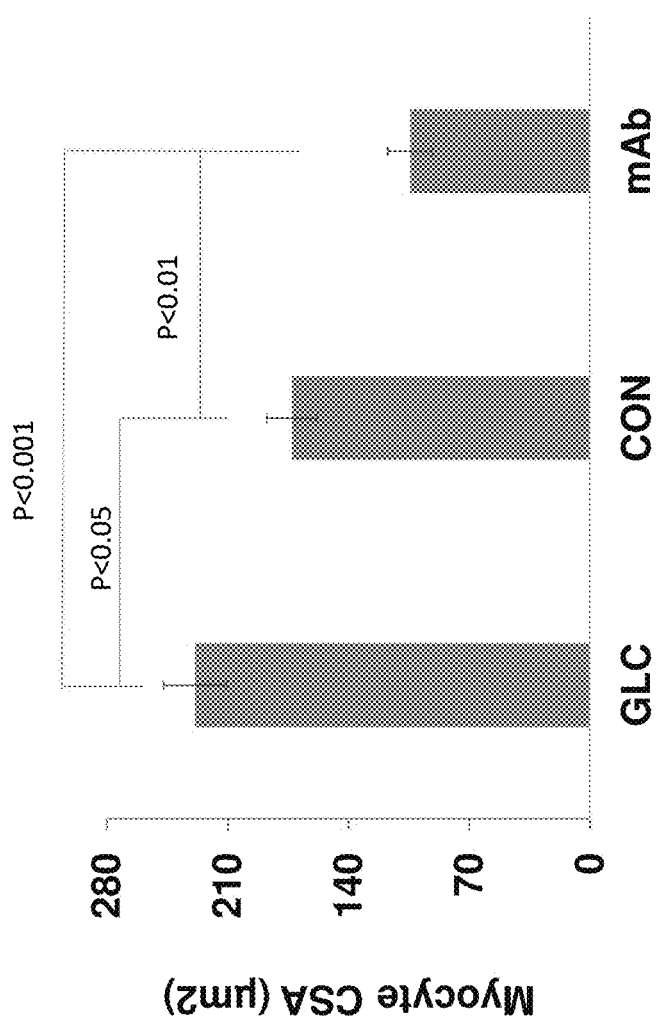
FIG. 15 is a bar graph depicting in vivo effects on myocyte hypertrophy in the non-infarct area for the control (CON) group, REMD2.59 (mAb) treated group, and glucagon (GLC) treated group at day 28 of a study wherein myocardial infarction (MI) was induced in 54 C57BL6 male mice. 8 fields in each mouse were counted. Myocyte CSA ($\mu m^2$) at 28 days is depicted.
Figure 16:
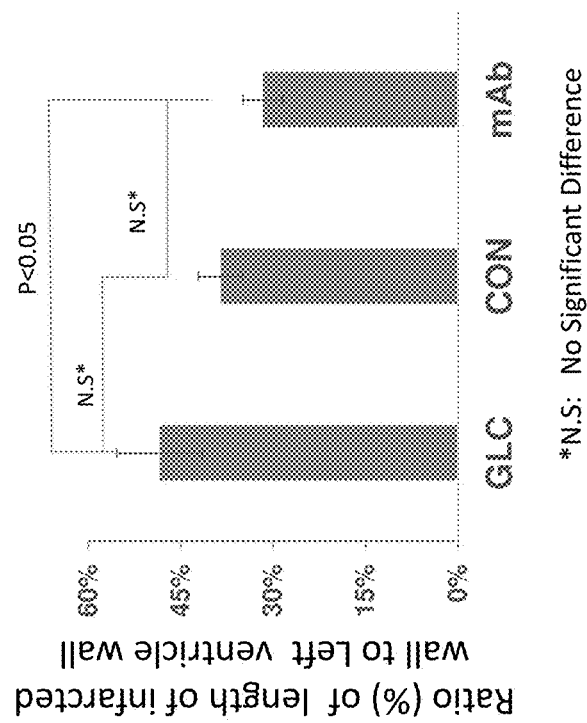
FIG. 16 is a bar graph and corresponding pictures depicting the in vivo effects on infarct size for the control (CON) group, REMD2.59 (mAb) treated group, and glucagon (GLC) at day 28 of a study wherein myocardial infarction (MI) was induced in 54 C57BL6 male mice. Ratio (%) of length of infarcted wall to LV wall at 28 days is depicted.
Figure 16:
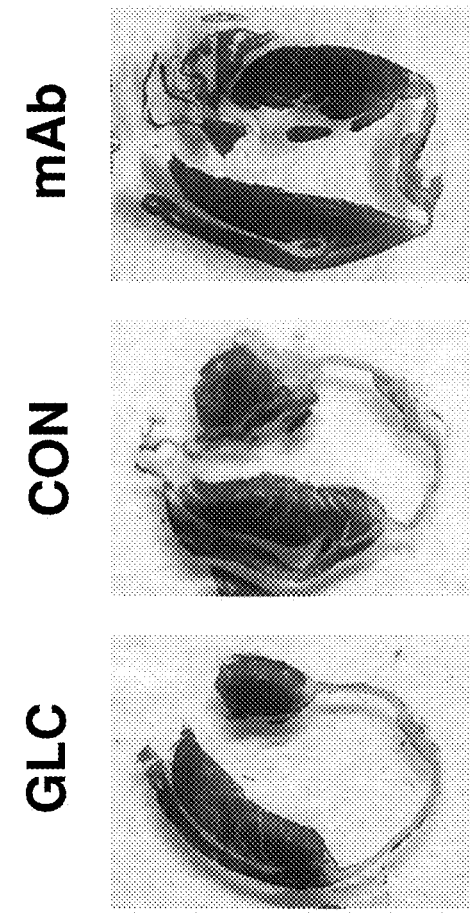
Figure 17:
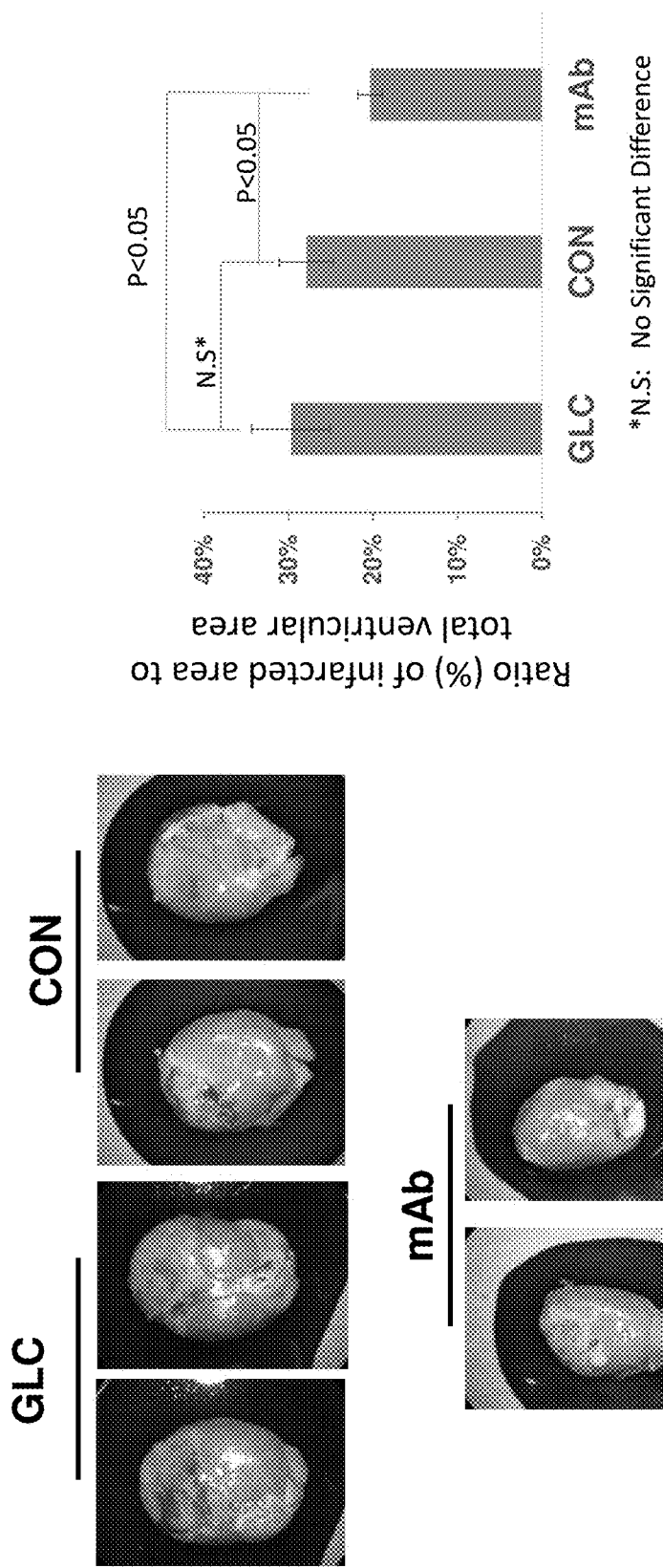
FIG. 17 is a bar graph and corresponding pictures depicting the in vivo effects on infarct area for the control (CON) group, REMD2.59 (mAb) treated group, and glucagon (GLC) at day 28 of a study wherein myocardial infarction (MI) was induced in 54 C57BL6 male mice. Ratio (%) of length of infarcted area to total ventricular area at 28 days is depicted.

As depicted in FIG. 1, at the end of the study, MI caused 55% (10/18) mortality in CON mice, while REMD2.59C mAb treatment reduced the mortality (11/18 or 61% of the mice survived), and glucagon treatment increased the mortality (6/18 or 33% of the mice survived). As depicted in FIG. 2, mAb significantly increased left ventricular fractional shortening (FS) as compared to CON, while GLC reduced it as compared to CON. As depicted in FIG. 3, mAb attenuated left ventricular end systolic diameter (LVESD) as compared to CON, while GLC increased it as compared to CON. As depicted in FIG. 4, mAb attenuated left ventricular end diastolic dimension (LVEDD) as compared to CON, while GLC increased it as compared to CON. As depicted in FIG. 5, mAb preserved left ventricular ischemic muscle as compared to CON, while GLC slightly reduced it as compared to CON. As depicted in FIG. 6, mAb increased left ventricular contraction as compared to CON, while GLC decreased it as compared to CON. As depicted in FIG. 7, mAb increased cardiac contractility (left panel) and relaxation (right panel) as compared to CON, while GLC decreased both as compared to CON. As depicted in FIG. 8 mAb attenuated cardiac remodeling as compared to CON while GLC slightly increased heart weight as compared to CON. As depicted in FIG. 9, mAb attenuated cardiac remodeling (decreased HW/BW) as compared to CON, while GLC slightly increased HW/BW as compared to CON. As depicted in FIG. 10, mAb decreased blood glucose levels in mice (fasted for 4 hours) as compared to CON at 2 weeks post-MI. As depicted in FIG. 11, apoptosis was attenuated by mAb in the infarct area. As depicted in FIG. 12 and FIG. 13, fibrosis was attenuated by mAb in non-infarct area. As depicted in FIG. 14 and FIG. 15, monocyte hypertrophy was attenuated by mAb in non-infarct area. As depicted in FIG. 16, infarct size was decreased by mAb at weeks after MI. As depicted in FIG. 17, infarct area was decreased by mAb at weeks after MI.

Histology findings strongly support the protective effects of glucagon receptor mAb against post-MI ventricular remodeling. Treatment with glucagon receptor mAb attenuated apoptosis in infarcted area and decreased myocyte hypertrophy and fibrosis in non-infarct area. Infarct area was decreased by glucagon receptor mAb at 4 weeks after MI, compared with PBS control. Cardiac remodeling was attenuated by the monoclonal antibody against glucagon receptor, which decreased HW/BW, increased LV contractility (+dp/dtm) and FS, and preserved LV wall thickness. Administering glucagon (the ligand) promoted cardiac remodeling and worsened heart function, suggesting that glucagon signaling plays a role in post-MI remodeling.

The surprising results of these studies suggest that glucagon signaling is involved in post-MI ventricular remodeling, and that targeting glucagon receptor with an antagonistic mAb may be an effective therapeutic approach to prevention of heart failure after myocardial infarction. The glucagon receptor antibody may be a powerful weapon in fighting against adverse cardiac remodeling and heart failure after MI.

Example 2

In this example, the present inventors evaluated the potential preventive efficacy of a human anti-GCGR antibody on cardiomyopathy induced by diabetes in db/db mice. In this example, the in vivo activity of a human anti-GCGR antibody which comprises the heavy chain sequence set forth in SEQ ID NO: 51 and the light chain sequence set forth in SEQ ID NO: 52 ("REMD477") was evaluated using C57BL/6/db/db male diabetes mice and db/+ male control mice.

In this 18 week study, 30 C57BL6/db/db diabetes male mice at the age of 8-10 weeks and 18 db/+ male mice were randomly divided into four groups. In Group 1, db/+ mice (n=9) where treated with the vehicle PBS as a control (hereinafter "db/+ (PBS)"); in Group 2, db/+ mice (n=9) were treated with REMD477 (hereinafter "db/+ (mAb)"); in Group 3, db/db diabetes mice (n=15) where treated with the vehicle PBS as a control (hereinafter "db/db (PBS)"); and in Group 4, db/db mice (n=15) were treated with REMD477 (hereinafter "db/db (mAb)"). For Groups 2 and 4, REMD477 was dosed at 7 mg/kg weekly SC, and then 3 mg/kg weekly SC up to 18 week, for a total of 13 injections. For Groups 1 and 3, 01. ml/mouse PBS was dosed at the same frequency as treatment Groups 2 and 4. At the end of the 18 week study, the mice are euthanized and the hearts are harvested for histological studies.

Body weight, fasting blood glucose, and OGTT measurements are taken at 0, 4, 8, 12 and 18 weeks after treatment. Blood insulin levels and blood glucagon levels were measured at 0, 6, 12 and 18 weeks after treatment. Cardiac function was measured by echocardiography at day 1 after treatment, then at 6, 12 and 18 weeks post treatment. The first echo was used to screen infarcted mice for no infarction. The mice with left ventricular fractional shortening greater than 40% were eliminated from the study. Cardiac function changes (e.g., ventricular systolic (echo/FS/EF) and diastolic (echo E/A and IRT) function, ventricular pressure and contractility (catheter), and cardiac output (echo)) are monitored at 0, 6, 12 and 18 weeks after treatment. LV remodeling is measured by Micro-tip pressure transducer (catheter) at 18 weeks after treatment, e.g., left ventricular diastole pressure (mmHg) and cardiac index (HW/BW) is measured at 18 weeks after treatment by Micro-tip catheter. Serum level GLP-1 and GHbAc1 measurements are taken at day 0 and at 18 weeks after treatment.

For the histological studies, the heart is perfused with 10% formalin for fixation. Cardiac sections from the apex, middle, and base of the heart are used for Masson's trichrome staining (MTS) and TUNEL staining. Infarct size is measured in MTS sections, and apoptosis is assessed in the sections after TUNEL staining. Fibrosis and myocyte size were measured in MTS sections for assessment of cardiac remodeling.

Figure 18:
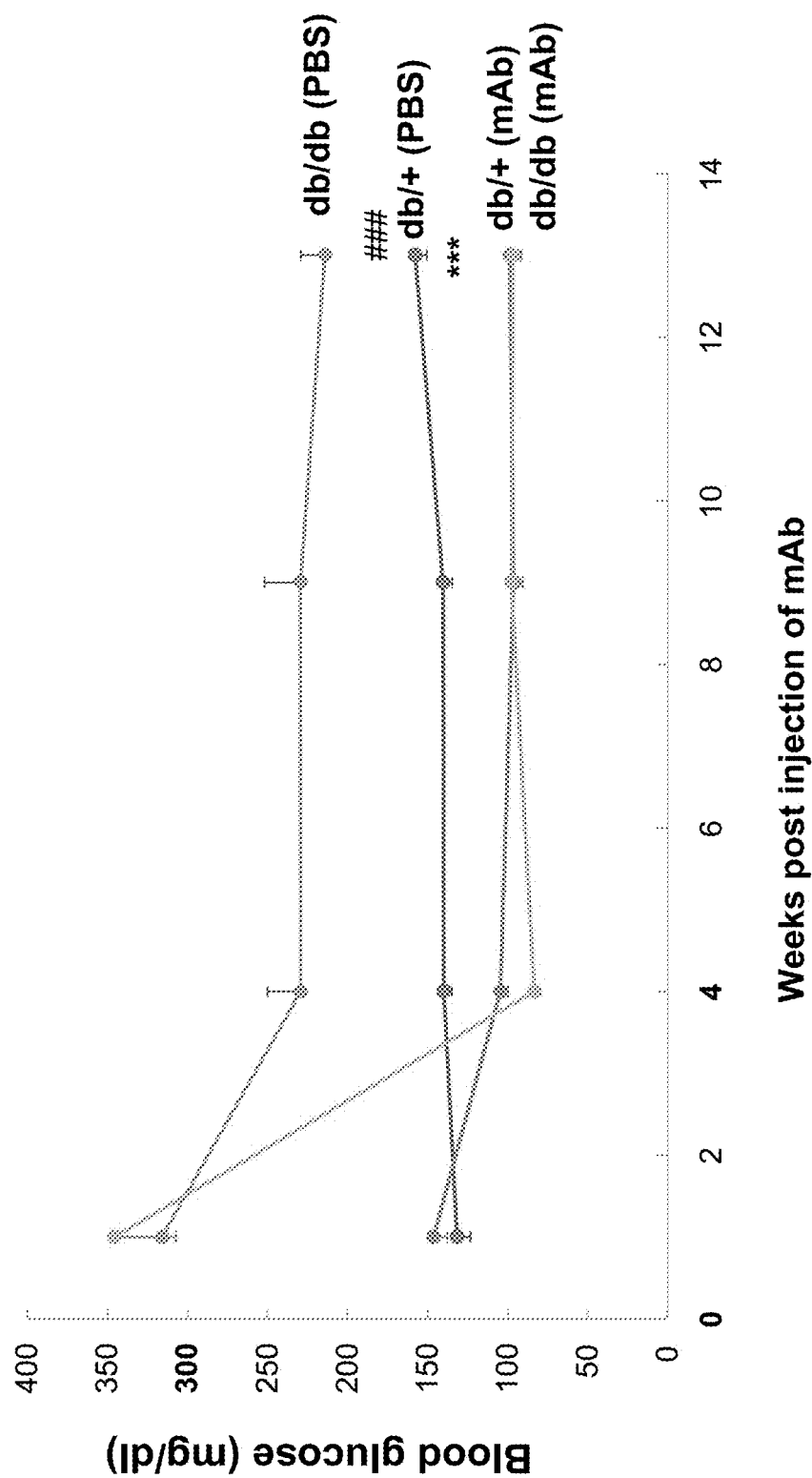
FIG. 18 is a line plot depicting the blood glucose levels (mg/dl) for the db/db (PBS), db/db (mAb), db/+ (PBS), and db/+ (mAb) groups throughout the 18 week study. Each mouse was fasting 6 hours, and repeated measurement ANOVA was used for statistical analysis. ***: p<0.0001 compared db/db (mAb) vs db/db (PBS); ###: p<0.0001 compare db/+ (PBS) or db/+ (mAb) vs db/db (PBS).
Figure 19:
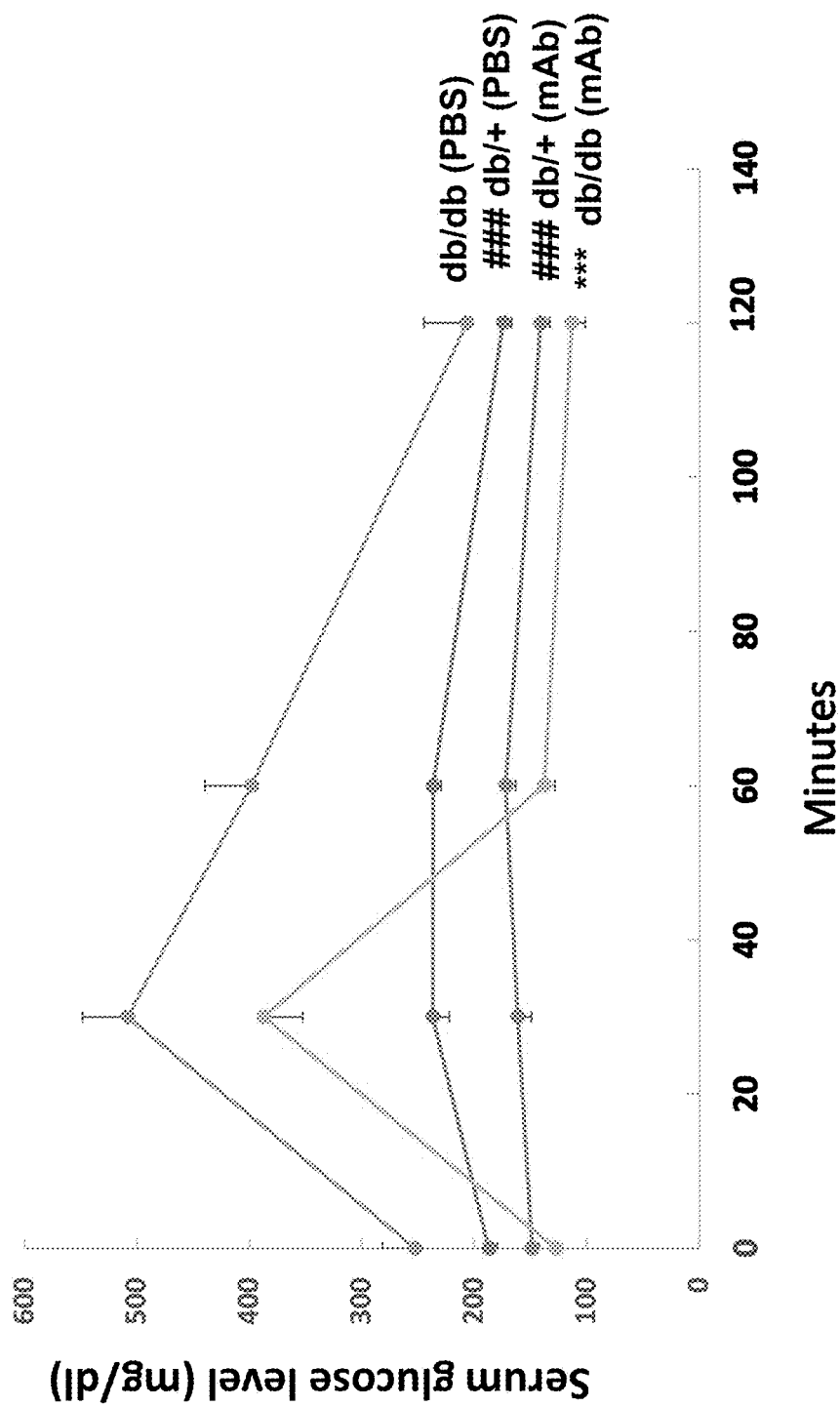
FIG. 19 is a line plot depicting the results of an oral glucose tolerance test (OGTT) for the db/db (PBS), db/db (mAb), db/+ (PBS), and db/+ (mAb) groups at week 18 week after treatment with mAb or PBS. Each mouse received 2.0 g/kg of glucose with gavage. Following oral administration of 2 g/kg glucose, the blood glucose levels were measured at different time points (30, 60, 120 min) by using Accu-Chek Performa System. Serum glucose levels (mg/dl) is plotted vs. time (minutes) using repeated measurement ANOVA for statistical analysis. ***: p<0.0001 compared db/db (mAb) vs db/db (PBS); ###: p<0.0001 compare db/+ (PBS) or db/+ (mAb) vs db/db (PBS).
Figure 20:
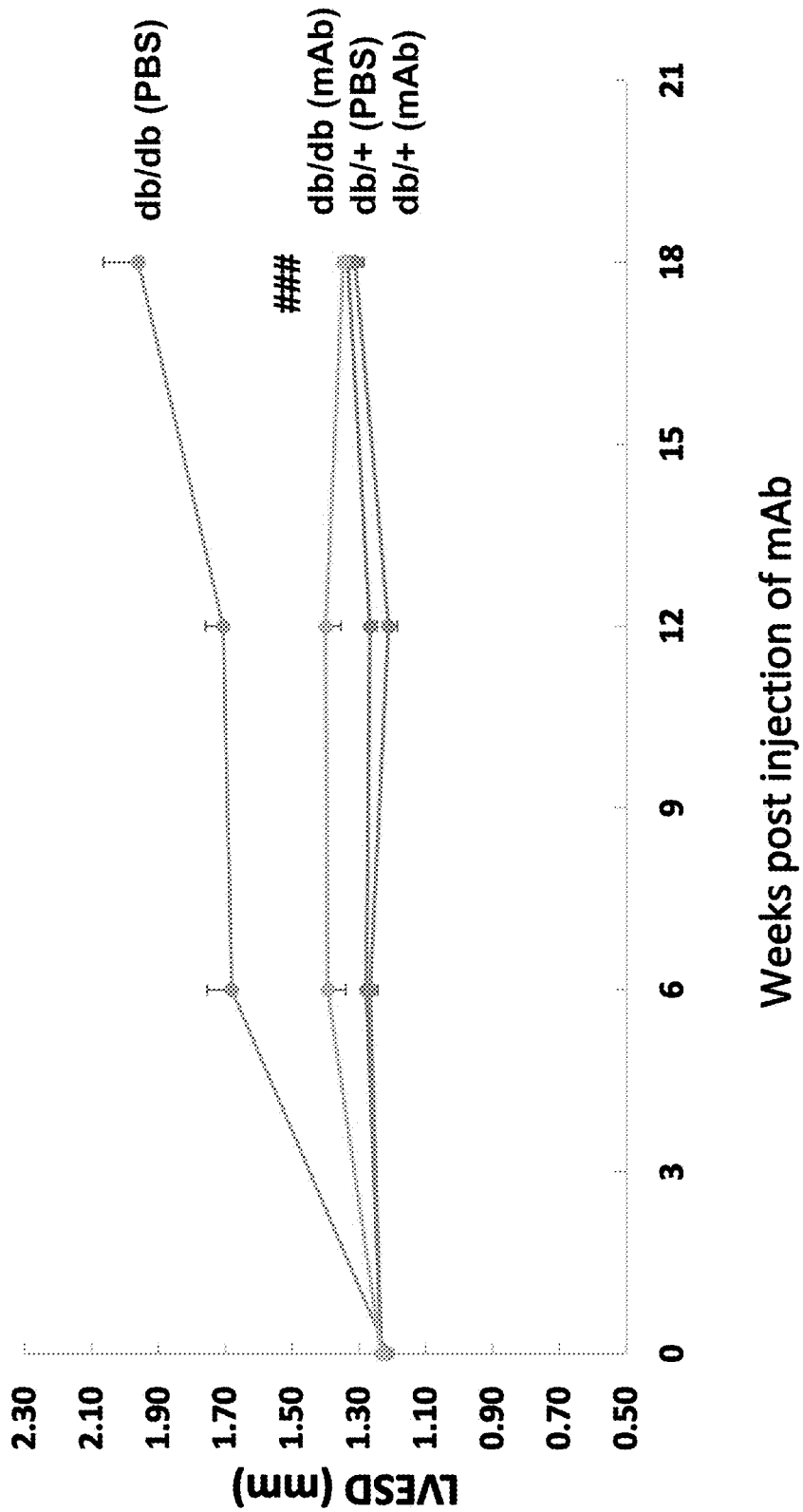
FIG. 20 is a line plot depicting the in vivo effects on left ventricular end systolic diameter (LVESD) for the db/db (PBS), db/db (mAb), db/+ (PBS), and db/+ (mAb) groups throughout the 18 week study. LVESD (mm) is plotted vs. time (weeks) using repeated measurement ANOVA for statistical analysis. ***: p<0.0001 compared db/db (mAb) vs db/db (PBS); ###: p<0.0001 compare db/+ (PBS) or db/+ (mAb) vs db/db (PBS).
Figure 21:
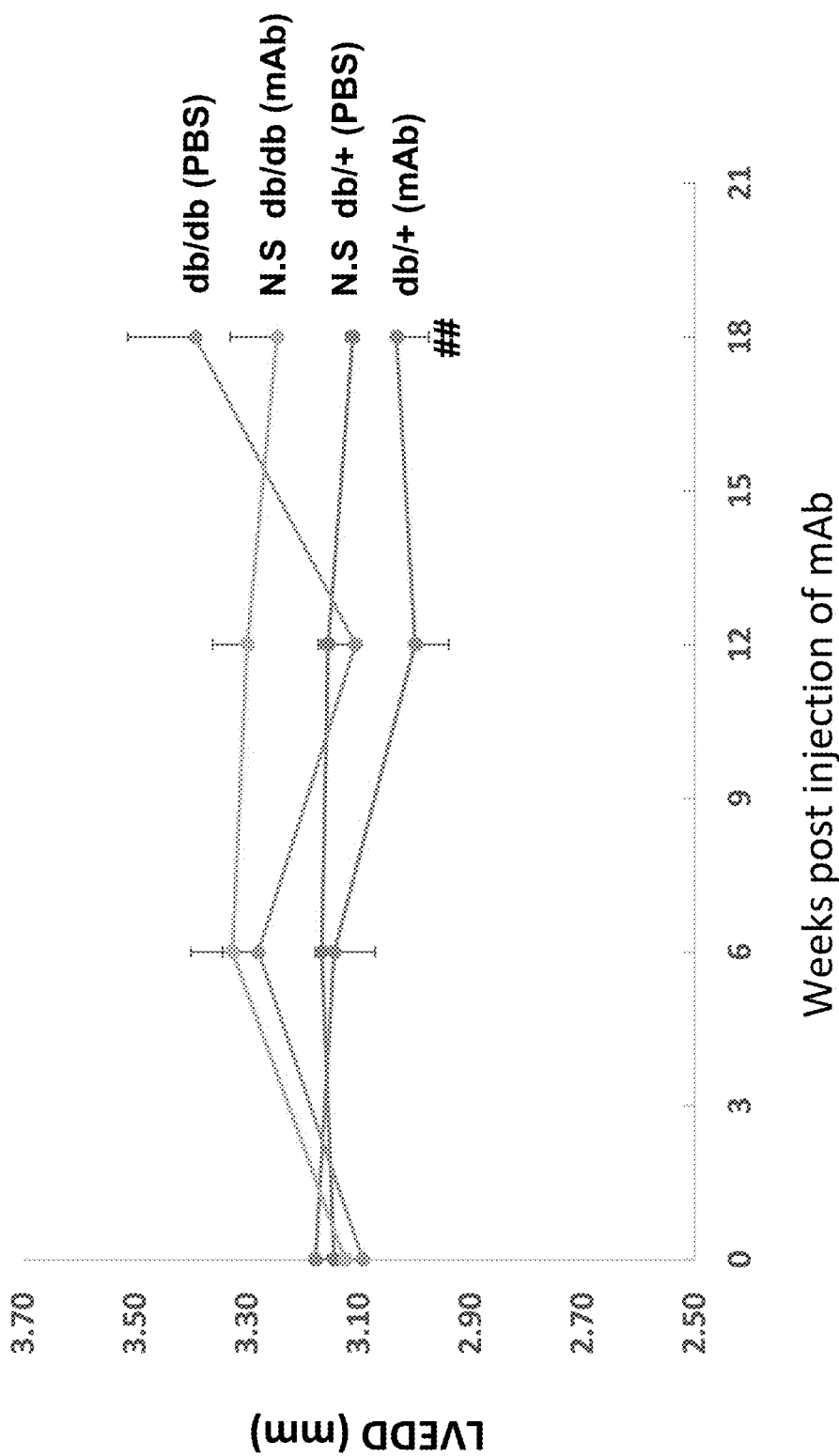
FIG. 21 is a line plot depicting the in vivo effects on left ventricular end diastolic dimension (LVEDD) for the db/db (PBS), db/db (mAb), db/+ (PBS), and db/+ (mAb) groups throughout the 18 week study. LVEDD (mm) is plotted vs. time (weeks). P values, ##: p<0.01, compared db/+ (mAb) vs. db/db (PBS); N.S: there is no significant differences compared to db/db (PBS) group based on repeated measurement ANOVA, Bonferroni/Dunn method.
Figure 22:
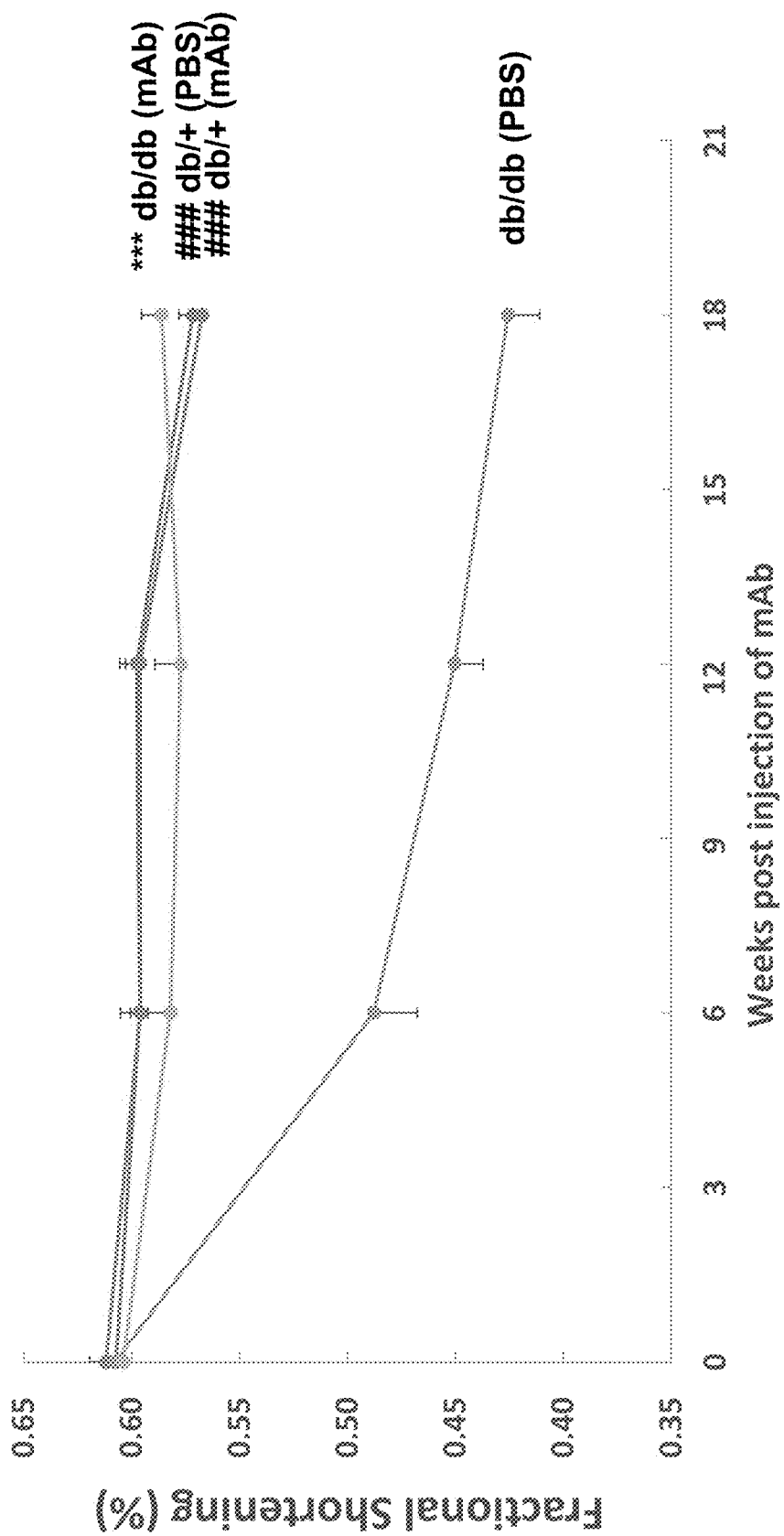
FIG. 22 is a line plot depicting the in vivo effects on left ventricular fractional shortening (FS) for the db/db (PBS), db/db (mAb), db/+ (PBS), and db/+ (mAb) groups throughout the 18 week study using repeated measurement ANOVA to compare whole time points between groups. ***: p<0.0001, compared db/db (mAb) vs. db/db (PBS), ###: p<0.0001, compared db/+ (PBS) or db/+ (mAB) vs. db/db (PBS).
Figure 23:
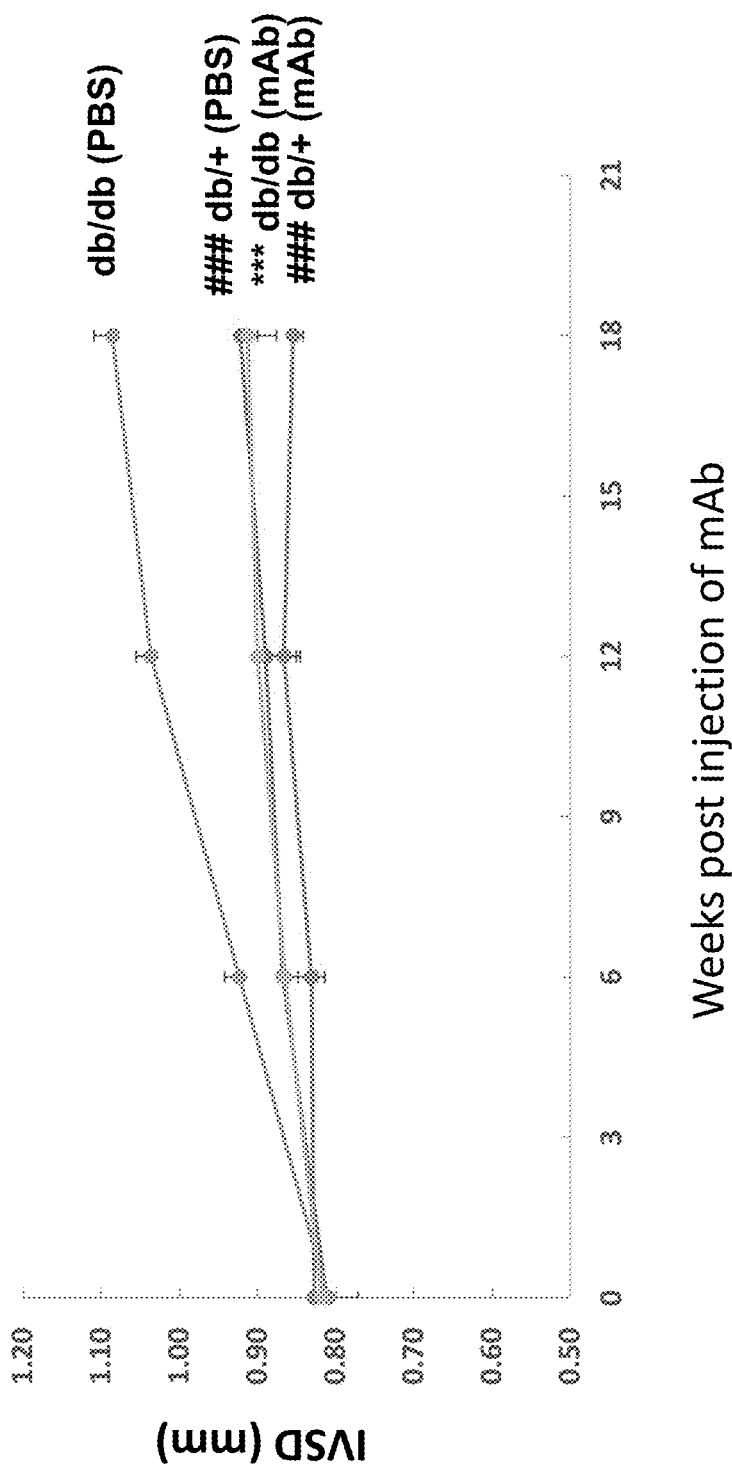
FIG. 23 is a line plot depicting the in vivo effects on interventricular septal end diastole (IVSD) for the db/db (PBS), db/db (mAb), db/+ (PBS), and db/+ (mAb) groups throughout the 18 week study using repeated measurement ANOVA for statistical analysis. P values, ***: p<0.0001 compared db/db (mAb) vs db/db (PBS); ###: p<0.0001 compare db/+ (PBS) or db/+ (mAb) vs db/db (PBS).
Figure 24:
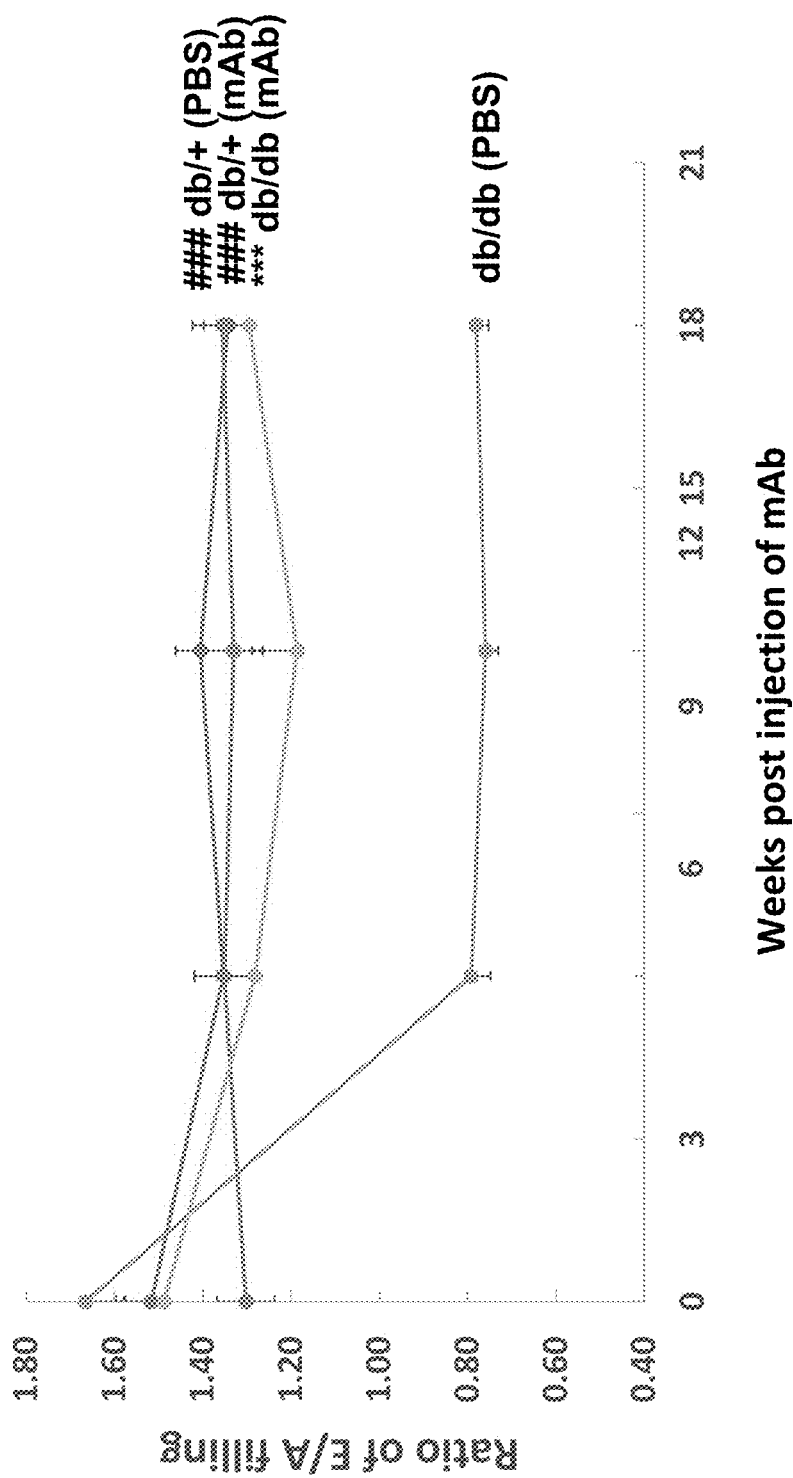
FIG. 24 is a line plot depicting the in vivo effects on the ratio of Early (E) to late (A) ventricular filling velocities (E/A) for the db/db (PBS), db/db (mAb), db/+ (PBS), and db/+ (mAb) groups throughout the 18 week study using repeated measurement ANOVA for statistical analysis. ***: p<0.0001 compared db/db (mAb) vs db/db (PBS); ###: p<0.0001 compare db/+ (PBS) or db/+ (mAb) vs db/db (PBS).
Figure 25:
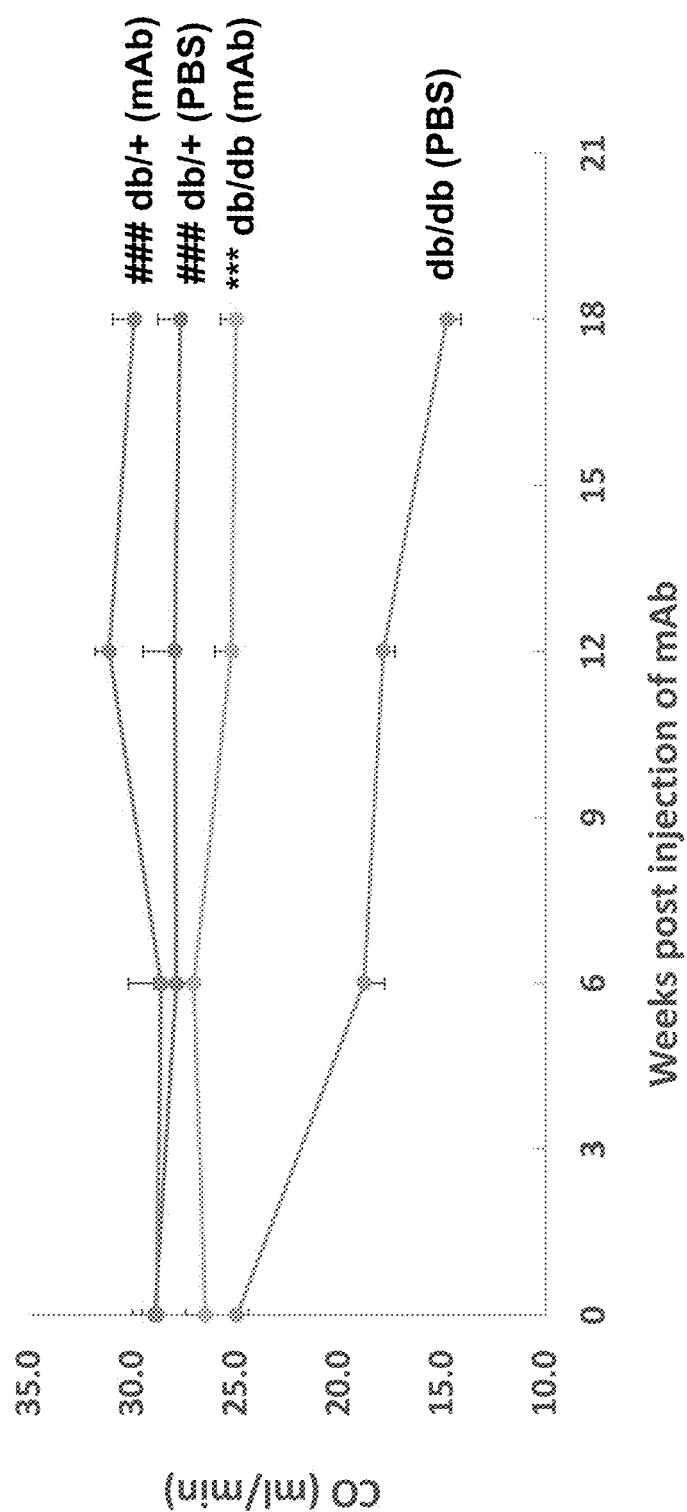
FIG. 25 is a line plot depicting the in vivo effects on Cardiac Output (CO, ml/min) for the db/db (PBS), db/db (mAb), db/+ (PBS), and db/+ (mAb) groups throughout the 18 week study using repeated measurement ANOVA for statistical analysis. ***: p<0.0001 compared db/db (mAb) vs db/db (PBS); ###: p<0.0001 compare db/+ (PBS) or db/+ (mAb) vs db/db (PBS).
Figure 26:
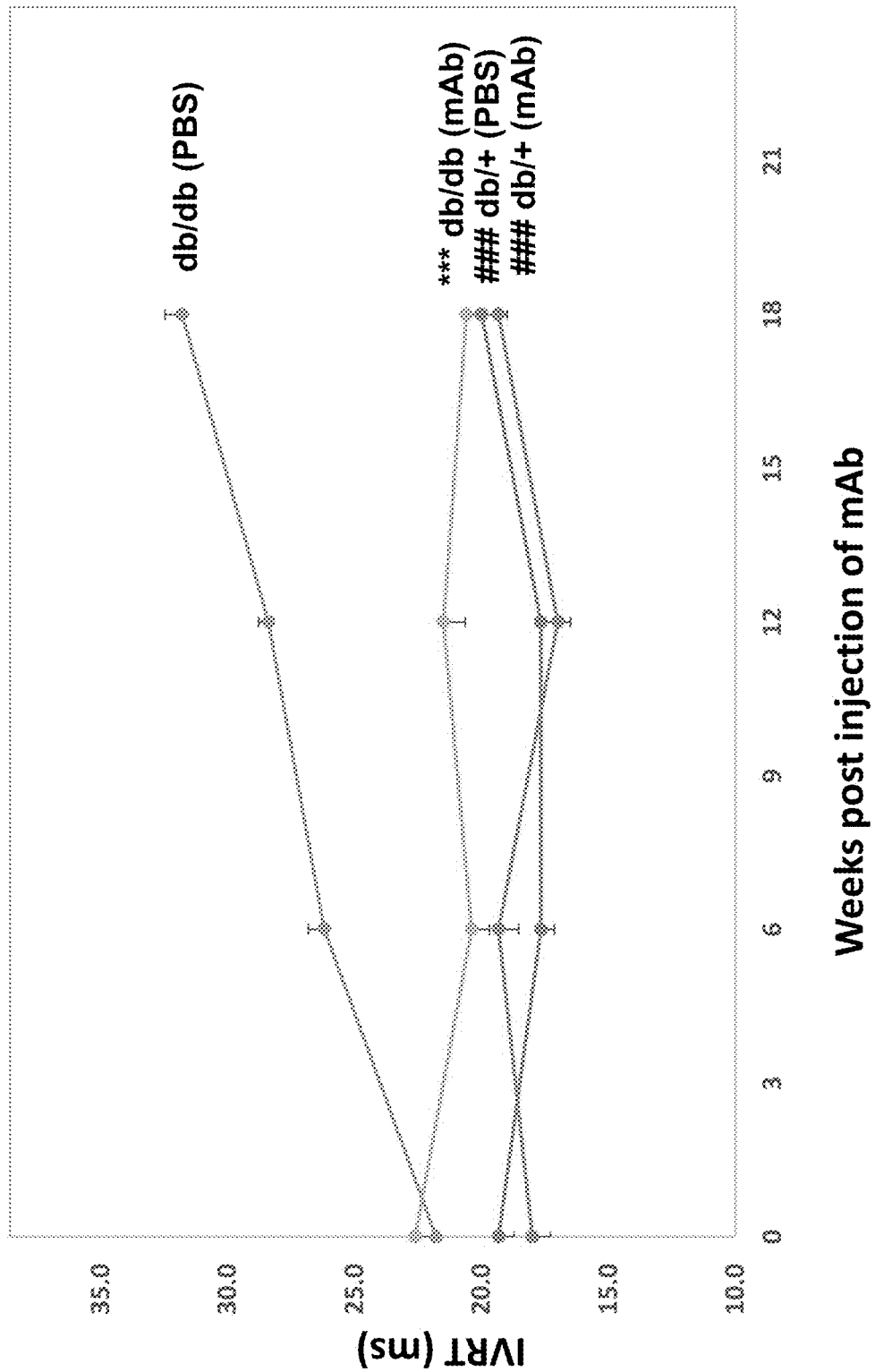
FIG. 26 is a line plot depicting the in vivo effects on Isovolumic Relaxation Time (IVRT, ms) for the db/db (PBS), db/db (mAb), db/+ (PBS), and db/+ (mAb) groups throughout the 18 week study using repeated measurement ANOVA for statistical analysis. ***: p<0.0001 compared db/db (mAb) vs db/db (PBS); ###: p<0.0001 compare db/+ (PBS) or db/+ (mAb) vs db/db (PBS).
Figure 27:
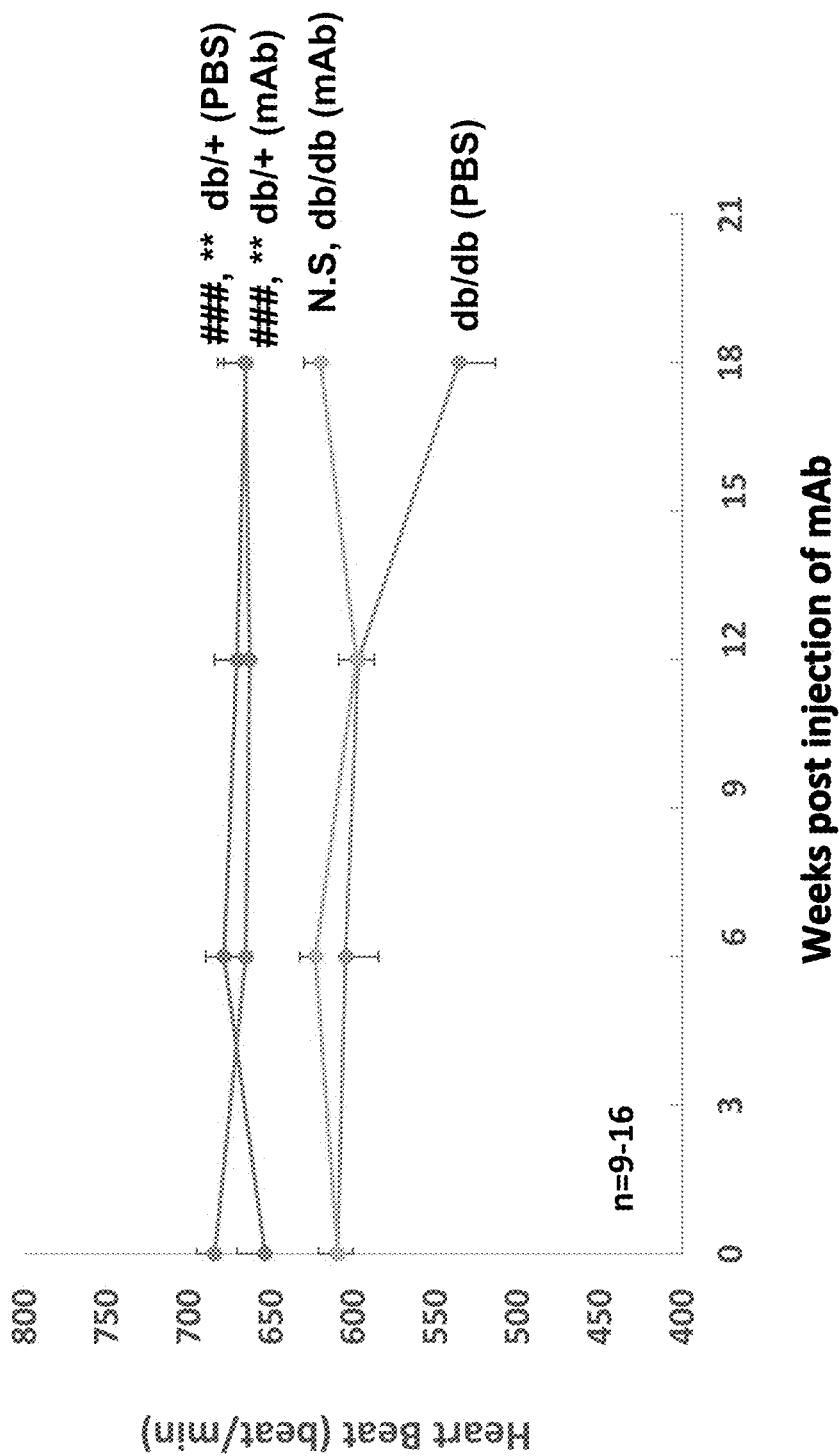
FIG. 27 is a line plot depicting the in vivo effects on Heart Beat Rate (HR, beat/min) for the db/db (PBS), db/db (mAb), db/+ (PBS), and db/+ (mAb) groups throughout the 18 week study using repeated measurement ANOVA methods. P values: N.S: there is no statistical significant differences compare db/db (mAb) vs. db/db (PBS) group; ###: p<0.0001, compared db/+ (PBS) or db/+ (mAb) vs. db/db (PBS) group; **: compared db/+ (PBS) or db/+ (mAb) vs. db/db (mAb) group.
Figure 28:
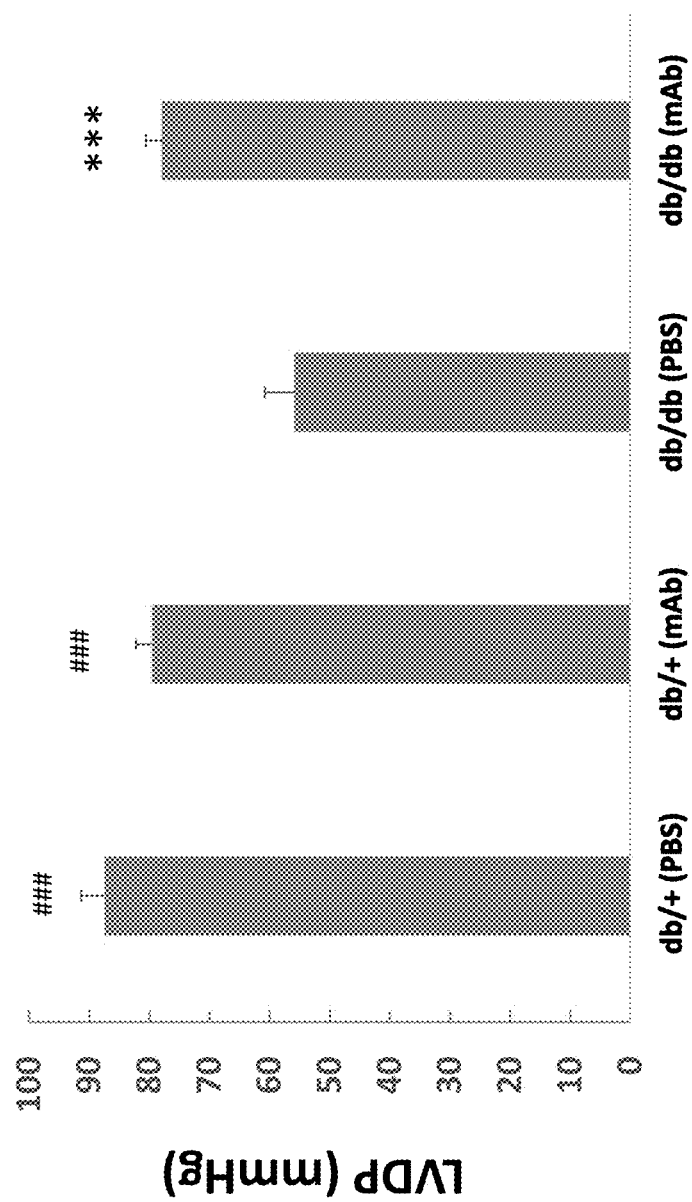
FIG. 28 is a bar graph depicting in vivo effects on Left ventricular diastole pressure (LVDP, mmHg) measured by Mikro-tip catheter for the db/db (PBS), db/db (mAb), db/+ (PBS), and db/+ (mAb) groups at week 18 week. ***: p<0.0001 compared to db/db(PBS); ###: p<0.001 compared to db/db (PBS).
Figure 29:
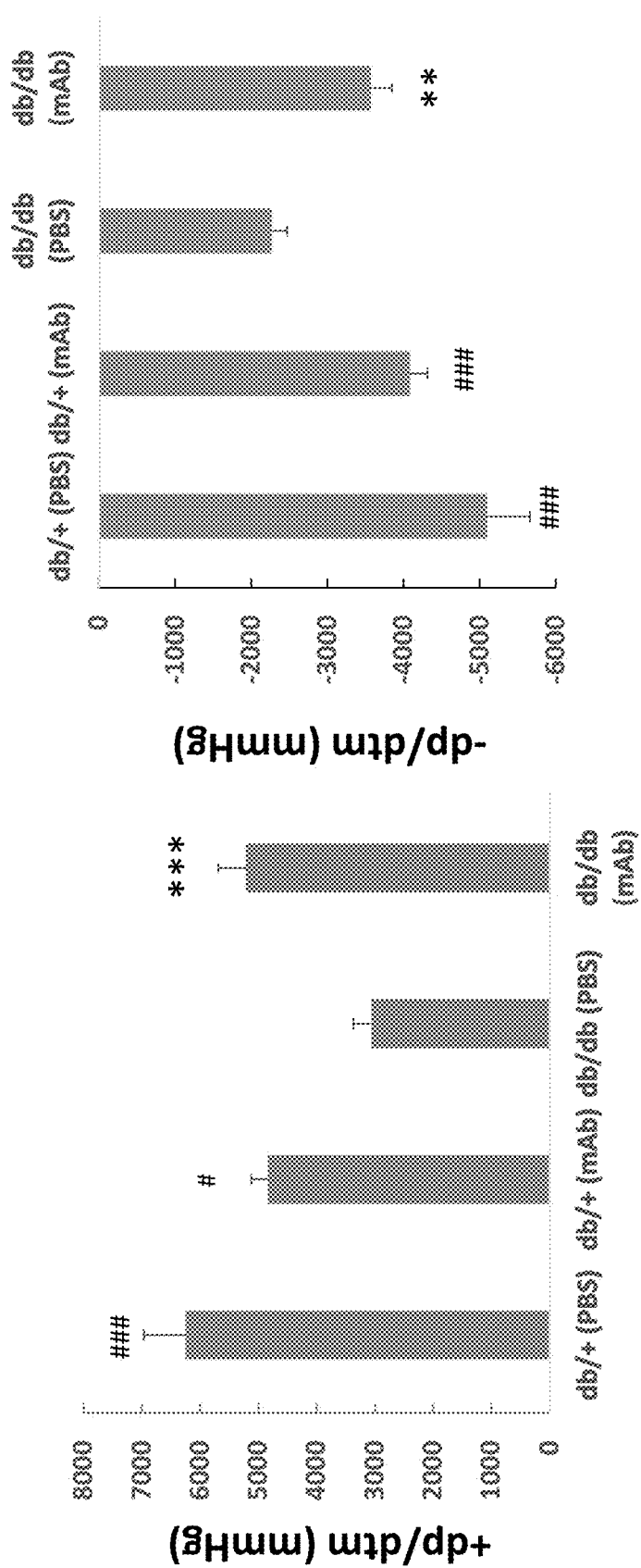
FIG. 29 is a bar graph depicting in vivo effects on +dp/dtm and −dp/dtm values (measured by Mikro-tip catheter) for the db/db (PBS), db/db (mAb), db/+ (PBS), and db/+ (mAb) groups at week 18 using repeated measurement ANOVA methods. *: p<0.0001. : p<0.01 compared to db/db (PBS); #: p<0.05; ###: p<0.001 compared to db/db (PBS).
Figure 30:
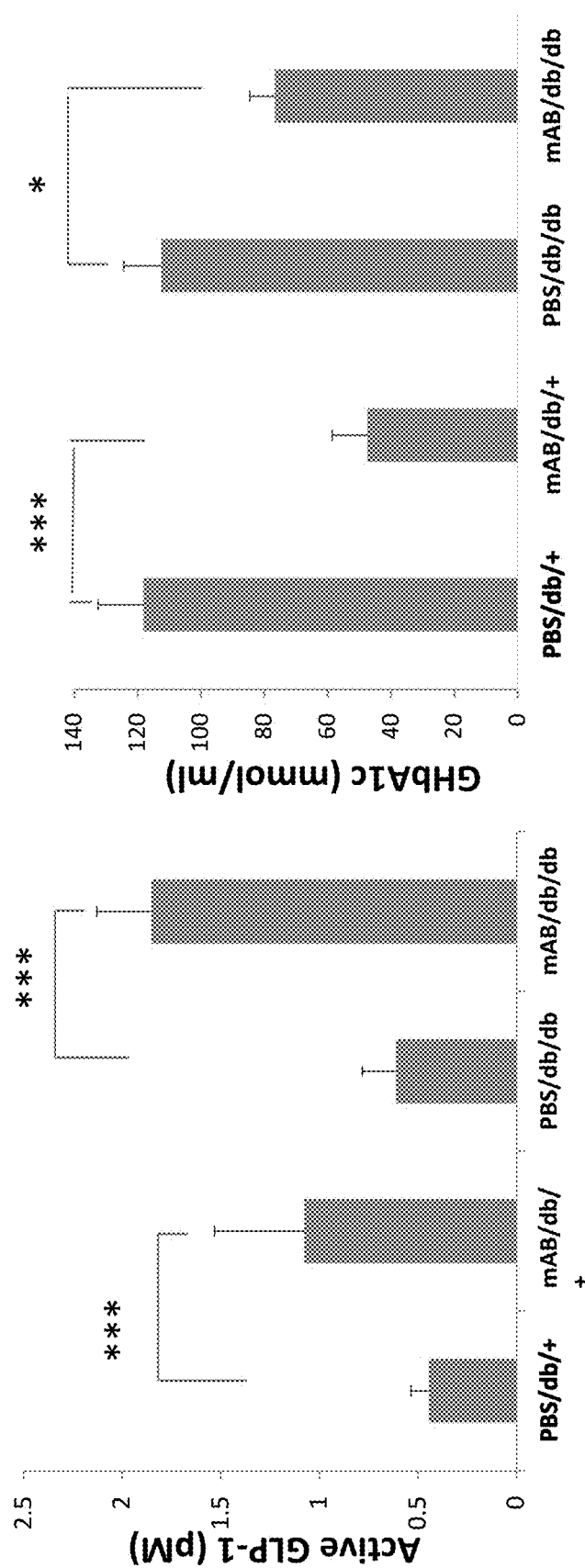
FIG. 30 is a bar graph depicting in vivo effects on serum active GLP-1 and GHbAc1 levels for the db/db (PBS), db/db (mAb), db/+ (PBS), and db/+ (mAb) groups at week 18 using repeated measurement ANOVA methods. P values, * p<0.05; ***: p<0.001.
Figure 31:
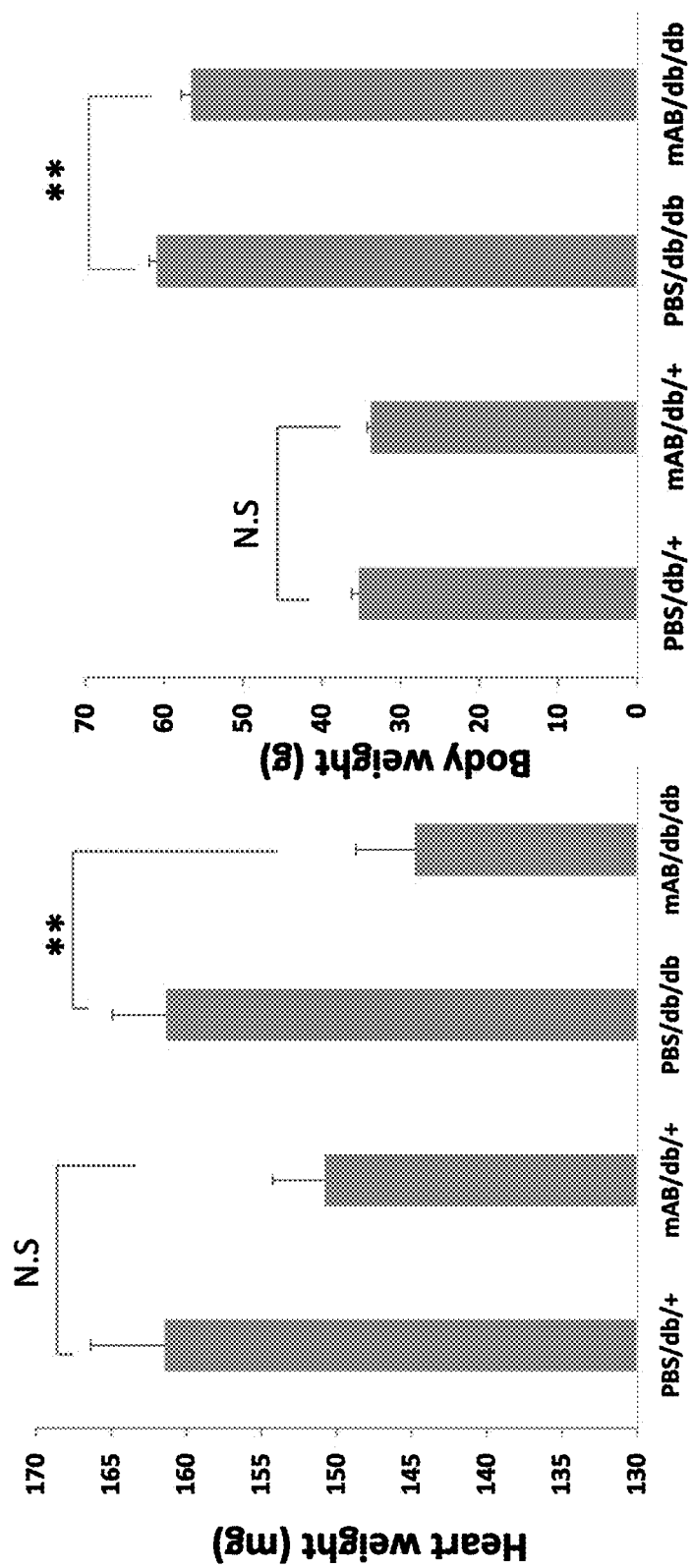
FIG. 31 is a bar graph depicting in vivo effects on heart weight and body weight for the db/db (PBS), db/db (mAb), db/+ (PBS), and db/+ (mAb) groups at week 18 using repeated measurement ANOVA methods. P values: **: p<0.01, N.S: no significant difference.
Figure 32:
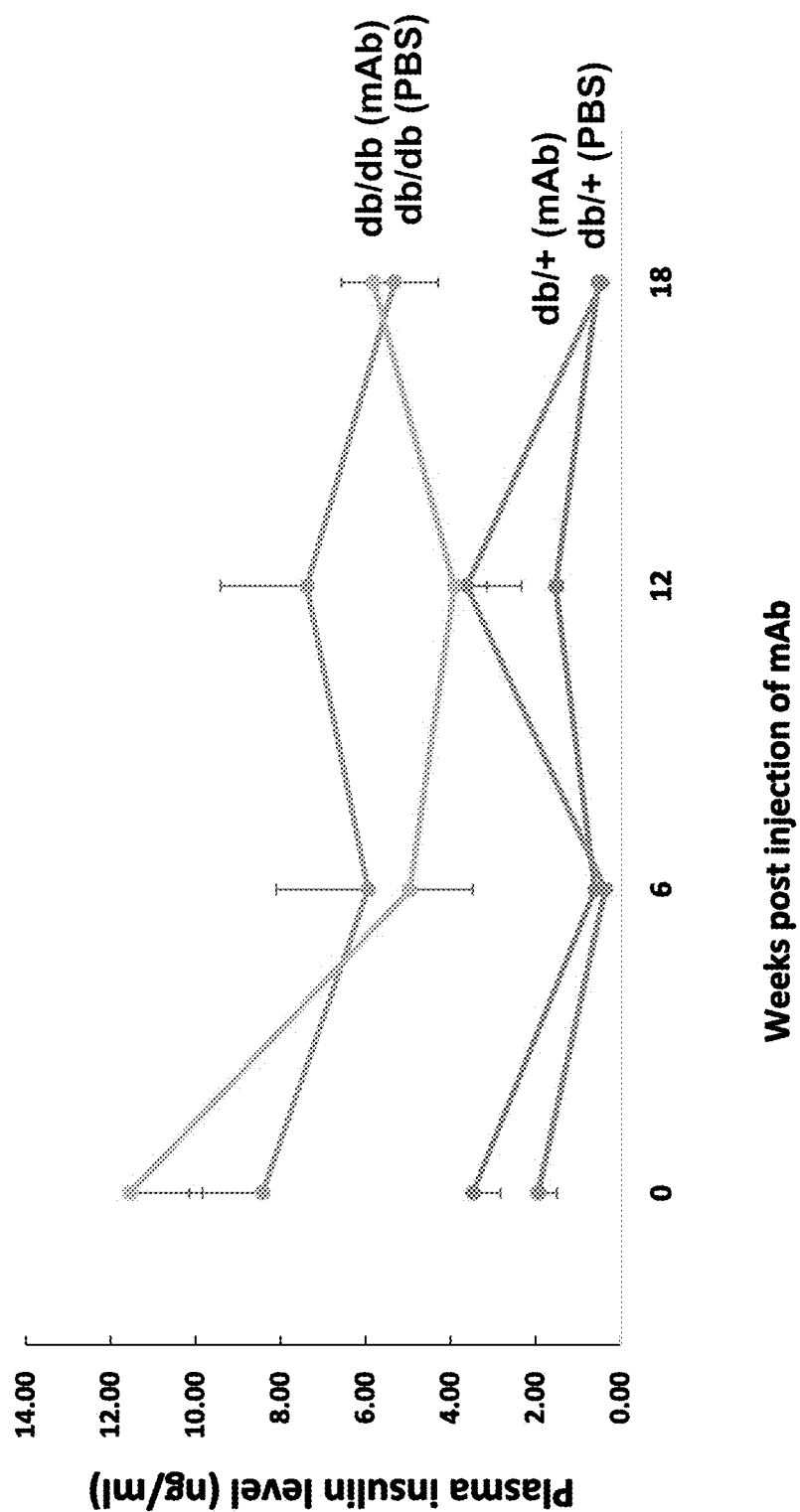
FIG. 32 is a bar graph depicting in vivo effects on blood insulin levels (ng/ml) post treatment at week 18 for the db/db (PBS), db/db (mAb), db/+ (PBS), and db/+ (mAb) using repeated measurement ANOVA methods.

As depicted in FIG. 18, mAb has significant effects on lowering fast blood glucose levels, and is capable of returning blood concentrations to normal as early as 3-4 weeks and capable of maintaining normal levels for 14 weeks, without insulin. As depicted in FIG. 19, the OGTT showed that the glucose tolerance capacity has been significantly improved. As depicted in FIG. 20, mAb markedly attenuated left ventricular dilation (LVESD) as compared to PBS in the diabetic db/db mice, restored values to that of control db/+ mice and maintained the values for 18 weeks. As depicted in FIG. 21, mAb attenuated left ventricular end diastolic dimension (LVEDD) as compared to PBS at 18 weeks. As depicted in FIG. 22, mAb significantly increased left ventricular fractional shortening (FS) as compared to PBS in the diabetic db/db, restored values to that of control db/+ mice and maintained the values for 18 weeks. As depicted in FIG. 23, mAb markedly attenuated interventricular septal end diastole (IVSD) as compared to PBS in the diabetic db/db mice, restored values to that of control db/+ mice and maintained the values for 18 weeks. As depicted in FIG. 24, mAb markedly reduced the ratios of Early (E) to late (A) ventricular filling velocities (E/A) as compared to PBS in the diabetic db/db mice, restored values to that of control db/+ mice and maintained the values for 18 weeks. As depicted in FIG. 25, mAb markedly increased Cardiac Output (CO, ml/min) as compared to PBS in the diabetic db/db mice, restored values to that of control db/+ mice and maintained the values for 18 weeks. As depicted in FIG. 26, mAb markedly reduced Isovolumic Relaxation Time (IVRT, ms) as compared to PBS in the diabetic db/db mice, restored values to that of control db/+ mice and maintained the values for 18 weeks. As depicted in FIG. 27, there was no statistical significant difference on heart beat rate for mAb compared to PBS control. As depicted in FIG. 28, mAb markedly increased left ventricular diastole pressure (LVDP, mmHg, measured by Mikro-tip catheter) as compared to PBS in the diabetic db/db mice at week 18, and restored values to nearly that of control db/+ mice. As depicted in FIG. 29, +dp/dtm and −dp/dtm values were markedly improved by treatment of mAb as compared to PBS at week 18 and mAb restored values to nearly that of control db/+ mice. As depicted in FIG. 30, after treatment using mAb, the blood GLP-1 was significantly elevated compared to PBS treated db/db mice, and the blood GHbA1c was significantly decreased compared to PBS treated db/db mice. As depicted in FIG. 31, mAb treatment resulted in a small reduction in heart weight and body weight compared to PBS at week 18. As depicted in FIG. 32, there was no significant differences between treatment groups in blood insulin levels at week 18.

Histology findings strongly support the potential preventive efficacy of an anti-glucagon receptor mAb against cardiomyopathy induced by diabetes. The surprising results of these studies suggest that glucagon signaling is involved in cardiomyopathy induced by diabetes and demonstrate that targeting glucagon receptor with an antagonistic mAb may be an effective therapeutic approach to prevention of cardiomyopathy induced by diabetes.

Example 3

In this example, the in vivo activity of an anti-GCGR antibody which comprises the heavy chain sequence set forth in SEQ ID NO: 8 and the light chain sequence set forth in SEQ ID NO: 9 ("REMD2.59C") is evaluated for efficacy in a miniature swine myocardial infarct model (Sinclair Research).

Miniature swine (young adult/female) are given a 7 day acclimation period and randomly divided into two groups. In Group 1, the swine are treated with a single dose of vehicle PBS as a control (CON, n=5) and in Group 2, the swine are treated with a single dose of 7.5 mg/kg REMD2.59C mAb (mAb, n=5). Prior to dose administration, each animal undergoes surgery (ligation of left ascending artery for 10-20 minutes) to create an occlusion and induce myocardial infarction. After 20 minutes, the occlusion is removed and the treatment administered during the reperfusion. The animals are maintained and handled in a stress-free environment post-op.

Mortality/Morbidity observations are made twice daily. Various assessments and parameters are made at baseline and prior to termination or necropsy. These include body weight, clinical observations, clinical pathology, clinical chemistry, hematology and coagulation parameters, and ECG/cardiac assessments. At the end of the study (28 days), limited necropsy is performed and limited heart tissue collected for histopathology (the middle of the infarct, the injected area and one more at each extent of the infarcted area is evaluated) for histological studies and ventricular contraction (echo FS/EF), ventricular pressure and contractility (catheter); ventricular remodeling, septum and LV wall thickness (echo), cardiac index (HW/BW), myocyte hypertrophy, fibrosis; infarct size, and apoptosis were determined.

Troponin level, size of ventricle, thickness of ventricle walls, and ejection fraction by echocardiogram are the end points.

Additional Materials and Methods
Preparation of Infarcted Mice

MI was induced in mice as described previously (Patten R D et al., Am J Physiol., 1998; 274:H1812-1820. [PubMed: 9612394]). Briefly, the chest was opened via a left thoracotomy. The left coronary artery was identified visually using a stereo microscope, and a 7-0 suture was placed around the artery 1-2 mm below the left auricle. The electrocardiogram (ECG) was monitored continuously. Permanent occlusion of the left coronary artery resulted from its ligation with the suture. Myocardial ischemia was confirmed by pallor in heart color and ST-segment elevation. The chest was closed with 6-0 silk suture. Once spontaneous respiration resumed, the endotracheal tube was removed. The animals were monitored until fully conscious. After they were returned to their cages, standard chow and water were provided.

Echocardiography

In vivo cardiac function was assessed by transthoracic echocardiography (Acuson P300, 18 MHz transducer; Siemens) in conscious mice, as described previously. The mouse heart was imaged in the two-dimensional mode in the parasternal short axis at a papillary level. From this view, LV chamber dimensions were measured. Fractional shortening (FS) was calculated from left ventricular (LV) end-diastolic diameter (EDD) and end-systolic diameter (ESD). M-mode EDD and ESD were averaged from three to five beats. Studies and analyses were performed by investigators blinded to treatments.

Measurement of LV Pressure by Mikro-Tip Catheter

Mice were anesthetized with pentobarbital (40 mg/kg, ip). The chest was opened via a left thoracotomy. The infarcted heart was exposed. A mouse Mikro-tip catheter (SPR1000) was inserted into the left ventricle through non-infarcted ventricular wall. LV pressure was measured by PowerLab system (Adinstruments). Ventricular contractility was calculated through Chart 7 software (Adinstruments).

Histological Studies

Hearts were fixed with 10% buffered formalin, embedded in paraffin, and sectioned at 6 μm. One middle longitudinal section per heart was stained with Masson's trichrome. Eight randomly selected fields (400×) from the non-infarct area in the left ventricle were examined for fibrosis and myocyte size under a microscope. Each group comprised 5-6 hearts, and minimal 40 fields were analyzed in each group by computerized planimetry (NIH Image J). To assess fibrosis, fibrotic blue area and whole myocardial area were measured. The fibrotic area was presented as a percentage of fibrotic area to the myocardial area. Myocyte size was measured in cross-sectioned muscle cells. Total 100-150 cells/heart were analyzed. Two methods were used to assess the size of the infarcted heart. Infarct area was calculated as a percentage of infarcted ventricular area to total ventricular area using the front and back sides of the heart photos. Infarct size was measured as a percentage of infarcted ventricular wall length to total ventricular wall length using cardiac sections. The observer was blinded to the origin of the cardiac sections.

TUNEL Assay

TUNEL assay was performed with the In Situ Apoptosis Detection Kit. Briefly, hearts were fixed by perfusion with 10% formalin solution, embedded in paraffin, and sectioned at 6 μm. One middle longitudinal section per heart was taken for TUNEL staining. Proteinase K (20 μg/ml) was added to each slide. Endogenous peroxidases was inactivated by covering sections with 2% hydrogen peroxide. After fixation, sections were incubated with TdT buffer at 37° C. for 30 min. Reactions were terminated with 1×SSC. After being washed, slides were incubated with RTU streptavidin-HRP for 30 min. Positive signal was developed by adding DAB solution. After counterstained with RTU hematoxylin, slides were covered by mounting medium and analyzed under a microscope. Each group comprised 5-6 hearts. Eight fields (400×) from the infarct area per heart were analyzed for positive cells and total cells using computerized planimetry (NIH Image J). The degree of apoptosis was presented as a percentage of positive cells to total cells.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

SEQUENCE LISTINGS

The amino acid sequences listed in the accompanying sequence listing are shown using standard three letter code for amino acids, as defined in 37 C.F.R. 1.822.

SEQ ID NO: 1 is the amino acid sequence of a human glucagon receptor (GCGR) molecule (Accession Number AAI04855).

SEQ ID NO: 2 is the amino acid sequence encoding the heavy chain variable region of a fully human anti-GCGR antibody. SEQ ID NO: 3 is the amino acid sequence encoding the light chain variable region of a fully human anti-GCGR antibody.

SEQ ID NO: 4 is the amino acid sequence encoding the heavy chain variable region of a fully human anti-GCGR antibody. SEQ ID NO: 5 is the amino acid sequence encoding the light chain variable region of a fully human anti-GCGR antibody.

SEQ ID NO: 6 is the amino acid sequence encoding the heavy chain variable region of a fully human anti-GCGR antibody. SEQ ID NO: 7 is the amino acid sequence encoding the light chain variable region of a fully human anti-GCGR antibody.

SEQ ID NO: 8 is the amino acid sequence encoding the heavy chain of a chimeric anti-GCGR antibody. SEQ ID NO: 9 is the amino acid sequence encoding the light chain of a chimeric anti-GCGR antibody.

SEQ ID NOS: 10-28 are amino acid sequences encoding the heavy chain variable regions of various fully human anti-GCGR antibodies.

SEQ ID NOS: 29-47 are amino acid sequences encoding the light chain variable regions of various fully human anti-GCGR antibodies.

SEQ ID NO: 48 is the amino sequence encoding the kappa light chain constant region. SEQ ID NO: 49 is the amino sequence encoding the lambda light chain constant region.

SEQ ID NO: 50 is the amino acid sequence encoding the IgG2 heavy chain constant region.

SEQ ID NO: 51 is the amino acid sequence encoding the heavy chain of a human anti-GCGR antibody. SEQ ID NO: 52 is the amino acid sequence encoding the light chain of a human anti-GCGR antibody.

```
SEQUENCE LISTINGS

SEQ ID NO: 1-Amino acid sequence of a human glucagon receptor (GCGR) molecule
MPPCQPQRPLLLLLLLLACQPQVPSAQVMDFLFEKWKLYGDQCHHNLSLLPPPTELVCNRTFD
KYSCWPDTPANTTANISCPWYLPWHHKVQHRFVFKRCGPDGQWVRGPRGQPWRDASQCQ
MDGEEIEVQKEVAKMYSSFQVMYTVGYSLSLGALLLALAILGGLSKLHCTRNAIHANLFASFVLK
ASSVLVIDGLLRTRYSQKIGDDLSVSTWLSDGAVAGCRVAAVFMQYGIVANYCWLLVEGLYLH
NLLGLATLPERSFFSLYLGIGWGAPMLFVVPWAVVKCLFENVQCWTSNDNMGFWWILRFPVFL
AILINFFIFVRIVQLLVAKLRARQMHHTDYKFRLAKSTLTLIPLLGVHEVVFAFVTDEHAQGTLRSA
KLFFDLFLSSFQGLLVAVLYCFLNKEVQSELRRRWHRWRLGKVLWEERNTSNHRASSSPGHG
PPSKELQFGRGGGSQDSSAETPLAGGLPRLAESPF SEQ ID NO: 2-Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSS SEQ ID NO: 3-Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIK SEQ ID NO: 4-Amino acid sequence of a HCVR of a human antibody that binds GCGR
QVQLVESGGGVVQPGRSLRLSCAASGFTFSSYGMHWVRQAPGKGLEWV
AVMWYDGSNKDYVDSVKGRFTISRDNSKNTLYLQMNSLRAEDTAVYYCAREKDHYDI
LTGYNYYYGLDVWGQGTTVTVSS SEQ ID NO: 5-Amino acid sequence of a LCVR of a human antibody that binds GCGR
DIQMTQSPSSLSASVGDRVTITCRASQGIRNDLGWYQQKPGKAPKRLIYAASSLQSGV
PSRFSGSGSGTEFTLTISSLQPEDFVTYYCLQHNSNPLTFGGGTKVEIK SEQ ID NO: 6-Amino acid sequence of a HCVR of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYNY
YYGLDVWGQGTTVTVSS
```

SEQUENCE LISTINGS

SEQ ID NO: 7-Amino acid sequence of a LCVR of a human antibody that binds GCGR
DIQMTQSPSSLSASVGDRVTITCRASQGIRNDLGWYQQKPGKAPKRLIYAASSLESGV
PSRFSGSGSGTEFTLTISSVQPEDFVTYYCLQHNSNPLTFGGGTKVEIK SEQ ID NO: 8-Amino acid sequence of a heavy chain of a chimeric antibody that
binds GCGR
MEFGLSWVFLVALLRGVQCQVQLVESGGGVVQPGRSLRLSCAASGFTFSSYGMHWVRQAPG
KGLEWVAVMWYDGSNKDYVDSVKGRFTISRDNSKNTLYLQMNRLRAEDTAVYYCAREKDHY
DILTGYNYYYGLDVWGQGTTVTVSSAKTTPPSVYPLAPGSAAQTNSMVTLGCLVKGYFPEPVT
VTWNSGSLSSGVHTFPAVLQSDLYTLSSSVTVPSSTWPSETVTCNVAHPASSTKVDKKIVPRD
CGCKPCICTVPEVSSVFIFPPKPKDVLTITLTPKVTCVVVDISKDDPEVQFSWFVDDVEHTAQT
QPREEQFNSTFRSVSELPIMHQDWLNGKEFKCRVNSAAFPAPIEKTISKTKGRPKAPQVYTIPP
PKEQMAKDKVSLTCMITDFFPEDITVEWQWNGQPAENYKNTQPIMDTDGSYFVYSKLNVQKS
NWEAGNTFTCSVLHEGLHNHHTEKSLSHSPGK SEQ ID NO: 9-Amino acid sequence of a light chain of a chimeric antibody that
binds GCGR
MDMRVPAQLLGLLLLWFPGARCDIQMTQSPSSLSASVGDRVTITCRASQGIRNDLGWYQQKP
GKAPKRLIYAASSLESGVPSRFSGSGSGTEFTLTISSVQPEDFVTYYCLQHNSNPLTFGGGTKV
EIKRADAAPTVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRNEC SEQ ID NO: 10-Amino acid sequence of a HCVR of a human antibody that binds GCGR
QVQLVESGGGVVQPGRSLRLSCAASGFTFSNYGMHWVRQAPGKGLEWVAVILSDGRNKYYA
DSVKGRFTISRDNSKNTLYLQMNSLRAEDTAVYYCARDDYEILTGYGYYGMDVWGQGTTVTV
SS SEQ ID NO: 11-Amino acid sequence of a HCVR of a human antibody that binds GCGR
QVQLVESGGGVVQPGRSLRLSCAASGFTFSSYGMHWVRQAPGKGLEWVAVILNDGRNKYYA
DSVKGRFTISRDNSKNTLYLQMNSLRAEDTAVYYCARDDYEILTGYGYYGMDVWGQGTTVTV
SS SEQ ID NO: 12-Amino acid sequence of a HCVR of a human antibody that binds GCGR
QVQLQQSGPGLVKPSQTLSLTCAISGDSVSSNGAAWNWIRQSPSRGLEWLGRTYYRSKWYY
DYAGSVKSRININPDTSKNQFSLQVNSVTPEDTAVYYCTRDRSSGWNEGYYYYGMDVWGQG
TTVTVSS SEQ ID NO: 13-Amino acid sequence of a HCVR of a human antibody that binds GCGR
QVQLVESGGGVVQPGRSLRLSCAASGFTFSSYDIHWVRQAPGKGLEWVAVLSSDGNNKYCA
DSVKGRFTISRDNSKNTLYLQMNSLRTEDTAVYYCAREEVYYDILTGYYDYYGMDVWGQGTTV
TVSS SEQ ID NO: 14-Amino acid sequence of a HCVR of a human antibody that binds GCGR
QVQLQESGPGLVKPSETLSLTCTVSGGSISTYFWTWIRQFPGKGLEWIGYIFYSGSTNYNPSLK
SRVTISVDTSKNQFSLKLSSVTAADTAVYYCAREGYYDILTGEDYSGMDVWGQGTTVTVSS SEQ ID NO: 15-Amino acid sequence of a HCVR of a human antibody that binds GCGR
QVQLQQSGPGLVKPSQILSLTCAISGDRVSSNGAAWNWIRQSPSRGLEWLGRTYYRSKWYD
YAGSVKSRININPDTSKNQFSLQVNSVTPEDTAVYYCARDRSSGWNEGYYYYGMDVWGQGT
TVTVSS SEQ ID NO: 16-Amino acid sequence of a HCVR of a human antibody that binds GCGR
QVQLQESGPGLVKPSETLSLTCTVSGGSISTYFWTWIRQFPGEGLEWIGYIFYSGNTNYNPSLT
SRVTISVDTSKNQFSLKLSSVTAADTAVYYCAREGYYDILTGEDYSGIDVWGQGTTVTVSS SEQ ID NO: 17-Amino acid sequence of a HCVR of a human antibody that binds GCGR
QVQLVESGGGVVQPGRSLRLSCAASGFIFSSYGMHWVRQAPGKGLEWVAVISNDGSNKYYA
DPVKGRFTISRDNSKNTLYLQMNSLRAEDTAVYYCAREDYDILTGNGVYGMDVWGQGTTVTV
SS SEQ ID NO: 18-Amino acid sequence of a HCVR of a human antibody that binds GCGR
EVQLVESGGGLVQPGGSLRLSCAASGFTFSSYTMNWVRQAPGKGLEWVSYISGSSSLIYYAD
SVKGRFTISRDNAKNSLYLHMNSLRDEDTAVYYCARARYNWNDYYGMDVWGQGTTVTVSS SEQ ID NO: 19-Amino acid sequence of a HCVR of a human antibody that binds GCGR
QVQLVESGGGVVQPGRSLRLSCAASGFAFSSYGIHWVRQAPGKGLEWVAGIWYDGSNKYYA
DSVKGRFTVSRDNSKNTLYLQMNSLRAEDTAVYYCARLFDAFDIWGQGTMVTVSS SEQ ID NO: 20-Amino acid sequence of a HCVR of a human antibody that binds GCGR
EVQLVESGGGLVQPGGSLRLSCAASGFIFSSYTMNWVRQAPGKGLEWVSYISSSSSLIYYADS
VKGRFTISRDNAKNSLYLQMNSLRDEDTAVYYCARSDYYGSGSYYKGNYYGMDVWGQGTTV
TVSS

SEQUENCE LISTINGS

SEQ ID NO: 21-Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 22-Amino acid sequence of a HCVR of a human antibody that binds GCGR
QVQLVESGGGVVQPGRSLRLSCAASGFTFSSYGMHWVRQAPGKGLEWVTIIWSDGINKYYAD
SVKGRFTISRDNSKNTLNLQMNSLRAEDTAVYYCARERGLYDILTGYYDYYGIDVWGQGTTVT
VSS SEQ ID NO: 23-Amino acid sequence of a HCVR of a human antibody that binds GCGR
EVQLVESGGGLVKPGGSLRLSCAASGITFRSYSMNWVRQAPGKGLEWVSAISSSSSYIYYADS
VKGRFTISRDNAKNSVYLQMNSLRAEDTAVYYCARGRYGMDVWGQGTTVTVSS SEQ ID NO: 24-Amino acid sequence of a HCVR of a human antibody that binds GCGR
QVQLVESGGGVVQPGRSLRLSCAASGTFRSYDMHWVRQAPGKGLEWVAVISYDGSNKYYG
DSVKGRLTISRDNSKNTLYLQMNSLRAEDTAVYYCARDQYDILTGYSSDAFDIWGQGTMVTV
SS SEQ ID NO: 25-Amino acid sequence of a HCVR of a human antibody that binds GCGR
QVQLVESGGGVVQPGRSLRLSCAASGFTFSRYGMHWVRQAPGKGLEWVAVIWYDGSHKYY
EDSVKGRFTISRDNSKNTLYLQMNSLRADDTGVYYCARVGYGSGWYEYYYHYGMDVWGQGT
TVTVSS SEQ ID NO: 26-Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 27-Amino acid sequence of a HCVR of a human antibody that binds GCGR
QVQLVESGGGVVQPGRSLRLSCAASGFTFSSYGMHWVRQAPGKGLEWVAVMWYDGSNKDY
VDSVKGRFTISRDNSKNTLYLQMNRLRAEDTAVYYCAREKDHYDILTGYNYYYGLDVWGQGTT
VTVSS SEQ ID NO: 28-Amino acid sequence of a HCVR of a human antibody that binds GCGR
QVQLVESGGGVVQPGRSLRLSCAASGITFSSYGMHWVRQAPGKGLEWVASIWYDGSNKYV
DSVKGRFTIFRDNSKKTLYLQMNRLRAEDTAVYYCARLGGGFDYWGQGTLVTVSS SEQ ID NO: 29-Amino acid sequence of a LCVR of a human antibody that binds GCGR
DIQMTQSPSSLSASVGDRVTITCRASQDISNYLAWFQKKPGKAPKSLIYVVSSLQSGVPSRFSG
SGSGTDFTLTINNLQPEDFATYYCQQYNHYPLTFGGGTRVEIKR SEQ ID NO: 30-Amino acid sequence of a LCVR of a human antibody that binds GCGR
DIQMTQSPSSLSASVGDRVTITCRASQDISNYLAWFQQRPGKAPKSLIYVVSSLQSGVPSRFSG
SGSGTDFTLTISNLQPEDFATYFCQQYNHYPLTFGGGTKVEIKR SEQ ID NO: 31-Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDIATYFCQQYDDLPLTFGGGTRVDIKR SEQ ID NO: 32-Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSLQPEDFATYYCLQHNSNPLTFGGGTKVEIKR SEQ ID NO: 33-Amino acid sequence of a LCVR of a human antibody that binds GCGR
QNVLTQSPGTLSLSPGERVTLSCRASQSVSSSYLAWYQQKPGQAPRLLIFGVSSRATGIPDRF
SGSGSGTDFSLTISRLEPEDFAVYYCQQYGNSPFTFGPGTKVDIKR SEQ ID NO: 34-Amino acid sequence of a LCVR of a human antibody that binds GCGR
DIQMTQFPSSLSASIGDRVTITCQASQDISNFLNWFQQKPGKAPKLLIYDASDLETGVPSRFSGS
GAGTDFTFTISSLQPEDVATYFCQQYDNLPLTFGGGTKVDIKR SEQ ID NO: 35-Amino acid sequence of a LCVR of a human antibody that binds GCGR
ENVLTQSPGTLSLSPGERATLSCRASQSVTSSYLAWYQQKPGQAPRLLIFGVSSRATGIPDRF
SGSGSGTDFSLTISRLEPEDFAVYYCQQYGNSPFTFGPGTKVDIKR SEQ ID NO: 36-Amino acid sequence of a LCVR of a human antibody that binds GCGR
DIQMTQSPSSLSASVGDRVTITCRASQGIDMYLAWFQQKPGKAPKSLIYAASSLQSGVPSKFS
GSGFGTDFTLTISSLQPEDFATYYCQQYNIFPFTFGPGTKVDVKR SEQ ID NO: 37-Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSLQPEDFATYYCLQHNSYPWTFGQGTKVEIKR

SEQUENCE LISTINGS

SEQ ID NO: 38-Amino acid sequence of a LCVR of a human antibody that binds GCGR
KIVMTQTPLALPVIPGEPASISCRSSQSLVDSDDGDTYLDWYLQKPGQSPQVLIHRLSYRASGV
PDRFSGSGSGTDFTLKISRVEAEDVGIYYCMHRIEFPFTFGGGTKVEIKR SEQ ID NO: 39-Amino acid sequence of a LCVR of a human antibody that binds GCGR
DIQMTQSPSSLSASVGDRVTITCRASQGIRNDLGWYQQRPGKAPKRLIYAASSLQTGVPSRFS
GSGSGTEFTLTISSLQPEDFATYYCLQHNSYPWTFGQGTKVEIKR SEQ ID NO: 40-Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMCSFGQGTKLEIKR SEQ ID NO: 41-Amino acid sequence of a LCVR of a human antibody that binds GCGR
GIVLTQSPLSLPVTPGEPASISCRSSQSLLHSNGYNYLDWYLQKPGQSPQLLIYLGSNRASGVP
DRFSGSGSGTDFTLKISRVEAEDVGVYYCMEALQTMSSFGQGTKLEIKR SEQ ID NO: 42-Amino acid sequence of a LCVR of a human antibody that binds GCGR
DIVMTQTPLFLPVTPGEPASISCRSSQTLLDSDDGNTYLDWYLQKPGQSPQRLIYTLSYRASGV
PDRFSGSGSGTDFTLKISRVEAEDVGIYYCMQHIEFPSTFGQGTRLEIKR SEQ ID NO: 43-Amino acid sequence of a LCVR of a human antibody that binds GCGR
SYELTQPPSVSVSPGQTASITCSGDKLGDKYASWYQQKPGQSPVLVIYQSTKRPSGIPERFSG
SNSGNTATLTISGTQAMDEADYYCQAWDSSTVVFGGGTKLTVLG SEQ ID NO: 44-Amino acid sequence of a LCVR of a human antibody that binds GCGR
NIVMTQTPLSLSVTPGQPASISCKSSQSLLHSDGKNYLFWYLQKPGQSPQLLIYEVSYRFSGVP
DRFSGSGSGTDFSLKISRVEAEDVGVYYCMQNIQPPLTFGQGTRLEIKR SEQ ID NO: 45-Amino acid sequence of a LCVR of a human antibody that binds GCGR
DIQMTQSPSSLSASVGDRVTITCRASQGIRNDLGWYQQKPGKAPKRLIYAASSLQSGVPSRFS
GSGSGTEFTLTISSVQPEDFVTYYCLQHNSNPLTFGGGTKVEIKR SEQ ID NO: 46-Amino acid sequence of a LCVR of a human antibody that binds GCGR
DIQMTQSPSSLSASVGDRVTITCRASQGIRNDLGWYQQKPGKAPKRLIYAASSLESGVPSRFS
GSGSGTEFTLTISSVQPEDFVTYYCLQHNSNPLTFGGGTKVEIKR SEQ ID NO: 47-Amino acid sequence of a LCVR of a human antibody that binds GCGR
DIVLTQTPLSLPVTPGEPASISCRSSQSLLDRDDGDTYLDWYLQKPGQSPQLLIYTLSYRASGV
PDRFSGSGSGTDFSLKISRVEAEDVGVYYCMQRIEFPFTFGPGTKVDIKR SEQ ID NO: 48-Amino acid sequence of the constant light chain kappa region
RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO: 49-Amino acid sequence of the constant light chain lambda region
GQPKAAPSVTLFPPSSEELQANKATLVCLISDFYPGAVTVAWKADSSPVKAGVETTTPSKQSN
NKYAASSYLSLTPEQWKSHRSYSCQVTHEGSTVEKTVAPTECS SEQ ID NO: 50-Amino sequence of the IgG2 heavy chain constant region
ASTKGPSVFPLAPCSRSTSESTAALGCLVKDYFPEPVTVSWNSGALTSGVHTFPAVLQSSGLY
SLSSVVTVPSSNFGTQTYTCNVDHKPSNTKVDKTVERKCCVECPPCPAPPVAGPSVFLFPPKP
KDTLMISRTPEVTCVVVDVSHEDPEVQFNWYVDGVEVHNAKTKPREEQFNSTFRVVSVLTVVH
QDWLNGKEYKCKVSNKGLPAPIEKTISKTKGQPREPQVYTLPPSREEMTKNQVSLTCLVKGFY
PSDIAVEWESNGQPENNYKTTPPMLDSDGSFFLYSKLTVDKSRWQQGNVFSCSVMHEALHNH
YTQKSLSLSPGK SEQ ID NO: 51-Amino acid sequence of a HC of a human antibody that binds GCGR
QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSSASTKGPSVFPLAPCSRSTSESTAALGCLVKDYFPEPVTVSWN
SGALTSGVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSHEDPEVQFNWYVDGVEVHNAKT
KPREEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVDKS
RWQQGNVFSCSVMHEALHNHYTQKSLSLSPGK SEQ ID NO: 52-Amino acid sequence of a LC of a human antibody that binds GCGR
DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIKRTVAAPSVFIF
PPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC

What is claimed is:

1. A method for treating heart failure in a subject in need thereof comprising administering to the subject a therapeutically effective amount of an isolated antagonistic antigen binding protein that specifically binds to the human glucagon receptor, wherein the antagonistic antigen binding protein is selected from: (a) a human anti-GCGR antibody which comprises the amino acid sequence encoding the heavy chain variable region of SEQ ID NO: 2 and the amino acid sequence encoding the light chain variable region of SEQ ID NO: 3; (b) a human anti-GCGR antibody which comprises the amino acid sequence encoding the heavy chain variable region of SEQ ID NO: 4 and the amino acid sequence encoding the light chain variable region of SEQ ID NO: 5; (c) a human anti-GCGR antibody which comprises the amino acid sequence encoding the heavy chain variable region of SEQ ID NO: 6 and the amino acid sequence encoding the light chain variable region of SEQ ID NO: 7; (d) a human anti-GCGR antibody which comprises a heavy chain variable region having the amino acid sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28; and a human anti-GCGR antibody which comprises a light chain variable region having the amino acid sequence selected from the group consisting of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47; or (e) a human anti-GCGR antibody which comprises the amino acid sequence encoding the heavy chain variable region of SEQ ID NO: 28 and the amino acid sequence encoding the light chain variable region of SEQ ID NO: 47.

2. A method according to claim 1, wherein the heart failure to be treated is selected from the group consisting of post-myocardial infarction heart failure and diabetic cardiomyopathy heart failure.

3. A method according to claim 2, wherein the heart failure to be treated is post-myocardial infarction heart failure.

4. A method according to claim 2, wherein the heart failure to be treated is diabetic cardiomyopathy heart failure.

5. A method according to claim 1, wherein the therapeutically effective amount of the isolated antagonistic antigen binding protein is selected from: 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 0.5 to 50 mg/kg, 0.5 to 40 mg/kg, 0.5 to 30 mg/kg, 0.5 to 20 mg/kg, 0.5 to 10 mg/kg, 0.5 to 5 mg/kg, 0.5 to 4 mg/kg, 0.5 to 3 mg/kg, 0.5 to 2 mg/kg, 0.5 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, and 1 mg/kg body weight per week.

6. A method according to claim 5, wherein the therapeutically effective amount of the isolated antagonistic antigen binding protein is 0.01 to 10 mg/kg body weight per week.

7. A method according to claim 1, said method further comprising administering an anti-heart failure drug to the subject, wherein the ant-heart failure drug is selected from a group consisting of: angiotensin-converting enzyme (ACE) inhibitors, β-adrenergic blocking agents, angiotensin II receptor blockers (ARBs), diuretics, and digitalis.

8. A method according to claim 1, wherein the isolated antagonistic antigen binding protein is admixed with a pharmaceutically acceptable carrier to form a pharmaceutical composition for systemic administration to the subject.

9. A method according to claim 8, wherein the systemic administration is selected from: intravenous injection, intramuscular injection, subcutaneous injection, intraperitoneal injection, transdermal injection, intraarterial injection, intrasternal injection, intrathecal injection, intraventricular injection, intraurethral injection, intracranial injection, intrasynovial injection or via infusions.

10. A method of treating lateral ventricular (LV) remodeling comprising administration of a therapeutically effective amount of an isolated antagonistic antigen binding protein that specifically binds to the human glucagon receptor, wherein the antagonistic antigen binding protein is selected from: (a) a human anti-GCGR antibody which comprises the amino acid sequence encoding the heavy chain variable region of SEQ ID NO: 2 and the amino acid sequence encoding the light chain variable region of SEQ ID NO: 3; (b) a human anti-GCGR antibody which comprises the amino acid sequence encoding the heavy chain variable region of SEQ ID NO: 4 and the amino acid sequence encoding the light chain variable region of SEQ ID NO: 5; (c) a human anti-GCGR antibody which comprises the amino acid sequence encoding the heavy chain variable region of SEQ ID NO: 6 and the amino acid sequence encoding the light chain variable region of SEQ ID NO: 7; (d) a human anti-GCGR antibody which comprises a heavy chain variable region having the amino acid sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28; and a human anti-GCGR antibody which comprises a light chain variable region having the amino acid sequence selected from the group consisting of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47; or (e) a human anti-GCGR antibody which comprises the amino acid sequence encoding the heavy chain variable region of SEQ ID NO: 28 and the amino acid sequence encoding the light chain variable region of SEQ ID NO: 47.

11. A method according to claim 10, said method further comprising administering an anti-heart failure drug to the subject, wherein the ant-heart failure drug is selected from a group consisting of: angiotensin-converting enzyme (ACE) inhibitors, β-adrenergic blocking agents, angiotensin II receptor blockers (ARBs), diuretics, and digitalis.

* * * * *

SEQUENCE LISTING

<160> NUMBER OF SEQ ID NOS: 52

<210> SEQ ID NO 1
<211> LENGTH: 477
<212> TYPE: PRT
<213> ORGANISM: Homo sapiens

<400> SEQUENCE: 1

```
Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365
```

```
Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Arg Asn Thr Ser Asn
                420                 425                 430

His Arg Ala Ser Ser Pro Gly His Gly Pro Ser Lys Glu Leu
                435                 440                 445

Gln Phe Gly Arg Gly Gly Ser Gln Asp Ser Ser Ala Glu Thr Pro
450                 455                 460

Leu Ala Gly Gly Leu Pro Arg Leu Ala Glu Ser Pro Phe
465                 470                 475
```

<210> SEQ ID NO 2
<211> LENGTH: 128
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125
```

<210> SEQ ID NO 3
<211> LENGTH: 107
<212> TYPE: PRT
<213> ORGANISM: Homo sapiens

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95
```

```
Thr Phe Gly Gly Gly Thr Lys Val Glu Ile Lys
            100                 105
```

<210> SEQ ID NO 4
<211> LENGTH: 128
<212> TYPE: PRT
<213> ORGANISM: Homo sapiens

<400> SEQUENCE: 4

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Met Trp Tyr Asp Gly Ser Asn Lys Asp Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125
```

<210> SEQ ID NO 5
<211> LENGTH: 107
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys
            100                 105
```

<210> SEQ ID NO 6
<211> LENGTH: 128
<212> TYPE: PRT
<213> ORGANISM: Homo sapiens

<400> SEQUENCE: 6

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
```

```
                35                  40                  45
Ala Val Met Trp Tyr Asp Gly Ser Asn Lys Asp Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Arg Leu Arg Ala Glu Asp Thr Ala Val Tyr Tyr Cys
                 85                  90                  95

Ala Arg Glu Lys Asp His Tyr Asp Ile Leu Thr Gly Tyr Asn Tyr Tyr
                100                 105                 110

Tyr Gly Leu Asp Val Trp Gly Gln Gly Thr Thr Val Thr Val Ser Ser
            115                 120                 125

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Val Gln Pro
 65                  70                  75                  80

Glu Asp Phe Val Thr Tyr Tyr Cys Leu Gln His Asn Ser Asn Pro Leu
                 85                  90                  95

Thr Phe Gly Gly Gly Thr Lys Val Glu Ile Lys
                100                 105

<210> SEQ ID NO 8
<211> LENGTH: 471
<212> TYPE: PRT
<213> ORGANISM: Artificial Sequence
<220> FEATURE:
<223> OTHER INFORMATION: heavy chain of a chimeric antibody that binds
      GCGR

<400> SEQUENCE: 8

Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Lys Gly Leu
 50                  55                  60

Glu Trp Val Ala Val Met Trp Tyr Asp Gly Ser Asn Lys Asp Tyr Val
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Arg Leu Arg Ala Glu Asp Thr Ala Val
                100                 105                 110

Tyr Tyr Cys Ala Arg Glu Lys Asp His Tyr Asp Ile Leu Thr Gly Tyr
```

```
                115                 120                 125
Asn Tyr Tyr Tyr Gly Leu Asp Val Trp Gly Gln Gly Thr Thr Val Thr
            130                 135                 140

Val Ser Ser Ala Lys Thr Thr Pro Pro Ser Val Tyr Pro Leu Ala Pro
145                 150                 155                 160

Gly Ser Ala Ala Gln Thr Asn Ser Met Val Thr Leu Gly Cys Leu Val
                165                 170                 175

Lys Gly Tyr Phe Pro Glu Pro Val Thr Val Thr Trp Asn Ser Gly Ser
            180                 185                 190

Leu Ser Ser Gly Val His Thr Phe Pro Ala Val Leu Gln Ser Asp Leu
        195                 200                 205

Tyr Thr Leu Ser Ser Ser Val Thr Val Pro Ser Ser Thr Trp Pro Ser
210                 215                 220

Glu Thr Val Thr Cys Asn Val Ala His Pro Ala Ser Ser Thr Lys Val
225                 230                 235                 240

Asp Lys Lys Ile Val Pro Arg Asp Cys Gly Cys Lys Pro Cys Ile Cys
                245                 250                 255

Thr Val Pro Glu Val Ser Ser Val Phe Ile Phe Pro Pro Lys Pro Lys
            260                 265                 270

Asp Val Leu Thr Ile Thr Leu Thr Pro Lys Val Thr Cys Val Val Val
        275                 280                 285

Asp Ile Ser Lys Asp Asp Pro Glu Val Gln Phe Ser Trp Phe Val Asp
290                 295                 300

Asp Val Glu Val His Thr Ala Gln Thr Gln Pro Arg Glu Glu Gln Phe
305                 310                 315                 320

Asn Ser Thr Phe Arg Ser Val Ser Glu Leu Pro Ile Met His Gln Asp
                325                 330                 335

Trp Leu Asn Gly Lys Glu Phe Lys Cys Arg Val Asn Ser Ala Ala Phe
            340                 345                 350

Pro Ala Pro Ile Glu Lys Thr Ile Ser Lys Thr Lys Gly Arg Pro Lys
        355                 360                 365

Ala Pro Gln Val Tyr Thr Ile Pro Pro Lys Glu Gln Met Ala Lys
370                 375                 380

Asp Lys Val Ser Leu Thr Cys Met Ile Thr Asp Phe Phe Pro Glu Asp
385                 390                 395                 400

Ile Thr Val Glu Trp Gln Trp Asn Gly Gln Pro Ala Glu Asn Tyr Lys
                405                 410                 415

Asn Thr Gln Pro Ile Met Asp Thr Asp Gly Ser Tyr Phe Val Tyr Ser
            420                 425                 430

Lys Leu Asn Val Gln Lys Ser Asn Trp Glu Ala Gly Asn Thr Phe Thr
        435                 440                 445

Cys Ser Val Leu His Glu Gly Leu His Asn His Thr Glu Lys Ser
    450                 455                 460

Leu Ser His Ser Pro Gly Lys
465                 470

<210> SEQ ID NO 9
<211> LENGTH: 236
<212> TYPE: PRT
<213> ORGANISM: Artificial Sequence
<220> FEATURE:
<223> OTHER INFORMATION: light chain of a chimeric antibody that binds
      GCGR

<400> SEQUENCE: 9
```

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
50                  55                  60

Ala Pro Lys Arg Leu Ile Tyr Ala Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235

<210> SEQ ID NO 10
<211> LENGTH: 125
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Leu Ser Asp Gly Arg Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
        115                 120                 125

<210> SEQ ID NO 11

```
<211> LENGTH: 125
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Asn Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Glu Ile Leu Thr Gly Tyr Gly Tyr Tyr Gly Met
            100                 105                 110

Asp Val Trp Gly Gln Gly Thr Thr Val Thr Val Ser Ser
        115                 120                 125

<210> SEQ ID NO 12
<211> LENGTH: 129
<212> TYPE: PRT
<213> ORGANISM: Homo sapiens

<400> SEQUENCE: 12

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Asp Tyr Ala
    50                  55                  60

Gly Ser Val Lys Ser Arg Ile Asn Ile Asn Pro Asp Thr Ser Lys Asn
65                  70                  75                  80

Gln Phe Ser Leu Gln Val Asn Ser Val Thr Pro Glu Asp Thr Ala Val
                85                  90                  95

Tyr Tyr Cys Thr Arg Asp Arg Ser Ser Gly Trp Asn Glu Gly Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 13
<211> LENGTH: 128
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
```

```
                 35                  40                  45
Ala Val Leu Ser Ser Asp Gly Asn Asn Lys Tyr Cys Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Glu Glu Val Tyr Tyr Asp Ile Leu Thr Gly Tyr Tyr Asp Tyr
                100                 105                 110

Tyr Gly Met Asp Val Trp Gly Gln Gly Thr Thr Val Thr Val Ser Ser
            115                 120                 125

<210> SEQ ID NO 14
<211> LENGTH: 126
<212> TYPE: PRT
<213> ORGANISM: Homo sapiens

<400> SEQUENCE: 14

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Thr Tyr
                 20                  25                  30

Phe Trp Thr Trp Ile Arg Gln Phe Pro Gly Lys Gly Leu Glu Trp Ile
             35                  40                  45

Gly Tyr Ile Phe Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Gly Tyr Tyr Asp Ile Leu Thr Gly Glu Asp Tyr Ser Tyr Gly
                100                 105                 110

Met Asp Val Trp Gly Gln Gly Thr Thr Val Thr Val Ser Ser
            115                 120                 125

<210> SEQ ID NO 15
<211> LENGTH: 129
<212> TYPE: PRT
<213> ORGANISM: Homo sapiens

<400> SEQUENCE: 15

Gln Val Gln Leu Gln Gln Ser Gly Pro Gly Leu Val Lys Pro Ser Gln
 1               5                  10                  15

Ile Leu Ser Leu Thr Cys Ala Ile Ser Gly Asp Arg Val Ser Ser Asn
                 20                  25                  30

Gly Ala Ala Trp Asn Trp Ile Arg Gln Ser Pro Ser Arg Gly Leu Glu
             35                  40                  45

Trp Leu Gly Arg Thr Tyr Tyr Arg Ser Lys Trp Tyr Tyr Asp Tyr Ala
 50                  55                  60

Gly Ser Val Lys Ser Arg Ile Asn Ile Asn Pro Asp Thr Ser Lys Asn
 65                  70                  75                  80

Gln Phe Ser Leu Gln Val Asn Ser Val Thr Pro Glu Asp Thr Ala Val
                 85                  90                  95

Tyr Tyr Cys Ala Arg Asp Arg Ser Ser Gly Trp Asn Glu Gly Tyr Tyr
                100                 105                 110

Tyr Tyr Gly Met Asp Val Trp Gly Gln Gly Thr Thr Val Thr Val Ser
```

Ser

<210> SEQ ID NO 16
<211> LENGTH: 126
<212> TYPE: PRT
<213> ORGANISM: Homo sapiens

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Phe Trp Thr Trp Ile Arg Gln Phe Pro Gly Glu Gly Leu Glu Trp Ile
        35                  40                  45

Gly Tyr Ile Phe Tyr Ser Gly Asn Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Asp Ile Leu Thr Gly Glu Asp Tyr Ser Tyr Gly
            100                 105                 110

Ile Asp Val Trp Gly Gln Gly Thr Thr Val Thr Val Ser Ser
        115                 120                 125

<210> SEQ ID NO 17
<211> LENGTH: 125
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Asn Lys Tyr Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Asp Ile Leu Thr Gly Asn Gly Val Tyr Gly Met
            100                 105                 110

Asp Val Trp Gly Gln Gly Thr Thr Val Thr Val Ser Ser
        115                 120                 125

<210> SEQ ID NO 18
<211> LENGTH: 122
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Tyr Ile Ser Gly Ser Ser Ser Leu Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Met Asn Ser Leu Arg Asp Glu Asp Thr Ala Val Tyr Tyr Cys
                85                  90                  95

Ala Arg Ala Arg Tyr Asn Trp Asn Asp Tyr Tyr Gly Met Asp Val Trp
            100                 105                 110

Gly Gln Gly Thr Thr Val Thr Val Ser Ser
            115                 120

<210> SEQ ID NO 19
<211> LENGTH: 116
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Ile His Trp Val Arg Gln Ala Pro Gly Lys Gly Leu Glu Trp Val
        35                  40                  45

Ala Gly Ile Trp Tyr Asp Gly Ser Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Phe Asp Ala Phe Asp Ile Trp Gly Gln Gly Thr Met Val
            100                 105                 110

Thr Val Ser Ser
115

<210> SEQ ID NO 20
<211> LENGTH: 128
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Thr Met Asn Trp Val Arg Gln Ala Pro Gly Lys Gly Leu Glu Trp Val
        35                  40                  45

Ser Tyr Ile Ser Ser Ser Ser Leu Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Ser Asp Tyr Tyr Gly Ser Gly Ser Tyr Lys Gly Asn Tyr
            100                 105                 110

Tyr Gly Met Asp Val Trp Gly Gln Gly Thr Thr Val Thr Val Ser Ser
        115                 120                 125

<210> SEQ ID NO 21
<211> LENGTH: 128
<212> TYPE: PRT
<213> ORGANISM: Homo sapiens

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp Ser Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Arg Gly Leu Tyr Asp Ile Leu Thr Gly Tyr Tyr Asp Tyr
            100                 105                 110

Tyr Gly Ile Asp Val Trp Gly Gln Gly Thr Thr Val Thr Val Ser Ser
        115                 120                 125

<210> SEQ ID NO 22
<211> LENGTH: 128
<212> TYPE: PRT
<213> ORGANISM: Homo sapiens

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp Ser Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Glu Arg Gly Leu Tyr Asp Ile Leu Thr Gly Tyr Tyr Asp Tyr
            100                 105                 110

Tyr Gly Ile Asp Val Trp Gly Gln Gly Thr Thr Val Thr Val Ser Ser
        115                 120                 125

<210> SEQ ID NO 23
<211> LENGTH: 116
<212> TYPE: PRT
<213> ORGANISM: Homo sapiens

<400> SEQUENCE: 23

Glu Val Gln Leu Val Glu Ser Gly Gly Gly Leu Val Lys Pro Gly Gly

```
1               5                   10                  15
Ser Leu Arg Leu Ser Cys Ala Ala Ser Gly Ile Thr Phe Arg Ser Tyr
            20                  25                  30

Ser Met Asn Trp Val Arg Gln Ala Pro Gly Lys Gly Leu Glu Trp Val
            35                  40                  45

Ser Ala Ile Ser Ser Ser Ser Tyr Ile Tyr Tyr Ala Asp Ser Val
            50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
            85                  90                  95

Ala Arg Gly Arg Tyr Gly Met Asp Val Trp Gly Gln Gly Thr Thr Val
            100                 105                 110

Thr Val Ser Ser
            115
```

<210> SEQ ID NO 24
<211> LENGTH: 125
<212> TYPE: PRT
<213> ORGANISM: Homo sapiens

<400> SEQUENCE: 24

```
Gln Val Gln Leu Val Glu Ser Gly Gly Gly Val Val Gln Pro Gly Arg
1               5                   10                  15

Ser Leu Arg Leu Ser Cys Ala Ala Ser Gly Ser Thr Phe Arg Ser Tyr
            20                  25                  30

Asp Met His Trp Val Arg Gln Ala Pro Gly Lys Gly Leu Glu Trp Val
            35                  40                  45

Ala Val Ile Ser Tyr Asp Gly Ser Asn Lys Tyr Tyr Gly Asp Ser Val
            50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gln Tyr Asp Ile Leu Thr Gly Tyr Ser Ser Asp Ala Phe
            100                 105                 110

Asp Ile Trp Gly Gln Gly Thr Met Val Thr Val Ser Ser
            115                 120                 125
```

<210> SEQ ID NO 25
<211> LENGTH: 127
<212> TYPE: PRT
<213> ORGANISM: Homo sapiens

<400> SEQUENCE: 25

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser His Lys Tyr Tyr Glu Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Gly Val Tyr Tyr Cys
```

```
                    85                  90                  95
Ala Arg Val Gly Tyr Gly Ser Gly Trp Tyr Glu Tyr Tyr His Tyr
                100                 105                 110

Gly Met Asp Val Trp Gly Gln Gly Thr Thr Val Thr Val Ser Ser
            115                 120                 125

<210> SEQ ID NO 26
<211> LENGTH: 128
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Met Trp Tyr Asp Gly Ser Asn Lys Asp Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
                100                 105                 110

Tyr Gly Leu Asp Val Trp Gly Gln Gly Thr Thr Val Thr Val Ser Ser
            115                 120                 125

<210> SEQ ID NO 27
<211> LENGTH: 128
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Met Trp Tyr Asp Gly Ser Asn Lys Asp Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
                100                 105                 110

Tyr Gly Leu Asp Val Trp Gly Gln Gly Thr Thr Val Thr Val Ser Ser
            115                 120                 125

<210> SEQ ID NO 28
<211> LENGTH: 116
<212> TYPE: PRT
<213> ORGANISM: Homo sapiens

<400> SEQUENCE: 28
```

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
            35                  40                  45

Ala Ser Ile Trp Tyr Asp Gly Ser Asn Lys Tyr Tyr Val Asp Ser Val
50                  55                  60

Lys Gly Arg Phe Thr Ile Phe Arg Asp Asn Ser Lys Lys Thr Leu Tyr
65                  70                  75                  80

Leu Gln Met Asn Arg Leu Arg Ala Glu Asp Thr Ala Val Tyr Tyr Cys
            85                  90                  95

Ala Arg Leu Gly Gly Gly Phe Asp Tyr Trp Gly Gln Gly Thr Leu Val
            100                 105                 110

Thr Val Ser Ser
            115

<210> SEQ ID NO 29
<211> LENGTH: 108
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Lys Lys Pro Gly Lys Ala Pro Lys Ser Leu Ile
            35                  40                  45

Tyr Val Val Ser Ser Leu Gln Ser Gly Val Pro Ser Arg Phe Ser Gly
        50                  55                  60

Ser Gly Ser Gly Thr Asp Phe Thr Leu Thr Ile Asn Asn Leu Gln Pro
65                  70                  75                  80

Glu Asp Phe Ala Thr Tyr Tyr Cys Gln Gln Tyr Asn His Tyr Pro Leu
            85                  90                  95

Thr Phe Gly Gly Gly Thr Arg Val Glu Ile Lys Arg
            100                 105

<210> SEQ ID NO 30
<211> LENGTH: 108
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Arg Pro Gly Lys Ala Pro Lys Ser Leu Ile
            35                  40                  45

Tyr Val Val Ser Ser Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
65                  70                  75                  80

Glu Asp Phe Ala Thr Tyr Phe Cys Gln Gln Tyr Asn His Tyr Pro Leu
            85                  90                  95

```
Thr Phe Gly Gly Gly Thr Lys Val Glu Ile Lys Arg
            100                 105
```

```
<210> SEQ ID NO 31
<211> LENGTH: 108
<212> TYPE: PRT
<213> ORGANISM: Homo sapiens

<400> SEQUENCE: 31

Asp Ile Gln Met Thr Gln Phe Pro Ser Ser Leu Ser Ala Ser Ile Gly
1               5                   10                  15

Asp Arg Val Thr Ile Thr Cys Gln Ala Ser Gln Asp Ile Ser Asn Phe
            20                  25                  30

Leu Asn Trp Phe Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
    50                  55                  60

Ser Gly Ala Gly Thr Asp Phe Thr Phe Thr Ile Ser Ser Leu Gln Pro
65                  70                  75                  80

Glu Asp Ile Ala Thr Tyr Phe Cys Gln Gln Tyr Asp Asp Leu Pro Leu
                85                  90                  95

Thr Phe Gly Gly Gly Thr Arg Val Asp Ile Lys Arg
            100                 105
```

```
<210> SEQ ID NO 32
<211> LENGTH: 108
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gly Gly Thr Lys Val Glu Ile Lys Arg
            100                 105
```

```
<210> SEQ ID NO 33
<211> LENGTH: 109
<212> TYPE: PRT
<213> ORGANISM: Homo sapiens

<400> SEQUENCE: 33

Gln Asn Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Phe Gly Val Ser Ser Arg Ala Thr Gly Ile Pro Asp Arg Phe Ser
 50                  55                  60

Gly Ser Gly Ser Gly Thr Asp Phe Ser Leu Thr Ile Ser Arg Leu Glu
 65                  70                  75                  80

Pro Glu Asp Phe Ala Val Tyr Tyr Cys Gln Gln Tyr Gly Asn Ser Pro
                 85                  90                  95

Phe Thr Phe Gly Pro Gly Thr Lys Val Asp Ile Lys Arg
                100                 105
```

```
<210> SEQ ID NO 34
<211> LENGTH: 108
<212> TYPE: PRT
<213> ORGANISM: Homo sapiens

<400> SEQUENCE: 34
```

```
Asp Ile Gln Met Thr Gln Phe Pro Ser Ser Leu Ser Ala Ser Ile Gly
 1                5                  10                  15

Asp Arg Val Thr Ile Thr Cys Gln Ala Ser Gln Asp Ile Ser Asn Phe
                 20                  25                  30

Leu Asn Trp Phe Gln Gln Lys Pro Gly Lys Ala Pro Lys Leu Leu Ile
             35                  40                  45

Tyr Asp Ala Ser Asp Leu Glu Thr Gly Val Pro Ser Arg Phe Ser Gly
 50                  55                  60

Ser Gly Ala Gly Thr Asp Phe Thr Phe Thr Ile Ser Ser Leu Gln Pro
 65                  70                  75                  80

Glu Asp Val Ala Thr Tyr Phe Cys Gln Gln Tyr Asp Asn Leu Pro Leu
                 85                  90                  95

Thr Phe Gly Gly Gly Thr Lys Val Asp Ile Lys Arg
                100                 105
```

```
<210> SEQ ID NO 35
<211> LENGTH: 109
<212> TYPE: PRT
<213> ORGANISM: Homo sapiens

<400> SEQUENCE: 35
```

```
Glu Asn Val Leu Thr Gln Ser Pro Gly Thr Leu Ser Leu Ser Pro Gly
 1                5                  10                  15

Glu Arg Ala Thr Leu Ser Cys Arg Ala Ser Gln Ser Val Thr Ser Ser
                 20                  25                  30

Tyr Leu Ala Trp Tyr Gln Gln Lys Pro Gly Gln Ala Pro Arg Leu Leu
             35                  40                  45

Ile Phe Gly Val Ser Ser Arg Ala Thr Gly Ile Pro Asp Arg Phe Ser
 50                  55                  60

Gly Ser Gly Ser Gly Thr Asp Phe Ser Leu Thr Ile Ser Arg Leu Glu
 65                  70                  75                  80

Pro Glu Asp Phe Ala Val Tyr Tyr Cys Gln Gln Tyr Gly Asn Ser Pro
                 85                  90                  95

Phe Thr Phe Gly Pro Gly Thr Lys Val Asp Ile Lys Arg
                100                 105
```

```
<210> SEQ ID NO 36
<211> LENGTH: 108
<212> TYPE: PRT
<213> ORGANISM: Homo sapiens

<400> SEQUENCE: 36
```

```
Asp Ile Gln Met Thr Gln Ser Pro Ser Ser Leu Ser Ala Ser Val Gly
```

```
              1               5                  10                 15
          Asp Arg Val Thr Ile Thr Cys Arg Ala Ser Gln Gly Ile Asp Met Tyr
                          20                  25                  30

Leu Ala Trp Phe Gln Gln Lys Pro Gly Lys Ala Pro Lys Ser Leu Ile
                          35                  40                  45

Tyr Ala Ala Ser Ser Leu Gln Ser Gly Val Pro Ser Lys Phe Ser Gly
                          50                  55                  60

Ser Gly Phe Gly Thr Asp Phe Thr Leu Thr Ile Ser Ser Leu Gln Pro
          65                  70                  75                  80

Glu Asp Phe Ala Thr Tyr Tyr Cys Gln Gln Tyr Asn Ile Phe Pro Phe
                          85                  90                  95

Thr Phe Gly Pro Gly Thr Lys Val Asp Val Lys Arg
                          100                 105

<210> SEQ ID NO 37
<211> LENGTH: 108
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
          1               5                  10                  15

Asp Arg Val Thr Ile Thr Cys Arg Ala Ser Gln Gly Ile Arg Asn Asp
                          20                  25                  30

Leu Gly Trp Tyr Gln Gln Lys Pro Gly Lys Ala Pro Lys Arg Leu Ile
                          35                  40                  45

Tyr Ala Ala Ser Ser Leu Glu Ser Gly Val Pro Ser Arg Phe Ser Gly
                          50                  55                  60

Ser Gly Ser Gly Thr Glu Phe Thr Leu Thr Ile Ser Ser Leu Gln Pro
          65                  70                  75                  80

Glu Asp Phe Ala Thr Tyr Tyr Cys Leu Gln His Asn Ser Tyr Pro Trp
                          85                  90                  95

Thr Phe Gly Gln Gly Thr Lys Val Glu Ile Lys Arg
                          100                 105

<210> SEQ ID NO 38
<211> LENGTH: 114
<212> TYPE: PRT
<213> ORGANISM: Homo sapiens

<400> SEQUENCE: 38

Lys Ile Val Met Thr Gln Thr Pro Leu Ala Leu Pro Val Ile Pro Gly
          1               5                  10                  15

Glu Pro Ala Ser Ile Ser Cys Arg Ser Ser Gln Ser Leu Val Asp Ser
                          20                  25                  30

Asp Asp Gly Asp Thr Tyr Leu Asp Trp Tyr Leu Gln Lys Pro Gly Gln
                          35                  40                  45

Ser Pro Gln Val Leu Ile His Arg Leu Ser Tyr Arg Ala Ser Gly Val
                          50                  55                  60

Pro Asp Arg Phe Ser Gly Ser Gly Ser Gly Thr Asp Phe Thr Leu Lys
          65                  70                  75                  80

Ile Ser Arg Val Glu Ala Glu Asp Val Gly Ile Tyr Tyr Cys Met His
                          85                  90                  95

Arg Ile Glu Phe Pro Phe Thr Phe Gly Gly Gly Thr Lys Val Glu Ile
                          100                 105                 110

Lys Arg
```

<210> SEQ ID NO 39
<211> LENGTH: 108
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Arg Pro Gly Lys Ala Pro Lys Arg Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys Arg
            100                 105

<210> SEQ ID NO 40
<211> LENGTH: 113
<212> TYPE: PRT
<213> ORGANISM: Homo sapiens

<400> SEQUENCE: 40

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Met Cys Ser Phe Gly Gln Gly Thr Lys Leu Glu Ile Lys
            100                 105                 110

Arg

<210> SEQ ID NO 41
<211> LENGTH: 113
<212> TYPE: PRT
<213> ORGANISM: Homo sapiens

<400> SEQUENCE: 41

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Glu Ala
                 85                  90                  95

Leu Gln Thr Met Ser Ser Phe Gly Gln Gly Thr Lys Leu Glu Ile Lys
                100                 105                 110

Arg

<210> SEQ ID NO 42
<211> LENGTH: 114
<212> TYPE: PRT
<213> ORGANISM: Homo sapiens

<400> SEQUENCE: 42

Asp Ile Val Met Thr Gln Thr Pro Leu Phe Leu Pro Val Thr Pro Gly
 1               5                  10                  15

Glu Pro Ala Ser Ile Ser Cys Arg Ser Ser Gln Thr Leu Leu Asp Ser
                20                  25                  30

Asp Asp Gly Asn Thr Tyr Leu Asp Trp Tyr Leu Gln Lys Pro Gly Gln
             35                  40                  45

Ser Pro Gln Arg Leu Ile Tyr Thr Leu Ser Tyr Arg Ala Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Met Gln
                 85                  90                  95

His Ile Glu Phe Pro Ser Thr Phe Gly Gln Gly Thr Arg Leu Glu Ile
                100                 105                 110

Lys Arg

<210> SEQ ID NO 43
<211> LENGTH: 107
<212> TYPE: PRT
<213> ORGANISM: Homo sapiens

<400> SEQUENCE: 43

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
                20                  25                  30

Ser Trp Tyr Gln Gln Lys Pro Gly Gln Ser Pro Val Leu Val Ile Tyr
             35                  40                  45

Gln Ser Thr Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Val Val
                 85                  90                  95

Phe Gly Gly Gly Thr Lys Leu Thr Val Leu Gly
                100                 105

<210> SEQ ID NO 44
<211> LENGTH: 113
<212> TYPE: PRT
<213> ORGANISM: Homo sapiens
```

<400> SEQUENCE: 44

Asn Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Asn Tyr Leu Phe Trp Tyr Leu Gln Lys Pro Gly Gln Ser
        35                  40                  45

Pro Gln Leu Leu Ile Tyr Glu Val Ser Tyr Arg Phe Ser Gly Val Pro
    50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Asn
                85                  90                  95

Ile Gln Pro Pro Leu Thr Phe Gly Gln Gly Thr Arg Leu Glu Ile Lys
            100                 105                 110

Arg

<210> SEQ ID NO 45
<211> LENGTH: 108
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
            100                 105

<210> SEQ ID NO 46
<211> LENGTH: 108
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg
            100                 105

<210> SEQ ID NO 47
<211> LENGTH: 114
<212> TYPE: PRT
<213> ORGANISM: Homo sapiens

<400> SEQUENCE: 47

Asp Ile Val Leu Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Arg
            20                  25                  30

Asp Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Ser Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys Arg

<210> SEQ ID NO 48
<211> LENGTH: 107
<212> TYPE: PRT
<213> ORGANISM: Homo sapiens

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 49
<211> LENGTH: 106
<212> TYPE: PRT
<213> ORGANISM: Homo sapiens

<400> SEQUENCE: 49

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro

```
                35                  40                  45
Val Lys Ala Gly Val Glu Thr Thr Pro Ser Lys Gln Ser Asn Asn
 50                  55                  60
Lys Tyr Ala Ala Ser Ser Tyr Leu Ser Leu Thr Pro Glu Gln Trp Lys
 65                  70                  75                  80
Ser His Arg Ser Tyr Ser Cys Gln Val Thr His Glu Gly Ser Thr Val
                 85                  90                  95
Glu Lys Thr Val Ala Pro Thr Glu Cys Ser
                100                 105

<210> SEQ ID NO 50
<211> LENGTH: 326
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
  1               5                  10                  15
Ser Thr Ser Glu Ser Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Asn Phe Gly Thr Gln Thr
 65                  70                  75                  80
Tyr Thr Cys Asn Val Asp His Lys Pro Ser Asn Thr Lys Val Asp Lys
                 85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 51
<211> LENGTH: 454
<212> TYPE: PRT
<213> ORGANISM: Homo sapiens

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
        195                 200                 205

Tyr Thr Cys Asn Val Asp His Lys Pro Ser Asn Thr Lys Val Asp Lys
    210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Phe Arg Val Val Ser Val Leu Thr Val Val His Gln Asp Trp
305                 310                 315                 320

Leu Asn Gly Lys Glu Tyr Lys Cys Lys Val Ser Asn Lys Gly Leu Pro
                325                 330                 335

Ala Pro Ile Glu Lys Thr Ile Ser Lys Thr Lys Gly Gln Pro Arg Glu
            340                 345                 350

```
Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Met Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 52
<211> LENGTH: 214
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```